US009745558B2

(12) United States Patent
Gerometta et al.

(10) Patent No.: US 9,745,558 B2
(45) Date of Patent: Aug. 29, 2017

(54) VEGFR-3 LIGAND BINDING MOLECULES AND USES THEREOF

(71) Applicant: VEGENICS PTY LIMITED, South Yarra, Victoria (AU)

(72) Inventors: Michael Gerometta, Robertson (AU); Timothy Adams, Lower Plenty (AU)

(73) Assignee: VEGENICS PTY LIMITED, South Yarra, Victoria (AU)

(*) Notice: Subject to any disclaimer, the term of this patent is extended or adjusted under 35 U.S.C. 154(b) by 0 days.

(21) Appl. No.: 14/768,701

(22) PCT Filed: Feb. 13, 2014

(86) PCT No.: PCT/AU2014/000114
§ 371 (c)(1),
(2) Date: Aug. 18, 2015

(87) PCT Pub. No.: WO2014/124487
PCT Pub. Date: Aug. 21, 2014

(65) Prior Publication Data
US 2016/0002612 A1     Jan. 7, 2016

Related U.S. Application Data

(60) Provisional application No. 61/782,376, filed on Mar. 14, 2013, provisional application No. 61/765,841, filed on Feb. 18, 2013.

(51) Int. Cl.
| A61K 38/17 | (2006.01) |
| C07K 14/435 | (2006.01) |
| C12N 9/12 | (2006.01) |
| A61K 45/06 | (2006.01) |
| A61K 47/48 | (2006.01) |
| C07K 14/71 | (2006.01) |
| A61K 38/45 | (2006.01) |
| A61K 39/395 | (2006.01) |
| C07K 16/00 | (2006.01) |
| A61K 38/00 | (2006.01) |

(52) U.S. Cl.
CPC ........... *C12N 9/12* (2013.01); *A61K 38/45* (2013.01); *A61K 39/395* (2013.01); *A61K 45/06* (2013.01); *A61K 47/48246* (2013.01); *C07K 14/71* (2013.01); *C07K 16/00* (2013.01); *A61K 38/00* (2013.01); *C07K 2319/00* (2013.01); *C07K 2319/30* (2013.01); *C07K 2319/31* (2013.01); *C07K 2319/70* (2013.01); *C12N 2710/10043* (2013.01); *C12Y 207/10001* (2013.01)

(58) Field of Classification Search
None
See application file for complete search history.

(56) References Cited

U.S. PATENT DOCUMENTS

| 4,543,439 | A | 9/1985 | Frackelton, Jr. et al. |
| 5,183,884 | A | 2/1993 | Kraus et al. |
| 5,231,001 | A | 7/1993 | Kaplan et al. |
| 5,270,458 | A | 12/1993 | Lemischka |
| 5,283,354 | A | 2/1994 | Lemischka |
| 5,367,057 | A | 11/1994 | Lemischka |
| 5,635,177 | A | 6/1997 | Bennett et al. |
| 5,693,762 | A | 12/1997 | Queen et al. |
| 5,700,822 | A | 12/1997 | Hirth et al. |
| 5,712,395 | A | 1/1998 | App et al. |
| 5,747,651 | A | 5/1998 | Lemischka |
| 5,750,078 | A | 5/1998 | Shitara et al. |
| 5,763,441 | A | 6/1998 | App et al. |
| 5,763,733 | A | 6/1998 | Whitlow et al. |
| 5,776,427 | A | 7/1998 | Thorpe et al. |
| 5,776,755 | A | 7/1998 | Alitalo et al. |
| 5,798,097 | A | 8/1998 | McKenzie et al. |
| 5,807,548 | A | 9/1998 | Shitara et al. |
| 5,932,540 | A | 8/1999 | Hu et al. |
| 5,935,820 | A | 8/1999 | Hu et al. |
| 5,952,199 | A | 9/1999 | Davis-Smyth et al. |
| 6,011,003 | A | 1/2000 | Charnock-Jones et al. |
| 6,040,157 | A | 3/2000 | Hu et al. |
| 6,100,071 | A | 8/2000 | Davis-Smyth et al. |
| 6,107,046 | A | 8/2000 | Alitalo et al. |
| 6,130,071 | A | 10/2000 | Alitalo et al. |
| 6,221,839 | B1 | 4/2001 | Alitalo et al. |
| 6,235,713 | B1 | 5/2001 | Achen et al. |
| 6,245,530 | B1 | 6/2001 | Alitalo et al. |
| 6,331,302 | B1 | 12/2001 | Bennett et al. |
| 6,361,946 | B1 | 3/2002 | Alitalo et al. |
| 6,383,484 | B1 | 5/2002 | Achen et al. |

(Continued)

FOREIGN PATENT DOCUMENTS

| EP | 0 325 224 A2 | 7/1989 |
| EP | 0 935 001 A1 | 8/1999 |

(Continued)

OTHER PUBLICATIONS

"Angiogenesis Inhibitors in Clinical Trials, Cancer Trials", at cancertrials.nci.nih.gove/news/angio/table.html (visited Jan. 24, 2001).
"Angiogenesis Inhibitors in Clinical Trials, Cancer Trials", at cancertrials.nci.nih.gove/news/angio/table.html (visited Sep. 25, 2001).
Achen et al., Localization of Vascular Endothelial Growth Factor-D in Malignant Melanoma Suggests a Role in Tumour Angiogenesis, *J. Pathol.*, 193(2):147-54 (2001).
Achen et al., Monoclonal antibodies to vascular endothelial growth factor-D block its interactions with both VEGF receptor-2 and VEGF receptor-3, *Eur. J. Biochem.*, 267(9):2505-15 (2000).
Achen et al., Vascular endothelial growth factor D (VEGF-F) is a ligand for the tyrosine kinases VEGF receptor 2 (Flk1) and VEGF receptor 3 (Flt4), *Proc. Natl. Acad. Sci. USA*, 95(2):548-553 (1998).

(Continued)

*Primary Examiner* — Christine J Saoud
(74) *Attorney, Agent, or Firm* — Marshall, Gerstein & Borun LLP

(57) ABSTRACT

The present invention is directed to VEGFR-3 ligand binding molecules and uses thereof to modulate angiogenesis and/or lymphangiogenesis. A glycosylation sequon of wild-type VEGFR-3 has been modified to eliminate glycosylation in the ligand binding molecules.

49 Claims, 13 Drawing Sheets

(56) References Cited

U.S. PATENT DOCUMENTS

| | | |
|---|---|---|
| 6,383,486 B1 | 5/2002 | Davis-Smyth et al. |
| 6,403,088 B1 | 6/2002 | Alitalo et al. |
| 6,451,764 B1 | 9/2002 | Lee et al. |
| 6,576,608 B1 | 6/2003 | Lee et al. |
| 6,608,182 B1 | 8/2003 | Rosen et al. |
| 6,645,933 B1 | 11/2003 | Alitalo et al. |
| 6,673,343 B2 | 1/2004 | Bennett et al. |
| 6,689,580 B1 | 2/2004 | Achen et al. |
| 6,730,658 B1 | 5/2004 | Alitalo et al. |
| 6,824,777 B1 | 11/2004 | Alitalo et al. |
| 6,965,010 B2 | 11/2005 | Alitalo et al. |
| 7,034,105 B2 | 4/2006 | Alitalo et al. |
| 7,422,741 B2 | 9/2008 | Alitalo et al. |
| 7,566,566 B2 | 7/2009 | Alitalo et al. |
| 7,611,711 B2 | 11/2009 | Alitalo et al. |
| 7,829,091 B2 | 11/2010 | Alitalo |
| 7,855,178 B2 | 12/2010 | Alitalo et al. |
| 7,902,149 B2 | 3/2011 | Alitalo et al. |
| 8,278,098 B2 | 10/2012 | Alitalo et al. |
| 8,444,957 B2 | 5/2013 | Alitalo et al. |
| 2001/0038842 A1 | 11/2001 | Achen et al. |
| 2002/0065218 A1 | 5/2002 | Achen et al. |
| 2002/0102260 A1 | 8/2002 | Achen et al. |
| 2002/0120123 A1 | 8/2002 | Rosen et al. |
| 2002/0123481 A1 | 9/2002 | Oliviero |
| 2002/0127222 A1 | 9/2002 | Achen et al. |
| 2002/0146420 A1 | 10/2002 | Bennett et al. |
| 2002/0151489 A1 | 10/2002 | Gravereaux et al. |
| 2002/0182683 A1 | 12/2002 | Hu et al. |
| 2002/0197691 A1 | 12/2002 | Sugiyama |
| 2003/0008357 A1 | 1/2003 | Hu et al. |
| 2003/0028007 A1 | 2/2003 | Hu et al. |
| 2003/0091567 A1 | 5/2003 | Alitalo et al. |
| 2003/0092604 A1 | 5/2003 | Davis-Smyth et al. |
| 2003/0125537 A1 | 7/2003 | Achen et al. |
| 2003/0166523 A1 | 9/2003 | Achen et al. |
| 2003/0166547 A1 | 9/2003 | Oliviero |
| 2003/0166873 A1 | 9/2003 | Lee et al. |
| 2003/0170786 A1 | 9/2003 | Rosen et al. |
| 2003/0175274 A1 | 9/2003 | Rosen et al. |
| 2003/0176674 A1 | 9/2003 | Rosen et al. |
| 2003/0180294 A1 | 9/2003 | DeVries |
| 2003/0211101 A1 | 11/2003 | Wise et al. |
| 2003/0211988 A1 | 11/2003 | Epstein |
| 2003/0215921 A1 | 11/2003 | Coleman |
| 2003/0228283 A1 | 12/2003 | Heinzerling et al. |
| 2003/0232437 A1 | 12/2003 | Zhang et al. |
| 2004/0037820 A1 | 2/2004 | Alitalo et al. |
| 2006/0177901 A1 | 8/2006 | Alitalo et al. |
| 2010/0278736 A1 | 11/2010 | Alitalo et al. |
| 2011/0243912 A1 | 10/2011 | Alitalo et al. |

FOREIGN PATENT DOCUMENTS

| | | |
|---|---|---|
| WO | WO-90/14425 A1 | 11/1990 |
| WO | WO-92/13867 A1 | 8/1992 |
| WO | WO-92/14748 A1 | 9/1992 |
| WO | WO-93/14124 A1 | 7/1993 |
| WO | WO-93/15201 A1 | 8/1993 |
| WO | WO-94/10202 A1 | 5/1994 |
| WO | WO-95/24473 A1 | 9/1995 |
| WO | WO-95/33772 A1 | 12/1995 |
| WO | WO-96/39515 A1 | 12/1996 |
| WO | WO-97/05250 A2 | 2/1997 |
| WO | WO-97/09427 A1 | 3/1997 |
| WO | WO-97/12972 A2 | 4/1997 |
| WO | WO-98/02543 A1 | 1/1998 |
| WO | WO-98/07832 A1 | 2/1998 |
| WO | WO-98/33917 A1 | 8/1998 |
| WO | WO-99/33485 A1 | 7/1999 |
| WO | WO-00/45835 A1 | 8/2000 |
| WO | WO-00/75319 A1 | 12/2000 |
| WO | WO-2004/009773 A2 | 1/2004 |
| WO | WO-2005/000895 A2 | 1/2005 |
| WO | WO-2005/087808 A2 | 9/2005 |
| WO | WO-2006/088650 A2 | 8/2006 |
| WO | WO-2007/096398 A1 | 8/2007 |
| WO | WO-2007/149334 A2 | 12/2007 |

OTHER PUBLICATIONS

Akagi et al., Vascular endothelial growth factor-C (VEGF-C) expression in colorectal cancer tissues, *Br. J. Cancer*, 83(7):887-91 (2000).

Alon et al., Vascular endothelial growth factor acts as a survival factor for newly formed retinal vessels and has implications for retinopathy of prematurity, *Nat. Med.*, 1(10):1024-8 (1995).

Andersson et al., Structural and Functional Markers During Induced Differentiation in Human Leukemia Cell Lines, In R. F. Revoltella (ed.), Expression of Differentiated Functions in Cancer Cells. 239 245, Raven Press, New York (1982).

Andre et al., Vegf, Vegf-B, Vegf-C and their receptors KDR, FLT-1 and FL the neoplastic progression of human colonic mucosa, *Int. J. Cancer*, 86(2):174-81 (2000).

Aprelikova et al., FLT4, A Novel Class III Receptor Tyrosine Kinase in Chromosome 5q33-qter, *Cancer Research*, 52(3):746-8 (1992).

Aujame et al., High affinity human antibodies by phage display, *Human Antibodies*, 8(4):155-68 (1997).

Baldwin et al., The specificity of receptor binding by vascular endothelial growth factor-d is different in mouse and man, *J. Biol. Chem.*, 276:19166-71 (2001).

Banerji et al., LYVE 1, a new homologue of the CD44 glycoprotein, is a lymph specific receptor for hyaluronan, *J Cell Biol.*, 144(4):789-801 (1999).

Beasley et al., Intratumoral Lymphangiogenesis and Lymph Node Metastasis in Head and Neck Cancer, *Cancer Res*, 62:1315-20 (2002).

Beckstead et al., Evidence for the Origin of Kaposi's Sarcoma From Lymphatic Endothelium, *Am. J. Pathol.*, 119(2):294-300 (1985).

Benjamin et al., Selective ablation of immature blood vessels in established human tumors follows vascular endothelial growth factor withdrawal, *J. Clin. Invest.*, 103(2): 159-65 (1999).

Berridge et al., Cell-Lineage Antigens of the Stem Cell-Megakaryocyte-Platelet Linkage are Associated with the Platelet IIb-IIIa Glycoprotein Complex, *Blood*, 66(1):76-85 (1985).

Birner et al., Lymphatic Microvessel Density as a Novel Prognostic Factor in Early-Stage Invasive Cervical Cancer, *In.t J. Cancer*, 95:29-33 (2001).

Birner et al., Selective Immunohistochemical Staining of Blood and Lymphatic Vessels Reveals Independent Prognostic Influence of Blood and Lymphatic Vessel Invasion in Early-Stage Cervical Cancer, *Clin. Cancer Res.*, 7:93-7 (2001).

Bolen, Nonreceptor Tyrosine Protein Kinases, *Oncogene*, 8:2025-31 (1993).

Borg et al., Biochemical Characterization of Two Isoforms of FLT4, a VEGF Receptor-Related Tyrosin Kinase, *Oncogene*, 10:973-84 (1995).

Bork et al., The immunoglobulin fold. Structural classification, sequence patterns and common core, *J. Mol. Biol.*, 242: 309-320 (1994).

Brown et al., Expression of Vascular Permeability Factor (Vascular Endothelial Growth Factor) and Its Receptors in Breast Cancer, *Human Pathology*, 26(1):86-91 (1995).

Brüggemann et al., Production of human antibody repertoires in transgenic mice, *Curr. Opin. Biotechnol.*, 8:455-8 (1997).

Brüggemann et al., Strategies for expressing human antibody repertoires in transgenic mice, *Immunol. Today*, 17(8):391-7 (1996).

Bunone et al., Expression of Angiogenesis Stimulators and Inhibitors in Human Thyroid Tumors and Correlation with Clinical Pathological Features, *Am. J. Pathol.*, 155(6):1967-76 (1999).

Cao et al., Vascular endothelial growth factor C induces angiogenesis in vivo, *Proc. Natl. Acad. Sci. USA*, 95:14389-94 (1998).

Carmeliet et al., Abnormal blood vessel development and lethality in embryos lacking a single VEGF allele, *Nature*, 380(6573):435-9 (1996).

(56) References Cited

OTHER PUBLICATIONS

Carreira et al., LYVE-1 is not Restricted to the Lymph Vessels: Expression in Normal Liver Blood Sinusoids and Down-Regulation in Human Liver Cancer and Cirrhosis, *Cancer Res.*, 61:8079-84 (2001).

Carter et al., Toward the Production of Bispecific Antibody Fragments for Clinical Applications, *J. Hematother.*, 4:463-70 (1995).

Catoretti et al., Monoclonal Antibodies Against Recombinant Parts of the Ki-67 Antigen (MIB 1 and MIB 3) Detect Proliferating Cells in Microwave-Processed Formalin-Fixed Paraffin Section, *J. Pathol.*, 168:357-63 (1992).

Cheng et al., Identification and Cloning of ELF-1, a Developmentally Expressed Ligand for the Mek4 and Sek Receptor Tyrosine Kinases, *Cell*, 79:157-68 (1994).

Cole et al., The EBV-Hybridoma Technique and Its Application to Human Lung Cancer, Monoclonal Antibodies and Cancer Therapy, *Alan R Liss, Inc.*, 77-96 (1985).

Davis-Smyth et al., The second immunoglobulin-like domain of the VEGF tyrosine kinase receptor Flt-1 determines ligand bind and may initiate a signal transduction cascade, *EMBO J.*, 15(18)4919-27 (1996).

Davydova et al., Preparation of human vascular endothelial growth factor-D for structural and preclinical therapeutic studies, *Protein Expression and Purification*, 82:232-9 (2012).

De Gast et al., Clinical perspectives of bispecific antibodies in cancer, *Cancer Immunol. Immunother.*, 45:121-3 (1997).

De Vries et al., The fms-Like Tyrosine Kinase, a Receptor for Vascular Endothelial Growth Factor, *Science*, 255:989-91 (1992).

De Waal et al., Technical Advance: Lack of Lymphangiogenesis in Human Primary Cutaneous Melanoma, *Amer. J. Pathol.*, 150(6):1951-7 (1997).

Dias et al., Vascular endothelial growth factor (VEGF)-C signaling through FLt-4 (VEGFR-3) mediates leukemic cell proliferation, survival, and resistance to chemotherapy, *Blood*, 99:2179-84 (2002).

Dumont et al., Cardiovascular Failure in Mouse Embryos Deficient in VEGF Receptor 3, *Science*, 282(5390):946-49 (1998).

Eggert et al., High-Level Expression of Angiogenic Factors Is Associated with Advanced Tumor Stage in Human Neuroblastomas, *Clin. Cancer Res.*, 6(5):1900-8 (2000).

Eichmann et al., Molecular cloning of Quek 1 and 2, two quail vascular endothelial growth factor (VEGF) receptor-like molecules, *Gene*, 174(1):3-8 (1996).

Enholm et al., Adenoviral expression of vascular endothelial growth factor-C induces lymphangiogenesis in the skin, *Circ. Res.*, 88(6):623-9 (2001).

Enholm et al., Vascular Endothelial Growth Factor-C, a Growth Factor for Lymphatic and Blood Vascular Endothelial Cells, *TCM*, 8(7):292-7 (1998).

Evans et al., Mapping of primary congenital lymphedema to the 5q35.3 region, *Am. J. Hum. Genet.*, 64:547-55 (1999).

Fellmer et al., Vascular endothelial growth factor-C gene expression in papillary and follicular thyroid carcinomas, *Surgery*, 126(6):1056-61 (1999).

Fernandez-Botran, Soluble Cytokine Receptors: Novel Immunotherapeutic Agents, *Exp. Opin. Invest. Drugs*, 9:497-514 (2000).

Ferrara et al., Heterozygous embryonic lethality induced by targeted inactivation of the VEGF gene, *Nature*, 380(6573):439-42 (1996).

Ferrara et al., Molecular and Biological Properties of Vascular Endothelial Growth Factor, *J Mol Med.*, 77(7):527 43 (1999).

Ferrara et al., The Biology of Vascular Endothelial Growth Factor, *Endocrine Reviews*, 18(1):4-25 (1997).

Ferrell et al., Hereditary lymphedema: evidence for linkage and genetic heterogeneity, *Hum. Mol. Gen.*, 7(13):2073-8 (1998).

Fielder et al., Expression of FLT4 and its ligand VEGF-C in Acute Myeloid Leukemia, *Leukemia*, 8:1234-7 (1997). (Abstract).

Finnerty et al., Molecular Cloning g of Murine FLT and FLT4, *Oncogene*, 8(11):2293-98 (1993).

Flanagan et al., The kit Ligand: A Cell Surface Molecule Altered in Steel Mutant Fibroblasts, *Cell*, 63:185-94 (1990).

Folpe et al., Vascular Endothelial Growth Factor Receptor-3 (VEGFR-3): A Marker of Vascular Tumors with Presumed Lymphatic Differentiation, Including Kaposi's Sarcoma, Kaposiform and Dabska-Type Hemangioendotheliomas, and a Subset of Angiosarcomas, *Mod. Pathol.*, 13(2):180-5 (2000).

Fong et al., Role of the Flt-1 receptor tyrosine kinase in regulating the assembly of vascular endothelium, *Nature*, 376(6535):66-70 (1995).

Fournier et al., Interaction with the Phosphotyrosine Binding Domain/Phosphotyrosine Interacting Domain of SHC Is Required for the Transforming Activity of the FLT4/VEGFR3 Receptor Tyrosine Kinase, *J. Biological Chemistry*, 271(22):12956-63 (1996).

Fournier et al., Mutation at Tyrosine Residue 1337 Abrogates Ligand-Dependent Transforming Capacity of the FLT4 Receptor, *Oncogene*, 11:921-31 (1995).

Fuh et al., Requirements for binding and signaling of the kinase domain receptor for vascular endothelial growth factor, *J. Biol. Chem.*, 11197-204 (1998).

Galland et al., Chromosomal Localization of FLT4, a Novel Receptor-Type Tyrosine Kinase Gene, *Genomics*, 13:475-8 (1992).

Galland et al., The FLT4 Gene Encodes a Transmembrane Tyrosine Kinase Related to the Vascular Endothelial Growth Factor Receptor, *Oncogene*, 8(11):1233-40 (1993).

Gasparini et al., Clinical Importance of the Determination of Tumor Angiogenesis in Breast Carcinoma: Much More Than a New Prognostic Tool, *J. Clin. Oncol.*, 13(3):765-82 (1995).

GenBank Accession No. AF014827, Rattus norvegicus vascular endothelial growth factor D (VEGF D) mRNA, deposited by Yamada, Y., dated Aug. 12, 1997.

GenBank Accession No. AJ000185, Homo Sapiens mRNA for vascular endothelial growth factor-D, deposited by Achen, M.G., dated Oct. 7, 2008.

GenBank Accession No. D89628, Mus musculus mRNA for vascular endothelial growth factor D, deposited by Yamada, Y., dated Feb. 7, 1999.

GenBank Accession No. MMU73620, Mus musculus VEGF C mRNA, complete cds., deposited by Kukke, E.

Genbank Accession No. P35916, Galland et al., Vascular Endothelial Frowth Factor Receptor 3 Precursor, dated Oct. 1, 1996.

Genbank Accession X51602 Human flt mRNA for receptor-related tyrosine kinase, deposited by Shibuya, M., dated Oct. 21, 2008.

Genbank Accession X60280 plasmid pLTRpoly, deposited by Maekelae et al., dated Jul. 16, 1996.

Genbank Accession X68203 *H. sapiens* mRNA for FLT4, Class III receptor tyrosine kinase, deposited by Aprelikova, O., dated Sep. 14, 2012.

Gerber et al., Vascular endothelial growth factor induces expression of the antiapoptotic proteins Bcl-2 and A1 in vascular endothelial cells, *J. Biol. Chem.*, 273(21):13313-6 (1998).

Gerber et al., VEGF is required for growth and survival in neonatal mice, *Development*, 126(6):1149-59 (1999).

Gunningham et al., The Short Form of the Alternatively Spliced flt-4 but not Its Ligand Vascular Endothelial Growth Factor C Is Related to Lymph Node Metastasis in Human Breast Cancers, *Clin. Cancer Res.*, 6(11):4278-86 (2000).

Halaby et al., The immunoglobulin fold family: sequence analysis and 3D structure comparisons, *Protein Engineering*, 12(7):563-71 (1999).

Halaby et al., The immunoglobulin superfamily: an insight on its tissular, species, and functional diversity, *J Mol Evol.*, 46(4): 389-400 (1998).

Harlow et al., Antibodies: A Laboratory Manual, pp. 7-25, 72-137, 141-57, 287 & 321-58 (1988).

Hatva et al., Expression of Endothelial Cell-Specific Receptor Tyrosine Kinases and Growth Factors in Human Brain Tumors, *Am. J. Pathol.*, 146:368-78 (1995).

Hatva et al., Vascular Growth Factors and Receptors in Capillary Hemangioblastomas and Hemangiopericytomas, *Am. J. Pathol.*, 148(3):763-75 (1996).

(56) References Cited

OTHER PUBLICATIONS

He et al., Suppression of Tumor Lymphangiogenesis and Lymph Node Metastasis by Blocking Vascular Endothelial Growth Factor Receptor 3 Signaling, *J. Natl. Cancer Inst.*, 94: 819-25 (2002).
Heldin et al., Platelet-Derived Growth Factor: Mechanism of Action and Possible in Vivo Function, *Cell Regulation*, 1:555-66 (1990).
Hewett et al., Coexpression of flt-1, flt-4 and KDR in Freshly Isolated and Cultured Human Endothelial Cells, *Biochem. Biophys. Res. Commun.*, 221:697-702 (1996).
Hirai et al., Expression of Vascular Endothelial Growth Factors (VEGF-A/VEGF-1 and VEGF-C/VEGF-2) in Postmenopausal Uterine Endomatrial Carcinoma, *Gynecol. Oncol.*, 80(2):181-8 (2001).
Holash et al., VEGF-Trap: A VEGF blocker with potent antitumor effects, *Prot. Natl. Acad. Sci. USA*, 99(17):11393-8 (2002).
Hoogenboom, Designing and optimizing library selection strategies for generating high-affinity antibodies, *TIBTECH*, 15:62-70 (1997).
Hu et al., A Novel Regulatory Function of Proteolytically Cleaved VEGF-2 for Vascular Endothelial and Smooth Muscle Cells, *The FASEB J.*, 11:498-504 (1997).
Huang et al., Co-Expression of VEGF-C and its Receptors, VEGFR-2 and VEGFR-3, in Endothelial Cells of Lymphangioma. Implication in Autocrine or Paracrine Regulation of Lymphangioma, *Lab. Invest.*, 81:1729-34 (2001).
Huang et al., The Hematopoietic Growth Factor KL is Encoded by the SI Locus and is the Ligand of the c-kit Receptor, the Gene Product of the W Locus, *Cell*, 63:225-33 (1990).
IMC-1C11, ImClone Systems Incorporated, at www.imclone.com/imc1c11.html (visited Sep. 25, 2001).
International Preliminary Report on Patentability, PCT/AU2014/000114, dated Aug. 18, 2015.
International Search Report and Written Opinion, PCT/AU2014/000114, dated May 20, 2014.
InvivoGen Insight, IgG-Fc Engineering for Therapeutic Use (2006).
Irrthum et al., Congenital hereditary lymphedema caused by a mutation that inactivates VEGFR3 tyrosine kinase., Am. J. Hum. Genet., 67(2):295-301 (2000).
Jacquemier et al., Prognosis of Breast-Carcinoma Lymphagenesis Evaluated by Immunohistochemical Investigation of Vascular-Endothelial-Growth-Factor Receptor 3, *Int. J. Cancer*, 89:69-73 (2000).
Jeltsch, Hyperplasia of Lymphatic Vessels in VEGF-C Transgenic Mice, *Science*, 276:1423-5 (1997).
Jones et al., Angiogenesis and lymphangiogenesis in stage 1 germ cell tumours of the testis, *BJU International*, 86:80-6 (2000).
Joukov et al., A Novel Vascular Endothelial Growth Factor, VEGF-C, is a Ligand for the Flt4 (VEGFR-3) and KDR (VEGFR-2) Receptor Tyrosine Kinases, *EMBO J.*, 15(2):290-8 (1996).
Joukov et al., A Recombinant Mutant Vascular Endothelial Growth Factor c That Has Lost Vascular Endothelial Growth Factor Receptor 2 Binding, Activation, and Vascular Permeability Activities, *J. Biol. Chem.*, 273(12):6599-602 (1998).
Joukov et al., Proteolytic processing regulates receptor specificity and activity of VEGF-C, *EMBO J.*, 16(13):3898-911 (1997).
Jussila et al., Lymphatic Endothelium and Kaposi's Sarcoma Spindle Cells Detected by Antibodies against the Vascular Endothelial Growth Factor Receptor-3, *Cancer Res.*, 58:1599-604 (1998).
Kabashima et al., Overexpression of Vascular Endothelial Growth Factor C is Related to Lymphogenous Metasasis in Early Gastric Carcinoma, *Oncology*, 60(2): 146-50 (2001).
Kadambi et al., Vascular Endothelial Growth Factor (VEGF)-C Differentially Affects Tumor Vascular Function and Leukocyte Recruitment: Role of VEGF-Receptor 2 and Host VEGF-A, *Cancer Res.*, 61(6):2404-8 (2001).
Kaipainen et al., Expression of the FMS-Like Tyrosine Kinase 4 Gene Becomes Restricted to Lymphatic Endothelium During Development, *Proc. Nat'l Acad. Sci. USA*, 92:3566-70 (1995).

Kaipainen et al., The Related FLT4, FLT1, and KDR Receptor Tyrosine Kinases Show Distinct Expression Patterns in Human Fetal Endothelial Cells, *J. Exp. Med.*, 178:2077-88 (1993).
Karkkainen et al., Lymphatic endothelium: a new frontier of metastasis research, *Nat. Cell. Biol.* 4:E2-5 (2002).
Karkkainen et al., Missense Mutations Interfere With VEGFR 3 Signalling in Primary Lymphoedema, *Nat Genet.*, 25(2):153-9 (2000).
Karkkainen et al., Vascular endothelial growth factor receptors in the regulation of angiogenesis and lymphangiogenesis, *Oncogene*, 19(49):5598-605 (2000).
Karpanen et al., Vascular endothelial growth factor C promotes tumor lymphangiogenesis and intralymphatic tumor growth, *Cancer Res.*, 61(5): 1786-90 (2001).
Katritch et al., Diversity and modularity of G protein-coupled receptor structures, *Trends Pharmacol. Sci.*, 33(1):17-27 (2012).
Kendall et al., Inhibition of Vascular Endothelial Cell Growth Factor Activity by an Endogenously Encoded Soluble Receptor, *Proc. Natl. Acad. Sci. USA*, 90:10705-9 (1993).
Kerstens et al., A Novel in Situ Hybridization Signal Amplification Method Based on the Deposition of Biotinylated Tyramine, *J. Histochem. Cytochem.*, 43(4):347-52 (1995).
Kim et al., Inhibition of vascular endothelial growth factor-induced angiogenesis suppresses tumour growth in vivo, *Nature*, 362(6423):841-4 (1993).
Korhonen et al., Enhanced Expression of the tie Receptor Tyrosine Kinase in Endothelial Cells During Neovascularization, *Blood*, 80(10):2548-55 (1992).
Korhonen et al., The Mouse Tie Receptor Tyrosine Kinase Gene: Expression During Embryonic Angiogenesis, *Oncogene* (England), 9(2):395-403 (1994).
Kubo et al., Involvement of vascular endothelial growth factor receptor-3 in maintenance of integrity of endothelial cell lining during tumor angiogenesis, *Blood*, 96(2):546-53 (2000).
Kukk et al., VEGF-C Receptor Binding and Pattern of Expression with VEGFR-3 Suggests a Role in Lymphatic Vascular Development, *Development*, 122:3829-37 (1996).
Kurebayashi et al., Expression of Vascular Endothelial Growth Factor (VEGF) Family Members in Breast Cancer, *Jpn. J. Cancer Res.*, 90(9):977-81 (1999).
Laitinen et al., Adenovirus mediated gene transfer to lower limb artery of patients with chronic critical leg ischemia, *Hum Gene Ther*, 9(10):1481 6 (1998).
Lauria et al., The prognostic value of lymphatic and blood vessel invasion in operable breast cancer, *Cancer*, 76(10):1772 8 (1995).
Lee et al., Vascular Endothelial Growth Factor-Related Protein: A Ligand and Specific Activator of the Tyrosine Kinase Receptor Flt4, *Proc. Natl. Acad. Sci., USA*, 93:1988-92 (1996).
Leu et al., Absence of Functional Lymphatics within a Murine Sarcoma: A Molecular and Functional Evaluation, *Cancer Res*, 60:4324-7 (2000).
Lhotak et al., Characterization of Elk, a Brain-Specific Receptor Tyrosine Kinase, *Mol. Cell. Biol.*, 11:2496-502 (1991).
Lindberg et al. cDNA Cloning and Characterization of eck, an Epithelial Cell Receptor Protein-Tyrosine Kinase in the eph/elk Family of Protein Kinases, *Mol. Cell. Biol.*, 10:6316-24 (1990).
Lyman et al., Molecular Cloning of a Ligand for the flt3/flk-2 Tyrosine Kinase Receptor: A Proliferative Factor for Primitive Hematopoietic Cells, *Cell*, 75:1157-67 (1993).
Lymboussaki et al., Expression of the Vascular Endothelial Growth Factor C Receptor VEGFR-3 in Lymphatic Endothelium of the Skin and in Vascular Tumors, *Amer. J. Pathol.*, 153(2):395-403 (1998).
Makela et al., Plasmid pLTRpoly: a Versatile High-Efficiency Mammalian Expression Vector, *Gene*, 118:293-4 (1992).
Makinen et al., Inhibition of lymphangiogenesis with resulting lymphedema in transgenic mice expressing soluble VEGF receptor-3, *Nat. Med.*, 7(2):199-205 (2001).
Mandriota et al., Vascular Endothelial Growth Factor-C-Mediated Lymphangiogenesis Promotes Tumour Metastasis, *EMBO J.*, 20(5):672-82 (2001).
Marchio et al., Vascular Endothelial Growth Factor-C Stimulates the Migration and Proliferation of Kaposi's Sarcoma Cells, *J. Biol. Chem.*, 274(39):27617-22 (1999).

(56) References Cited

OTHER PUBLICATIONS

Marconcini et al., c-fos-induced growth factor/vascular endothelial growth factor D induces angiogenesis in vivo and in vitro, *Proc. Natl. Acad. Sci. USA*, 96:9671-76 (1999).

Markowska et al., Galectin-3 Protein Modulated Cell Surface Expression and Activation of Vascular Endothelial Growth Factor Receptor 2 in Human Endothelial Cells, *J. Biol. Chem.*, 286:29913-21 (2011).

Matthews et al., A receptor tyrosine kinase cDNA isolated from a population of enriched primitive hematopoietic cells and exhibiting close genetic linkage to c-kit, *Proc. Natl. Acad. Sci. USA*, 88(20):9026-30 (1991).

Matthews et al., A Receptor Tyrosine Kinase Specific to Hematopoietic Stem and Progenitor Cell-Enriched Populations, *Cell*, 65(7):1143-52 (1991).

Mattila, et al., VEGF-C induced lymphangiogenesis is associated with lymph node metastasis in orthotopic MCF-7 tumors, *Int. J. Cancer*, 98:946-51 (2002).

Metzelaar et al., CD63 Antigen, *J. Biol. Chem.*, 266(5):3239-45 (1991).

Mickle je et al., Genotype-Phenotype Relationships in Cystic Fibrosis, *Med. Clin. North Am.*, 84:597-607 (2000).

Mikayama, Molecular Cloning and Functional Expression of a cDNA Encoding Glycosylation-Inhibiting Factor, *Proc. Natl. Acad. Sci. USA*, 90:10056-60 (1993).

Millauer et al., High Affinity VEGF Binding and Developmental Expression Suggest Flk-1 as a Major Regulator of Vasculogenesis and Angiogenesis, *Cell*, 72:835-46 (1993).

Moriyama et al., Immunohistochemical Study of Tumour Angiogenesis in Oral Squamous Cell Carcinoma, *Oral Oncol.*, 33(5):369-74 (1997).

Moroni et al., EGF-R Antisense RNA Blocks Expression of the Epidermal Growth Factor Receptor and Suppresses the Transforming Phenotype of a Human Carcinoma Cell Line, *J. Biol. Chem.*, 267(5):2714-22 (1992).

Mortimer, The Pathophysiology of Lymphedema, *Cancer*, 83(12 Suppl American):2798-802 (1998).

Moshakis et al., Localization of human breast-carcinoma xenografts using antibodies to carcinoembryonic antigen, *Br. J. Cancer*, 43:575-81 (1981).

Mukkala et al., The Synthesis and Use of Activated N-Benzyl Derivatives of Diethylenetriaminetetraacetic Acids: Alternative Reagents for Labeling of Antibodies with Metal Ions, *Annal. Biochem*, 176:319-25 (1989).

Mustonen et al., Endothelial Receptor Tyrosine Kinases Involved in Angiogenesis, *J. Cell Biology*, 129(4):895-8 (1995).

Nathanson et al., Microvessels That Predict Axillary Lymph Node Metastases in Patients With Breast Cancer, *Arch Surg.*, 135(5):586-93 (2000).

Neufeld et al., Vascular endothelial growth factor (VEGH) and its receptors, *FASEB J.*, 13(1):9-22 (1999).

Nicosia, What Is the Role of Vascular Endothelial Growth Factor-Related Molecules in Tumor Angiogenesis? *Am. J. Pathol*, 153(1):11-6 (1998).

Niki et al., Expression of Vascular Endothelial Growth Factor Receptor 3 in Blood and Lymphatic Vessels of Lung Adenocarcinoma, *J. Pathol.*, 193(4):450-7 (2001).

Niki et al., Expression of Vascular Endothelial Growth Factors A, B, C, and D and Their Relationships to Lymph Node Status in Lung Adenocarcinoma, *Clin. Cancer Res.*, 6(6):2431-9 (2000).

Oefner et la., Crystal structure of human platelet-derived growth factor BB, *EMBO J.*, 11:3921-6 (1992).

Oelrichs et al., NYK/FLKA-1: A Putative Receptor Protein Tyrosine Kinase Isolated From E10 Embryonic Neuroepithelium is Expressed in Endothelial Cells of the Developing Embryo, *Oncogene*, 8(1):11-18 (1993).

Oh et al., VEGF and VEGF-C: Specific induction of angiogenesis and lymphangiogenesis in the differentiated avian chorioallantoic membrane, *Devel. Biol.*, 188:96-109 (1997).

Ohta et al., Increased Vascular Endothelial Growth Factor and Vascular Endothelial Growth Factor-C and Decreased NM23 Expression Associated with Microdissemination in the Lymph Nodes in Stage 1 Non-Small Cell Lung Cancer, *J. Thorac Cardiovasc Surg*, 119(4 Pt 1):804-13 (2000).

Ohta, Y., et al., VEGF and VEGF type C play an important role in angiogenesis and lymphangiogenesis in human malignant mesothelioma tumours, *Br. J. Cancer*, 81(1):54-61 (1999).

O'Reilly et al., Angiostatin: A Novel Angiogenesis Inhibitor That Mediates the Suppression of Metastases by a Lewis Lung Carcinoma, *Cell*, 79(2):315-28 (1994).

O'Reilly et al., Endostatin: An Endogenous Inhibitor of Angiogenesis and Tumor Growth, *Cell*, 88(2):277-85 (1997).

Orlandini et al., Identification of a c-fos-induced gene that is related to the platelet-derived growth factor/vascular endothelial growth factor family, *Proc. Natl. Acad. Sci. USA*, 93(21):11675-80 (1996).

Pajusola et al., FLT4 Receptor Tyrosine Kinase Contains Seven Immunoglobulin-Like Loops and is Expressed in Multiple Human Tissues and Cell Lines, *Cancer Research*, 52(20):5738-43 (1992).

Pajusola et al., Signalling Properties of FLT4, a Proteolytically Processed Receptor Tyrosine Kinase Related to Two VEGF Receptors, *Oncogene*, 9:3545-55 (1994).

Pajusola et al., Two Human FLT4 Receptor Tyrosine Kinase Isoforms With Distinct Carboxy Terminal Tails are Produced by Alternative Processing of Primary Transcripts, *Oncogene*, 8:2931-7 (1993).

Pajusola, Cloning and Characterization of a New Endothelial Receptor Tyrosine Kinase FLT4 and Two Novel VEGF-Like Growth Factors VEGF-B and VEGF-C, Molecular/Cancer Biology Laboratory and Department of Pathology, Haartman Institute and Department of Biosciences, Division of Genetics, University of Helsinki, Academic Dissertation, Helsinki (1996).

Parker et al., Identification of the sentinel node in patients with breast cancer, *Radiol. Clin. North Am.*, 38(4):809-23 (2000).

Partanen et al., A Novel Endothelial Cell Surface Receptor Tyrosine Kinase with Extracellular Epidermal Growth Factor Homology Domains, *Mol. Cell. Biol.*, 12(4):1698-707 (1992).

Partanen et al., Putative Tyrosine Kinases Expressed in K-562 Human Leukemia Cells, *Proc. Nat'l Acad. Sci. USA*, 87(22):8913-7 (1990).

Partanen, T.A., et al., Lack of Lymphatic Vascular Specificity of Vascular Endothelial Growth Factor Receptor 3 in 185 Vascular Tumors, *Cancer*, 86(11): 2406-12 (1999).

Patent Cooperation Treaty Search Report for PCT/US1999/23525, dated Mar. 20, 2000.

Pavlakovic et al., Soluble VEGFR-2: an antilymphangiogenic variant of VEGF receptors, *Ann. N Y Acad. Sci.*, 1207(Suppl 1):E7-15 (2010).

Pepper, Lymphangiogenesis and Tumor Metastasis: Myth or Reality?, *Clinical Cancer Res.*, 7:462-8 (2001).

Peters et al., Vascular Endothelial Growth Factor Receptor Expresson During Embryogenesis and Tissue Repair Suggests a Role in Endothelial Differentiation and Blood Vessel Growth, *Proc. Nat'l Acad. Sci. USA*, 90:8915-9 (1993).

Pietersz et al., Antibody Conjugates for the Treatment of Cancer, *Immunological Reviews*, 129:57-80 (1992).

Plückthun et al., New protein engineering approaches to multivalent and bispecific antibody fragments, *Immunotechnology*, 3:83-105 (1997).

Poncz et al., Cloning and Characterization of Platelet Factor 4 cDNA Derived From a Human Erythroleukemic Cell Line, *Blood*, 69(1):219-23 (1987).

Popkov et al., Human/mouse cross-reactive anti-VEGF receptor 2 recombinant antibodies selected from an immune b9 allotype rabbit antibody library, *J. Immunol. Meth.*, 288(1-2):149-64 (2004).

Rader et al., Phage display of combinatorial antibody libraries, *Curr. Opin. Biotech.*, 8:503-8 (1997).

Reedijk et al., Tyr721 Regulates Specific Binding of the CSF-1 Receptor Kinase Insert to P1 3'-Kinase SH2 Domains: a Model for SH2-Mediated Receptor-Target Interactions, *EMBO J.*, 11(4):1365-72 (1992).

(56) References Cited

OTHER PUBLICATIONS

Relf, M. et al., Expression of the Angiogenic Factors Vascular Endothelial Cell Growth Factor, Acidic and Basic Fibroblast Growth Factor, Tumor Growth Factor β-1, Platelet-derived Endothelial Cell Growth Factor, Placenta Growth Factor, and Pleiotrophin in Human Primary Breast Cancer and Its Relation to Angiogenesis, *Cancer Research*, 57:963-9 (1997).
Renner et al., Tumor Therapy by Immune Recruitment with Bispecific Antibodies, *Immunological Reviews*, 145:179-209 (1995).
Roeckl et al., Differential binding characteristics and cellular inhibition by soluble VEGF receptors 1 and 2, *Exp. Cell Res.*, 241(1):161-70 (1998).
Rosnet et al., Isolation and Chromosomal Localization of a Novel FMS-Like Tyrosine Kinase Gene, *Oncogene*, 6(9):1641-50 (1991).
Rosnet et al., Murine Flt3, a Gene Encoding a Novel Tyrosine Kinase Receptor of the PDFR/CSF1R Family, *Genomics*, 9:380-85 (1991).
Saaristo et al., Vascular Endothelial Growth Factor-C and its Receptor VEGFR-3 in the Nasal Mucosa and in Nasopharyngeal Tumors, *Am. J. Pathology*, 157(1):7-14 (2000).
Salven et al., Vascular Endothelial Growth Factors VEGF-B and VEGF-C Are Expressed in Human Tumors, *Amer. J. Pathol.*, 153(1):103-8 (1998).
Sato et al., Regulatory mechanism of 92 kDa type IV collagenase gene expression which is associated with invasiveness of tumor cells, *Oncogene*, 8:395-405 (1993).
Satoh et al., Regional Localization of the Human c-ros-1 on 6q22 and flt on 13q12, *Jpn. J. Cancer Res.*, 78:772-75 (1987).
Schlessinger, Cell Signaling by Receptor Tyrosine Kinases, *Cell*, 103(2): 211-25 (2000).
Schoppmann et al., Lymphatic Vessels and Lymphangiogenesis in Femal Cancer: Mechanisms, Clinical Impact and Possible Implications for Anti-Lymphangiogenic Therapies (Review), *Oncology Reports*, 9:455-66 (2001).
Scott et al., Laboratory-Clinic Interface: Current approaches to targeting cancer using antiangiogenesis therapies, *Cancer Treatment Reviews*, 20:393-412 (1994).
Segal et al., Alternative Triggering Molecules and Single Chain Bispecific Antibodies, *J. Hematother.*, 4:377-82 (1995).
Shibuya et al., Differential roles of vascular endothelial growth factor receptor-1 and receptor-2 in angiogenesis, *J. Biochem. Mol. Biol.*, 39(5):469-78 (2006).
Shibuya et al., Nucleotide Sequence and Expression of a Novel Human Receptor-Type Tyrosine Kinase Gene (flt) Closely Related to the fms Family, *Oncogene*, 5:519-24 (1990).
Shibuya, Role of VEGF-FLT Receptor System in Normal and Tumor Angiogenesis, *Adv. Can. Res.*, 67:281-316 (1995).
Shinkai et al., Mapping of the sites involved in ligand association and dissociation at the extracellular domain of the kinase insert domain-containing receptor for vascular endothelial growth factor, *J. Biol. Chem.*, 273:31283-8 (1998).
Shushanov et al., VEGFc and VEGFR3 Expression in Human Thyroid Pathologies, *Int. J. Cancer*, 86:47-52 (2000).
Siemeister, et al., Two independent mechanisms essential for tumor angiogenesis: inhibition of human melanoma xenograft growth by interfering with either the vascular endothelial growth factor receptor pathway or the Tie-2 pathway, *Cancer Res.* 59:3185-91 (1999).
Skobe et al., Concurrent Induction of Lymphangiogenesis, Angiogenesis, and Macrophage Recruitment by Vascular Endothelial Growthh Factor-C in Melanoma, *Am. J. Pathol.*, 159:893-903 (2001).
Skobe et al., Induction of Tumor Lymphangiogenesis by VEGF-C Promotes Breast Cancer Metastasis, *Nat. Med.*, 7(2):192-8 (2001).
Skobe et al., Vascular Endothelial Growth Factor-C (VEGF-C) and its Receptors KDR and flt-4 are Expressed in AIDS-Associated Kaposi's Sarcoma, *J. Invest. Dermatology*, 113:1047-53 (1999).
Sotos et al., *Statistics Education Research J.*, 8(2):33-55 (2009).

Sowter et al., Expression and Localization of the Vascular Endothelial Growth Factor Family in Ovarian Epithelial Tumors, *Lab. Invest.*, 77(6):607-14 (1997).
Stacey et al., SVpoly: A Versatile Mammalian Expression Vector, *Nucl. Acids Res.*, 18(9):2829 (1990).
Stacker et al., Biosynthesis of vascular endothelial growth factor-d involves proteolytic processing with generates non-covalent homodimers, *J. Biol. Chem.*, 274:32127 (1999).
Stacker, VEGF-D Promotes the Metastatic Spread of Tumor Cells Via the Lymphatics, *Nat. Med.*, 7(2): 186-91 (2001).
Stohrer et al., Oncotic Pressure in Solid Tumors is Elevated, *Cancer Res.*, 60:4251-5 (2000).
Sundström et al., Establishment and Characterization of a Human Histiocytic Lymphoma Cell Line (U-937), *Int. J. Cancer*, 17:565-77 (1976).
Taipale, J. et al., Vascular Endothelial Growth Factor Receptor 3, *Curr Top Microbiol. Immunol.*, 237:85 96 (1999).
Tanaka et al., DNA sequence encoding the amino-terminal region of the human c-src protein: implications of sequence divergence among src-type kinase oncogenes, *Mol. Cell Biol.*, 7(5):1978-83 (1987).
Tang et al., Overexpression of Lymphangiogenesis Growth Factor VEGF-C in Human Pancreatic Cancer, *Pancreas*, 22(3): 285-92 (2001).
Tekmal et al., A novel in vitro and in vivo breast cancer model for testing inhibitors of estrogen biosynthesis and its action using mammary tumor cells with an activated int-5/aromatase gene, *Cancer Letters*, 118(1):21-8 (1997).
Terman et al., Identification of a new endothelial cell growth factor receptor tyrosine kinase, *Oncogene*, 6(9):1677-83 (1991).
Terman et al., Identification of the KDR Tyrosine Kinase as a Receptor for Vascular Endothelial Cell Growth Factor, *Biochem & Biophys. Res. Comm.*, 187(3):1579-86 (1992).
Thurston et al., Leakage resistant blood vessels in mice transgenically overexpressing angiopoietin 1, *Science*, 286(5449):2511-4 (1999).
Tischer et al., Vascular endothelial growth factor: a new member of the platelet-derived growth factor gene family, *Biochem. Biophys. Res. Commun.*, 165(3):1198-206 (1989).
Tsurusaki et al., Vascular endothelial growth factor-C expression in human prostatic carcinoma and its relationship to lymph node metastasis, *Br. J. Cancer*, 801(2):309-13 (1999).
Ullrich et al., Signal Transduction by Receptors with Tyrosine Kinase Activity, *Cell*, 61:203-12 (1990).
Valtola et al., VEGFR-3 and Its Ligand VEGF-C Are Associated with Angiogenesis in Breast Cancer, *Am. J. Pathol.*, 154(5):1381-90 (1999).
Veikkola et al., Regulation of Angiogenesis Via Vascular Endothelial Growth Factor Receptors, *Cancer Res.*, 60(2):203-12 (2000).
Veikkola et al., Signaling via vascular endothelial growth receptor-3 is sufficient for lymphangiogenesis in transgenic mice, *EMBO J.*, 6:1223-31 (2001).
Wang, Signal Transduction in Human Hematopoietic Cells by Vascular Endothelial Growth Factor Related Protein, a Novel Ligand for the FLT4 Receptor, *Blood*, 90(9):3507-15 (1997).
Wartiovaara et al., Peripheral Blood Platelets Express VEGF-C and VEGF Which are Released during Platelet Activation, *Thromb. Haemost.*, 80:171-5 (1998).
Weidner et al., Tumor Angiogenesis: A New Significant and Independent Prognostic Indicator in Early-Stage Breast Carcinoma, *J. Natl. Cancer Inst.*, 84(24):1875-87 (1992).
Weismann et al., Crystal structure at 1.7 A resolution of VEGF in complex with domain 2 of the Flt-1 receptor, *Cell*, 91:695-704 (1997).
Weismann et al., Ligand-binding sites in Ig-like domains of receptor tyrosine kinases, *J. Molec. Med.*, 78:247-60 (2000).
Wen et al., New Differentiation Factor: A Transmembrane Glycoprotein Containing an EGF Domain and an Immunoglobulin Homology Unit, *Cell*, 69:559-72 (1992).

(56) References Cited

OTHER PUBLICATIONS

Weninger et al., Expression of Vascular Endothelial Growth Factor Receptor-3 and Podoplanin Suggests a Lymphatic Endothelial Cell Origin of Kaposi's Sarcoma Tumor Cells, *Lab. Invest.*, 79(2):243-51 (1999).

Williams et al., The Immunoglobin Superfamily—Domains for Cell Surface Recognition, *Ann. Rev. Immunol.*, 6:381-405 (1988).

Witmer et al., VEGFR-3 in adult angiogenesis, *J. Path.* 195:490-7 (2001).

Witte et al., Lymphangiogenesis: Mechanisms, Significance and Clinical Implications, in Regulation of Angiogenesis (eds. Goldberg, I.D. & Rosen, E. M.) 65-112 (birkhauser Verlag, Basel, Switzerland) 1997.

Witzenbichler et al., Vascular Endothelial Growth Factor-C (VEGF-C/VEGF-2) Promotes Angiogenesis in the Setting of Tissue Ischemia, *American Journal of Pathology*, 153(2):381-94 (1998).

Yamaguchi et al., Flk-1, an Flt-Related Tyrosine Kinase is an Early Marker for Endothelial Cell Precursors, *Development*, 118:489-98 (1993).

Yan et al., Two-Amino Acid Molecular Switch in an Epithelial Morphogen that Regulates Binding to two Distinct Receptors, *Science*, 290:523-7 (2000).

Yarden et al., Human Proto-Oncogene c-kit: A New Cell Surface Receptor Tyrosine Kinase for an Unidentified Ligand, *EMBO J.*, 6(11):3341-3351 (1987).

Yokoyama et al., Prognostic Significance of Vascular Endothelial Growth Factor and Its receptors in Endometrial Carcinoma, *Gyn. Oncol.*, 77:413-8 (2000).

Yonemura et al., Lymphangiogenesis and the Vascular Endothelial Growth Factor Receptor (VEGFR)-3 in Gastric Cancer, *Eur. J. Cancer*, 37(7):918-23 (2001).

Yonemura et al., Role of Vascular Endothelial Growth Factor C Expression in the Development of Lymph Node Metastasis in Gastric Cancer, *Clin. Cancer Res.*, 5:1823-9 (1999).

Yu et al., Soluble vascular endothelial growth factor decoy receptor FP3 exerts potent antiangiogenic effects, *Molec. Ther.*, 20:938-47 (2012).

FIG. 2B

| | VGX-300-07 VC | VGX-301-N2 VC | VGX-300-07 VD | VGX-301-N2 VD |
|---|---|---|---|---|
| BOTTOM | 0.06295 | 0.08009 | 0.04496 | 0.04462 |
| TOP | 2.660 | 2.677 | 2.062 | 2.178 |
| LOGEC50 | 1.764 | 1.469 | 2.703 | 2.021 |
| HILLSLOPE | 1.091 | 1.057 | 0.9355 | 0.9812 |
| EC50 | 58.05 | 29.45 | 504.5 | 105.0 |
| SPAN | 2.597 | 2.597 | 2.017 | 2.133 |

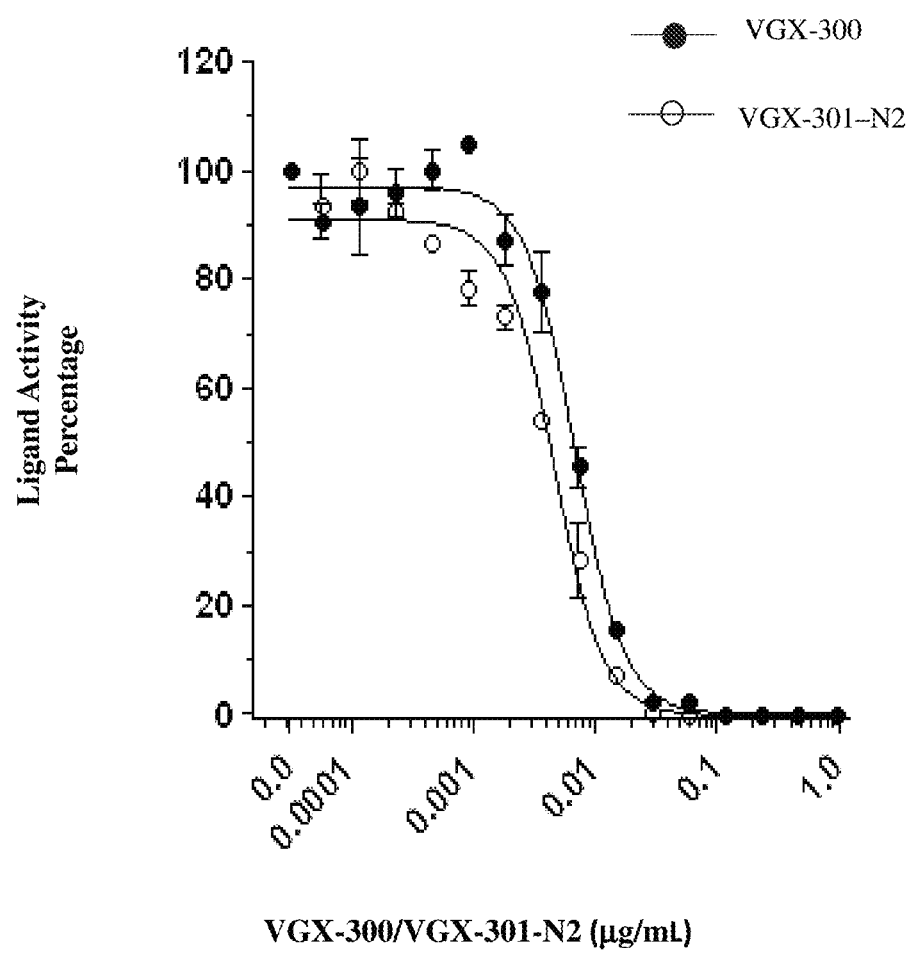

VEGFR-3 LIGAND BINDING MOLECULES AND USES THEREOF

FIELD OF THE INVENTION

This invention relates generally to modulation of vessel growth, especially in ophthalmology and oncology.

SEQUENCE LISTING

The electronic sequence listing forms part of the description.

BACKGROUND

The vascular endothelial growth factor (VEGF) proteins and their receptors (VEGFRs) play important roles in both vasculogenesis, the development of the embryonic vasculature from early differentiating endothelial cells, angiogenesis, the process of forming new blood vessels from pre-existing ones, and lymphangiogenesis, the process of forming new lymph vessels. The platelet derived growth factor (PDGF) proteins and their receptors (PDGFRs) are involved in regulation of cell proliferation, survival and migration of several cell types.

Dysfunction of the endothelial cell regulatory system is a key feature of cancer and various diseases associated with abnormal vasculogenesis, angiogenesis and lymphangiogenesis.

Angiogenesis occurs in embryonic development and normal tissue growth, repair, and regeneration, the female reproductive cycle, the establishment and maintenance of pregnancy, the repair of wounds and fractures. In addition to angiogenesis which takes place in the healthy individual, angiogenic events are involved in a number of pathological processes, notably tumor growth and metastasis, and other conditions in which blood vessel proliferation, especially of the microvascular system, is increased, such as diabetic retinopathy, psoriasis and arthropathies. Inhibition of angiogenesis is useful in preventing or alleviating these pathological processes or slowing progression of them.

Although therapies directed to blockade of VEGF/PDGF signaling through their receptors have shown promise for inhibition of angiogenesis and tumor growth, there remains a need for new or improved compounds and therapies for the treatment of such diseases.

SUMMARY OF THE INVENTION

The present invention relates to novel compositions and methods of use thereof for the inhibition of aberrant angiogenesis, lymphangiogenesis or both, and inhibition of other effects of Vascular Endothelial Growth Factor-C (VEGF-C) and Vascular Endothelial Growth Factor-D (VEGF-D), each of which is able to bind at least one growth factor receptor tyrosine kinase (i.e., VEGFR-2 or VEGFR-3) and stimulate phosphorylation of the same. The compositions of the invention include ligand binding molecules that bind one or both of human VEGF-C and human VEGF-D. In some embodiments, the ligand binding molecule comprises a polypeptide, e.g., a fragment of a growth factor receptor tyrosine kinase extracellular domain (ECD). The fragment may vary from the wildtype sequence in ways that do not eliminate growth factor binding, and the fragment preferably is engineered in ways described herein to improve its properties as a therapeutic for administration to subjects/patients in need.

The invention also provides nucleic acids encoding such ligand binding molecules. The nucleic acids are useful for expressing the polypeptide ligand binding molecules and also useful, in some embodiments, as a therapeutic for achieving expression of the polypeptide ligand binding molecules in vivo, in a biologically active form.

Administration of the compositions comprising a ligand binding molecule described herein (or polynucleotide encoding it) to patients in need thereof inhibits growth factor stimulation of VEGF receptors (e.g., inhibits phosphorylation of the receptors) and thereby inhibits biological responses mediated through the receptors including, but not limited to, VEGFR-mediated angiogenesis, lymphangiogenesis or both.

VEGF-C and D bind with high affinity to, and stimulate phosphorylation of, at least one VEGF receptor (or receptor heterodimer) selected from VEGFR-2 and VEGFR-3. This statement refers to well-known properties of the growth factors toward their cognate receptors, and is not meant as a limiting feature per se of the ligand binding molecules of the invention. However, preferred ligand binding molecules of the invention do more than simply bind their target growth factors. A preferred ligand binding molecule also inhibits the growth factor(s) to which it binds from stimulating phosphorylation of at least one (and preferably all) of the receptor tyrosine kinases to which the growth factor(s) bind. Stimulation of tyrosine phosphorylation is readily measured using in vitro cell-based assays and anti-phosphotyrosine antibodies. Because phosphorylation of the receptor tyrosine kinases is an initial step in a signaling cascade, it is a convenient indicator of whether the ligand binding molecule is capable of inhibiting growth factor-mediated signal transduction that leads to cell migration, cell growth and other responses. A number of other cell-based and in vivo assays can be used to confirm the growth factor neutralizing properties of ligand binding molecules of the invention.

Ligand binding molecules that are "specific" for a particular growth factor are ligand binding molecules that specifically recognize an active form of the growth factor (e.g., a form found circulating in the body). Preferably, the ligand binding molecules specifically bind other forms of the growth factors as well. By way of example, VEGF-C (and VEGF-D) is translated as a prepro-molecule with extensive amino-terminal and carboxy-terminal propeptides that are cleaved to yield a "fully processed" form of VEGF-C (or VEGF-D) that binds and stimulates VEGFR-2 and VEGFR-3. Ligand binding molecules specific for VEGF-C (or VEGF-D) bind to at least the fully processed form of VEGF-C (or VEGF-D), and preferably also bind to partially processed forms and unprocessed forms.

In one aspect, described herein the ligand binding molecule is a purified or isolated ligand binding polypeptide comprising a first amino acid sequence having at least 80%, or at least 85%, or at least 90%, or at least 92%, or at least 95%, or at least 96%, or at least 97%, or at least 98%, or at least 99% identity to the sequence of amino acids defined by positions 47-115 of SEQ ID NO: 2 or positions 25-115 of SEQ ID NO: 2, with the proviso that positions of the polypeptide corresponding to positions 104-106 of SEQ ID NO: 2 are not identical to N-X-S or N-X-T (X representing any amino acid), wherein the polypeptide binds to at least one ligand polypeptide selected from the VEGF or PDGF families of growth factors, such as human VEGF-A (VEGF), VEGF-B, VEGF-C, VEGF-D, PlGF, PDGF-A, PDGF-B, PDGF-C, and PDGF-D. SEQ ID NO: 2 contains an amino acid sequence for human VEGFR-3, with positions 1-24 of SEQ ID NO: 2 corresponding to a putative signal peptide and position 25 onwards of SEQ ID NO: 2 corresponding to a putative mature form of the receptor lacking a putative signal peptide. The foregoing segments of SEQ ID NO: 2 roughly correspond to or include the first immunoglobulin-like domain of the ECD of human VEGFR-3 ("D1 of VEGFR-3"). Constructs that comprise additional Ig-like domains of VEGFR-3 or other receptors, attached in a manner that result in a ligand binding polypeptide, are specifically contemplated, and constructs that bind different ligands are constructed by varying the receptor components used to make the ligand binding polypeptide. In some variations, the ligand binding polypeptide is based primarily on the extracellular domain of VEGFR-3, and in other embodiments, the ligand binding polypeptide is based on a fusion of segments of other receptor tyrosine kinases, such as VEGFR-1 and/or VEGFR-2 and/or PDGFR-α and/or PDGFR-β. In embodiments based primarily on VEGFR-3, the at least one ligand is a natural ligand for VEGFR-3, such as a VEGF-C or a VEGF-D polypeptide.

In some embodiments, the ligand binding polypeptide comprises a second amino acid sequence at least 80%, or at least 85%, or at least 90%, or at least 92%, or at least 95%, or at least 96%, or at least 97%, or at least 98%, or at least 99% identical to the sequence of amino acids defined by positions 154-210 of SEQ ID NO:2 or positions 248-314 of SEQ ID NO:2, wherein the N-terminal residue of the second amino acid sequence is connected to the C-terminal residue of the first amino acid sequence either directly or via a spacer, wherein the polypeptide binds to at least one ligand polypeptide selected from the VEGF or PDGF families of growth factors, such as human VEGF-A (VEGF), VEGF-B, VEGF-C, VEGF-D, PlGF, PDGF-A, PDGF-B, PDGF-C, and PDGF-D. The sequence of amino acids defined by positions of the polypeptide corresponding to positions 154-210 roughly corresponds to or includes the second immunoglobulin-like domain of the ECD of human VEGFR-3 ("D2 of VEGFR-3"). The sequence of amino acids defined by positions of the polypeptide corresponding to positions 248-314 roughly corresponds to or includes the third immunoglobulin-like domain of the ECD of human VEGFR-3 ("D3 of VEGFR-3"). Where the second amino acid sequence comprises a sequence of amino acids roughly corresponding to or including D2 of VEGFR-3, it is preferred that the ligand binding polypeptide comprises a third amino acid sequence at least 80%, or at least 85%, or at least 90%, or at least 92%, or at least 95%, or at least 96%, or at least 97%, or at least 98%, or at least 99% identical to the sequence of amino acids defined by positions 248-314 of SEQ ID NO:2, wherein the N-terminal residue of the third amino acid sequence is connected to the C-terminal residue of the second amino acid sequence either directly or via a spacer, wherein the polypeptide binds to at least one ligand polypeptide selected from the VEGF or PDGF families of growth factors, such as human VEGF-A (VEGF), VEGF-B, VEGF-C, VEGF-D, PlGF, PDGF-A, PDGF-B, PDGF-C, and PDGF-D. In other words, in embodiments where the ligand binding polypeptide comprises amino acid sequences roughly corresponding to or including the D1 and D2 of VEGFR-3, it is preferred that the ligand binding polypeptide also comprises an amino acid sequence roughly corresponding to or including the D3 of VEGFR-3.

In embodiments where the ligand binding polypeptide comprises amino acid sequences roughly corresponding to two or more component domains of VEGFR-3, the component domains may be connected directly to each other or may be connected via one or more spacers. Preferably, the component domains are connected by one or more spacers. In one embodiment, the spacer comprises one or more peptide sequences between the component domains which is (are) between 1-100 amino acids, preferably 1-50 amino acids in length. In one embodiment, the spacer between two component domains substantially consists of peptide sequences naturally connected to the component domain in native VEGFR-3.

In embodiments where the ligand binding polypeptide comprises amino acid sequences roughly corresponding to or including contiguous component domains of VEGFR-3 (for example, D1-D2 or D1-D2-D3), the component domains are connected via one or more spacers comprising one or more peptide sequences between the component domains which is (are) between 1-100 amino acids, preferably 1-50 amino acids in length. In one embodiment, the spacer between two component domains substantially consists of peptide sequences corresponding to those connecting the respective contiguous component domains in the native VEGFR-3. In some embodiments, the spacer between two contiguous component domains comprises an amino acid sequence at least 80%, or at least 85%, or at least 90%, or at least 92%, or at least 95%, or at least 96%, or at least 97%, or at least 98%, or at least 99% identical to the sequence of amino acids that connects the contiguous domains in the native VEGFR-3.

In one embodiment, where the ligand binding polypeptide comprises amino acid sequences roughly corresponding to or including the D1 and D2 of VEGFR-3, the component domains D1 and D2 are connected via a spacer amino acid sequence having at least 80%, or at least 85%, or at least 90%, or at least 92%, or at least 95%, or at least 96%, or at least 97%, or at least 98%, or at least 99% identity to the sequence of amino acids defined by positions 116-153 of SEQ ID NO: 2. Where the ligand binding polypeptide comprises amino acid sequences roughly corresponding to or including the D1, D2 and D3 of VEGFR-3, the component domains D2 and D3 are connected via a spacer amino acid sequence having at least 80%, or at least 85%, or at least 90%, or at least 92%, or at least 95%, or at least 96%, or at least 97%, or at least 98%, or at least 99% identity to the sequence of amino acids defined by positions 211-247 of SEQ ID NO: 2.

In some embodiments, the purified or isolated ligand binding polypeptide comprises an amino acid sequence at least 80%, or at least 85%, or at least 90%, or at least 92%, or at least 95%, or at least 96%, or at least 97%, or at least 98%, or at least 99% identical to the sequence of amino acids defined by positions 47-210 of SEQ ID NO: 2, or positions 25-210 of SEQ ID NO: 2, or positions 47-314 of SEQ ID NO: 2, or positions 25-314 of SEQ ID NO: 2, or positions 47-752 or 47-775 of SEQ ID NO: 2, or positions 25-752 or 25-775 of SEQ ID NO: 2, with the proviso that positions of the polypeptide corresponding to positions 104-106 of SEQ ID NO: 2 are not identical to N-X-S or N-X-T, wherein the polypeptide binds to at least one ligand polypeptide selected from human VEGF-A, VEGF-C, VEGF-C, VEGF-D and PlGF. In one variation, the amino acid corresponding to position 104 of SEQ ID NO: 2 is deleted and replaced with another amino acid (such as glutamine, aspartate, glutamate, arginine and lysine). Positions 47-210 include the first two immunoglobulin-like domains of the human VEGFR-3 ECD, as well as VEGFR-3 ECD sequence between the first two Ig-like motifs. Positions 47-314 include the first three immunoglobulin-like domains of the human VEGFR-3 ECD, as well as VEGFR-3 ECD sequence between these Ig-like motifs.

More generally, a ligand binding polypeptide of the invention comprises an amino acid sequence at least 80%, or at least 85%, or at least 90%, or at least 92%, or at least 95%, or at least 96%, or at least 97%, or at least 98%, or at least 99% identical to a fragment of the VEGFR-3 amino acid sequence set forth in SEQ ID NO: 2, wherein the amino terminus of the fragment is any amino acid selected from positions 25, 26, 27, 28, 29, 30, 31, 32, 33, 34, 35, 36, 37, 38, 39, 40, 41, 42, 43, 44, 45, 46, 47, 48, 49, and 50 of SEQ ID NO: 2; and wherein the carboxy terminus of the fragment is any amino acid selected from positions 110-775 of SEQ ID NO: 2 (e.g., positions 110, 111, 112, 113, 114, 115, 116, . . . 747, 748, 749, 750, 751, 752, 753, 754, 755, 756, 757, 758, 759, 760, 761, 762, 763, 764, 765, 766, 767, 768, 769, 770, 771, 772, 773, 774, 775), with the proviso that positions of the polypeptide corresponding to positions 104-106 of SEQ ID NO: 2 are not identical to N-X-S or N-X-T. For reasons that will be readily apparent from the description herein, the variation permitted is not variation that introduces new glycosylation sequons that are not found in wildtype VEGFR-3.

In another aspect, described herein the ligand binding molecule is a purified or isolated ligand binding polypeptide that comprises an amino acid sequence that is identical to the sequence of amino acids defined by positions of the polypeptide corresponding to positions 47-115 of SEQ ID NO: 2, 47-210 of SEQ ID NO: 2, 47-314 of SEQ ID NO: 2, 47-752 or 47-775 of SEQ ID NO: 2, or 25-752 or 25-775 of SEQ ID NO: 2, with the proviso that positions of the polypeptide corresponding to positions 104-106 of SEQ ID NO: 2 are not identical to N-X-S or N-X-T. In one variation, the amino acid corresponding to position 104 of SEQ ID NO: 2 is deleted and replaced with another amino acid (such as glutamine, aspartate, glutamate, arginine and lysine).

In another aspect, described herein the ligand binding molecule is a purified or isolated ligand binding polypeptide comprising an amino acid sequence having at least 80%, or at least 85%, or at least 90%, or at least 92%, or at least 95%, or at least 96%, or at least 97%, or at least 98%, or at least 99% identity to the sequence of amino acids defined by positions 47-115 of SEQ ID NO: 2, wherein positions of the polypeptide corresponding to positions 104-106 of SEQ ID NO: 2 are a putative VEGFR-3 glycosylation sequon, and wherein said putative glycosylation sequon is eliminated from the amino acid sequence of the ligand binding polypeptide. The term "eliminated" as used in this context means an alteration of the primary amino acid sequence in at least one position (by substitution, deletion or insertion) to destroy the N-X-T sequon motif.

The invention also includes multimeric ligand binding constructs comprising two or more ligand binding molecules as described herein, covalently or non-covalently attached to each other to form a dimeric or multimeric structure. In some variations, the attachment occurs between the VEGFR-3-like sequences of the ligand binding polypeptides; in other variations, the attachment occurs between heterologous polypeptides attached to one or both of the VEGFR-3 like sequences.

Reference herein to a ligand binding molecule or ligand binding polypeptide described herein includes reference to variants thereof as defined above with the proviso that such ligand binding polypeptides or molecules (whether monomeric, dimeric or a higher multimer) contains at least an Ig-like motif similar or identical to Ig-like motif 1 of VEGFR-3 (e.g., about 47-115 of SEQ ID NO: 2), with the proviso that positions of the polypeptide corresponding to positions 104-106 of SEQ ID NO: 2 (which represent an N-linked glycosylation sequon in the native VEGFR-3 sequence) are not identical to N-X-S or N-X-T.

In another aspect, described herein is a ligand binding molecule which is an isolated or purified ligand binding polypeptide comprising the first immunoglobulin-like domain of a VEGFR-3ΔN2 polypeptide. As used herein, the term "VEGFR-3ΔN2 polypeptide" refers to a polypeptide having at least 95% identity to the sequence of amino acids defining the ECD of human VEGFR-3, with the proviso that the portion of the polypeptide's sequence corresponding to the second putative glycosylation sequon, NDT, is mutated such that it no longer fits the N-X-S/T SEQUON motif, e.g., due to substitution at one of the positions. In some embodiments, the purified polypeptide comprises the first two immunoglobulin-like domains of the VEGFR-3ΔN2 polypeptide, and preferably includes the VEGFR-3 sequence between those domains. In some embodiments, the purified polypeptide comprises the first three immunoglobulin-like domains of the VEGFR-3ΔN2 polypeptide, and preferably includes the VEGFR-3 sequence between those domains.

In yet another aspect, described herein is a ligand binding molecule which is a polypeptide comprising an ECD fragment of human VEGFR-3, fused to a fusion partner wherein the amino acid sequence of the ECD fragment of VEGFR-3 is modified from wildtype VEGFR-3 to eliminate the second putative N-linked glycosylation sequon of wildtype VEGFR-3, wherein the polypeptide is soluble in human serum and binds human VEGF-C or human VEGF-D; and wherein the fusion partner improves solubility or serum half-life of the ECD fragment (e.g., compared to an identical fragment that is not fused to a fusion partner). In some embodiments, the fusion partner is a heterologous polypeptide. In some embodiments, the ligand binding polypeptide or ligand binding molecule binds human VEGF-C or human VEGF-D. In some embodiments, the ligand binding polypeptide or ligand binding molecule inhibits VEGF-C- or VEGF-D-binding to VEGFR-3 or inhibits VEGF-C- or VEGF-D-mediated stimulation of VEGFR-3 in a cell expressing VEGFR-3 on its surface. The inhibition of stimulation can be demonstrated, for example, by measuring receptor phosphorylation, or by measuring cellular growth in vitro or in vivo, or by measuring vessel growth or other tissue-level changes in vivo.

The ligand binding molecule preferably binds human VEGF-C with a $K_d$ of about 1 nM or less (e.g., 500 pM, 400 pM, 300 pM, 200 pM, 100 pM, 50 pM, 10 pM or less). The ligand binding molecule preferably binds human VEGF-D with a $K_d$ of about 5 nM or less (e.g., 2 nM, 1 nM, 500 pM, 400 pM, 300 pM, 200 pM, 100 pM, 50 pM, 10 pM or less).

In another aspect, the purified or isolated ligand binding molecule comprises amino acids 22-290 of SEQ ID NO: 3, amino acids 23-290 of SEQ ID NO: 3, amino acids 23-537 of SEQ ID NO: 3 or amino acids 22-537 of SEQ ID NO: 3. In still other variations, the molecule comprises an amino acid sequence at least 80%, or at least 85%, or at least 90%, or at least 92%, or at least 95%, or at least 96%, or at least 97%, or at least 98%, or at least 99% identical to either of the foregoing sequences, with the proviso that the sequence of the polypeptide that corresponds to (aligns with) the VEGFR-3 N2 sequon is not a glycosylation sequence.

As described herein, ligand binding molecules can be chemically modified (e.g., glycosylation, pegylation, etc.) to impart desired characteristics, while maintaining their specific growth factor binding properties. Ig-like domains I-III of VEGFR-3 comprises five putative N-glycosylation sites (referred to herein as N1, N2, N3, N4 and N5 sequons of VEGFR-3, respectively). N1 corresponds to amino acids 33-35 of SEQ ID NO: 2; N2 corresponds to amino acids 104-106 of SEQ ID NO: 2; N3 corresponds to amino acids 166-168 of SEQ ID NO: 2; N4 corresponds to amino acids 251-253 of SEQ ID NO: 2 and N5 corresponds to amino acids 299-301 of SEQ ID NO: 2. In some embodiments, a ligand binding molecule described herein comprises a modification in the N2 sequon of the molecule. For example, in some embodiments, the amino acid in the ligand binding molecule corresponding to position 104 of SEQ ID NO: 2 is deleted and replaced with another amino acid. Conservative substitutions are preferred. In some embodiments, the amino acid corresponding to position 104 of SEQ ID NO: 2 is deleted and replaced with an amino acid selected from the group consisting of glutamine, aspartate, glutamate, arginine and lysine. In embodiments where the N2 sequon of SEQ ID NO: 2 is modified as described above, the N1, N3, N4 and N5 sequons of SEQ ID NO: 2 are preferably unaltered in terms of amino acid sequence.

As described herein, ligand binding molecules can be connected to a fusion partner either directly or via a linker. A fusion partner may be any heterologous component that enhances the functionality of the ligand binding molecule. An exemplary peptide fusion partner comprises an immunoglobulin constant domain (Fc) fragment. In some embodiments, the immunoglobulin constant fragment comprises an amino acid sequence having at least 80%, or at least 85%, or at least 90%, or at least 92%, or at least 95%, or at least 96%, or at least 97%, or at least 98%, or at least 99% identity, or having 100% identity to amino acids 306-537 of SEQ ID NO: 3.

As described herein, ligand binding molecules can be chemically modified to, for example, facilitate connection to a fusion partner (such as, for example, a heterologous peptide) or impart desired characteristics (such as, for example, increase the serum half-life, increase the solubility in an aqueous medium and enable targeting to a specific cell population, e.g., tumor cells or retinal cells).

In some embodiments, a ligand binding molecule described herein optionally comprises at least one PEG moiety attached to the molecule. For example, in some embodiments, PEG of about 20-40 kDa is attached to the amino terminus of the ligand binding molecule.

In some embodiments, a ligand binding molecule as described herein optionally comprises a linker connecting the fusion partner, such as, for example, a heterologous peptide to the ligand binding polypeptide, such as the factor Xa linker sequence PIEGRGGGGG (SEQ ID NO: 4). In other embodiments, the ligand binding molecule comprises a polypeptide in which a C-terminal amino acid of the ligand binding polypeptide is directly attached to an N-terminal amino acid of the heterologous peptide fusion partner by a peptide bond. In some embodiments, the ligand binding polypeptide and the heterologous peptide are attached (directly or through a linker polypeptide) by amide bonding to form a single polypeptide chain.

In some variations, the ligand binding molecule comprises a signal peptide that directs secretion of the molecule from a cell that expresses the molecule.

Nucleic acids (polynucleotides) of the invention include nucleic acids that encode polypeptide ligand binding molecules, which may be used for such applications as gene therapy and recombinant in vitro expression of polypeptide ligand binding molecules. In some embodiments, nucleic acids are purified or isolated. In some embodiments, polynucleotides further comprise a promoter sequence operatively connected to a nucleotide sequence encoding a polypeptide, wherein the promoter sequence promotes transcription of the sequence that encodes the polypeptide in a host cell. Polynucleotides may also comprise a polyadenylation signal sequence. In some variations, the nucleic acid has a coding nucleotide sequence similar to a wild type human VEGFR-3-encoding nucleic acid. For example, the nucleic acid comprises a coding nucleotide sequence having at least 80%, or at least 85%, or at least 90%, or at least 92%, or at least 95%, or at least 96%, or at least 97%, or at least 98%, or at least 99% identity to the human VEGFR-3 sequence set forth in SEQ ID NO: 1, or to a fragment thereof. By way of example, in the context of a nucleotide sequence encoding amino acids 47-314 of SEQ ID NO: 2, modified at the N2 sequon, an exemplary nucleic acid comprises a coding nucleotide sequence having at least 80%, or at least 85%, or at least 90%, or at least 92%, or at least 95%, or at least 96%, or at least 97%, or at least 98%, or at least 99% identity to the human VEGFR-3 sequence set forth in positions 157 to 961 of SEQ ID NO: 1, which correspond to codons 47-314.

Vectors comprising polynucleotides are also aspects of the invention. Such vectors may comprise an expression control sequence operatively connected to the sequence that encodes the polypeptide. In some variations, the vector is selected to optimize in vitro recombinant expression in a chosen host cell, such as a eukaryotic host cell. In some variations, the vector is selected for in vivo delivery. For example, the vector may be selected from the group consisting of a lentivirus vector, an adeno-associated viral vector, an adenoviral vector, a liposomal vector, and combinations thereof. In some embodiments, the vector comprises a replication-deficient adenovirus, said adenovirus comprising the polynucleotide operatively connected to a promoter and flanked by adenoviral polynucleotide sequences.

Host cells comprising the polynucleotides, vectors and other nucleic acids, and methods for using the same to express and isolate the ligand binding molecules are also aspects of the invention. Eukaryotic host cells, including Chinese Hamster Ovary (CHO) cells and other mammalian cell lines comprising a polynucleotide encoding a ligand binding polypeptide or ligand binding molecule described herein are specifically contemplated. In some variations, the cell line is selected or engineered to introduce a human or human-like glycosylation at glycosylation sequons of polypeptides produced in the cells.

Methods of making a ligand binding polypeptide or molecule described herein are also contemplated. (Such methods could also be described as uses of the polynucleotides or cells of the invention.) In one aspect, the method comprises growing a cell that has been transformed or transfected with a polynucleotide or vector described herein under conditions in which the ligand binding polypeptide or ligand binding molecule encoded by the polynucleotide is expressed. In some embodiments, the method further comprises purifying or isolating the ligand binding polypeptide or the ligand binding molecule from the cell or from a growth media of the cell. In some embodiments, the method further includes attaching one or more polyethylene glycol (PEG) or other moieties to the expressed and purified/isolated polypeptide.

The invention also includes compositions comprising a polypeptide, ligand binding molecule or nucleic acid encoding the same, together with a pharmaceutically acceptable diluent, adjuvant, or carrier medium. In some embodiments, the composition is formulated for local administration to the eye (e.g., a topical formulation such as an ointment or eyedrop, or a formulation suitable for intravitreal injection). In other embodiments, the composition is formulated for local administration to a tumor or to the organ or tissue from which the tumor has been surgically removed, e.g., by intravenous injection or injection directly into the affected tissue, or application by way of device during tumor resection. The invention also includes methods of using materials described herein (polypeptides, molecules and constructs, polynucleotides and vectors, transformed cells, compositions) for inhibiting vessel growth (blood vessel and/or lymphatic vessel) in therapeutic and prophylactic contexts. Methods of using as described herein can alternatively be characterized as uses of the various materials for the stated indication. Exemplary subjects for treatment include humans and other primates, livestock (e.g., bovines, equines, porcines), zoo animals (e.g., felines, canines, pachyderms, cervidae), and pets (e.g., dogs, cats), and rodents.

In some variations, the invention includes a method of inhibiting neovascularization in a subject, the method comprising administering to the subject any of the foregoing materials or compositions, in an amount effective to inhibit neovascularization in the subject. Exemplary pathogenic neovascular conditions include those of the eye, and tumor neovascularization.

In some variations, the invention includes a method of inhibiting retinal neovascularization in a subject, the method comprising administering to the subject materials or compositions as described herein, in an amount effective to inhibit retinal neovascularization in the subject. In related variations, the invention includes a method of treating a subject having an ocular disorder associated with retinal neovascularization, the method comprising administering to the subject a material or composition as described herein and summarized above, in an amount effective to inhibit retinal neovascularization in the subject. For example, a composition as described herein is administered locally to the eye of the subject, such as by eye drops or other topical administration, by subconjunvtival administration (e.g., injection), by intravitreal injection, or by intravitreal implant.

Compositions preferably are administered in an amount and at a repeated dosing frequency and duration effective to inhibit VEGF-C and/or VEGF-D in the eye of the subject from binding to or stimulating VEGFR-2 and/or VEGFR-3 expressed in cells of the eye or vessels of the eye. Such beneficial effect may be measured in terms of slowing or halting of deterioration/progression in the pathological eye condition (such as macular degeneration, diabetic retinopathy and macular telangiectasia), or improvement in clinical symptoms. The beneficial effect also may be observable in terms of monitoring of vessel growth in and around the targeted tissue.

Methods and uses described herein may be practiced in combination with additional therapeutic agents or treatments (e.g., forms of radiation), as described herein in detail.

Methods (or uses) of the invention described herein may be carried out with one or more ligand binding molecule, or with at least one ligand binding molecule in combination with another therapeutic (such as a standard of care therapeutic for the treatment of cancer or for the treatment of a back of the eye disorder). In embodiments wherein the ligand binding molecules are for the treatment of a back of the eye disorder, contemplated additional therapies include focal laser treatment (or photocoagulation), scatter laser treatment (or panretinal photocoagulation) and virectomy. In some embodiments, antibiotics are also administered to the subject receiving treatment.

In embodiments where the ligand binding molecules described herein are for use in the treatment of cancer, contemplated standard of care therapeutics include antisense RNA, RNA interference, bispecific antibodies, other antibody types, and small molecules, e.g., chemotherapeutic agents, which target growth factors and/or their receptors. A cytokine, radiotherapeutic agent, or radiation therapy may also be used in combination with a ligand binding molecule described herein. The chemotherapeutic agent or radiotherapeutic agent may be a member of the class of agents including an anti-metabolite; a DNA-damaging agent; a cytokine or growth factor; a covalent DNA-binding drug; a topoisomerase inhibitor; an anti-mitotic agent; an anti-tumor antibiotic; a differentiation agent; an alkylating agent; a methylating agent; a hormone or hormone antagonist; a nitrogen mustard; a radiosensitizer; and a photosensitizer. Specific examples of these agents are described elsewhere in the application. Combination therapies are preferably synergistic, but they need not be, and additive therapies are also considered aspects of the invention.

In addition to their use in methods, the ligand binding molecules may be combined or packaged with other therapeutics in kits or as unit doses. Neoplastic diseases are not the only diseases that may be treated with the ligand binding molecules. The ligand binding molecules may be used as therapeutics for any disease associated with aberrant angiogenesis or lymphangiogenesis.

The invention can also described in the following additional embodiments:

48. A purified or isolated ligand binding polypeptide comprising an amino acid sequence having at least 95% identity to the sequence of amino acids defined by positions 47-115 of SEQ ID NO: 2, with the proviso that positions of the polypeptide corresponding to positions 104-106 of SEQ ID NO: 2 are not identical to N-X-S or N-X-T, wherein the polypeptide binds to at least one ligand polypeptide selected from human VEGF-C, VEGF-D, and PlGF.

49. The purified or isolated ligand binding polypeptide according to paragraph 48, comprising an amino acid sequence having at least 95% identity to the sequence of amino acids defined by positions 47-210 of SEQ ID NO: 2, with the proviso that positions of the polypeptide corresponding to positions 104-106 of SEQ ID NO: 2 are not identical to N-X-S or N-X-T.

50. The purified or isolated ligand binding polypeptide according to paragraph 48, comprising an amino acid sequence having at least 95% identity to the sequence of amino acids defined by positions 47-314 of SEQ ID NO: 2, with the proviso that positions of the polypeptide corresponding to positions 104-106 of SEQ ID NO: 2 are not identical to N-X-S or N-X-T.

51. The purified or isolated ligand binding polypeptide according to paragraph 48, comprising an amino acid sequence having at least 95% identity to the sequence of amino acids defined by positions 47-752 of SEQ ID NO: 2, with the proviso that positions of the polypeptide corresponding to positions 104-106 of SEQ ID NO: 2 are not identical to N-X-S or N-X-T.

52. The purified or isolated ligand binding polypeptide according to any one of paragraphs 48-51 that retains four N-glycosylation sequon sites corresponding to positions 33-35 of SEQ ID NO: 2, positions 166-168 of SEQ ID NO: 2, positions 251-253 of SEQ ID NO: 2, and positions 299-301 of SEQ ID NO: 2.

53. The purified or isolated ligand binding polypeptide according to paragraph 52, that is glycosylated at said four N-glycosylation sequon sites.

54. The purified or isolated ligand binding polypeptide according to any one of paragraphs 48-53 that is a soluble polypeptide.
55. The purified or isolated ligand binding polypeptide according to any one of paragraphs 48-54, comprising an amino acid sequence that is identical to the sequence of amino acids defined by positions 47-115 of SEQ ID NO: 2, positions 47-210 of SEQ ID NO: 2, positions 47-314 of SEQ ID NO: 2, or positions 47-752 of SEQ ID NO: 2, with the proviso that positions of the polypeptide corresponding to positions 104-106 of SEQ ID NO: 2 are not identical to N-X-S or N-X-T.
56. The purified or isolated ligand binding polypeptide according to any one of paragraphs 48-55 that binds human VEGF-C or human VEGF-D.
57. The purified or isolated ligand binding polypeptide according to paragraph 56, that inhibits VEGF-C- or VEGF-D-binding to VEGFR-3 or inhibits VEGF-C- or VEGF-D-mediated stimulation of VEGFR-3 in a cell expressing VEGFR-3 on its surface.
58. The purified or isolated ligand binding polypeptide according to any one of paragraphs 48-57 that binds human VEGF-C with a Kd or 1 nM or less.
59. The purified or isolated ligand binding polypeptide according to any one of paragraphs 48-57, that binds human VEGF-D with a Kd of 5 nM or less.
60. The purified or isolated ligand binding polypeptide according to any one of paragraphs 48-59, wherein the amino acid in the polypeptide corresponding to position 104 of SEQ ID NO: 2 is deleted or replaced with another amino acid.
61. The purified or isolated ligand binding polypeptide according to paragraph 55, wherein the amino acid at position 104 of SEQ ID NO: 2 is deleted or replaced with another amino acid selected from the group consisting of glutamine, aspartate, glutamate, arginine and lysine.
62. The purified or isolated ligand polypeptide according to any one of paragraphs 48-56, wherein the polypeptide comprises amino acids 23-290 of SEQ ID NO: 3.
63. The purified or isolated ligand binding polypeptide according to any one of paragraphs 48-62, further comprising a signal peptide.
64. The purified or isolated ligand binding polypeptide according to any one of paragraphs 48-63, further comprising at least one polyethylene glycol moiety attached to the polypeptide.
65. The purified or isolated ligand binding polypeptide according to paragraph 64, comprising polyethylene glycol of about 20-40 kDa attached to the amino terminus of the polypeptide.
66. A ligand binding molecule comprising the ligand binding polypeptide according to any one of paragraphs 48-65 connected to a heterologous peptide.
67. The ligand binding molecule according to paragraph 66, wherein the heterologous peptide comprises an immunoglobulin constant domain fragment.
68. The ligand binding molecule according to paragraph 66, wherein the immunoglobulin constant domain fragment is an IgG constant domain fragment.
69. The ligand binding molecule according to paragraph 67, wherein the immunoglobulin constant fragment comprises amino acids 306-537 of SEQ ID NO: 3.
70. The ligand binding molecule according to paragraph 66, wherein the ligand binding molecule comprises amino acids 22-537 of SEQ ID NO: 3.
71. The ligand binding molecule according to any one of paragraphs 66-70, optionally comprising a linker connecting the heterologous peptide to the ligand binding polypeptide.
72. The ligand binding molecule according to any one of paragraphs 66-70 that comprises a polypeptide in which a C-terminal amino acid of the ligand binding polypeptide is directly attached to an N-terminal amino acid of the heterologous peptide by a peptide bond.
73. The ligand binding molecule according to any one of paragraphs 66-72, further comprising a signal peptide that directs secretion of the molecule from a cell that expresses the molecule.
74. The ligand binding molecule according to paragraph 66, wherein the molecule comprises the amino acid sequence set forth in SEQ ID NO: 3.
75. The ligand binding molecule according to any one of paragraphs 66-70, wherein the ligand binding polypeptide and the heterologous peptide are linked by amide bonding to form a single polypeptide chain.
76. The ligand binding polypeptide according to any one of paragraphs 48-65 or the ligand binding molecule according to any one of paragraphs 66-75, further comprising a detectable label.
77. A conjugate comprising the ligand binding polypeptide according to any one of paragraphs 48-65 or the ligand binding molecule according to any one of paragraphs 66-75 and a chemotherapeutic agent.
78. An isolated polynucleotide comprising a coding nucleotide sequence encoding the ligand binding polypeptide according to any one of paragraphs 48-65 or the ligand binding molecule according to any one of paragraphs 66-75.
79. The polynucleotide according to paragraph 78, further comprising a promoter sequence operatively connected to the coding nucleotide sequence to promote transcription of the coding nucleotide sequence in a host cell.
80. A vector comprising the polynucleotide of paragraph 78 or paragraph 79.
81. The vector according to paragraph 80, further comprising an expression control sequence operatively connected to the coding nucleotide sequence.
82. The vector according to paragraph 80, wherein said vector is selected from the group consisting of a lentivirus vector, an adeno-associated viral vector, an adenoviral vector, a liposomal vector, and combinations thereof.
83. The vector according to paragraph 80, wherein said vector comprises a replication-deficient adenovirus, said adenovirus comprising the polynucleotide operatively connected to a promoter and flanked by adenoviral polynucleotide sequences.
84. An isolated cell or cell line transformed or transfected with a polynucleotide according to paragraph 78 or 79 or with a vector according to paragraph 80-83.
85. The isolated cell or cell line according to paragraph 84 that is a eukaryotic cell.
86. The isolated cell or cell line according to paragraph 84 that is a human cell.
87. The isolated cell or cell line according to paragraph 84, that is a Chinese Hamster Ovary (CHO) cell.
88. A method of making a ligand binding polypeptide comprising growing a cell according to any one of paragraphs 84-87 under conditions in which the ligand binding polypeptide or ligand binding molecule encoded by the polynucleotide is expressed.

89. The method according to paragraph 88, further comprising purifying or isolating the ligand binding polypeptide or the ligand binding molecule from the cell or from a growth media of the cell.

90. A composition comprising a purified ligand binding polypeptide or ligand binding molecule according to any one of paragraphs 48-76 and a pharmaceutically acceptable diluent, adjuvant, excipient, or carrier.

91. A composition comprising a polynucleotide or vector according to any one of paragraphs 78-83 and a pharmaceutically acceptable diluent, adjuvant, excipient, or carrier.

92. The composition according to paragraph 90 or paragraph 91, that is formulated for topical administration.

93. The composition according to paragraph 92, that is in the form of a solid, a paste, an ointment, a gel, a liquid, an aerosol, a mist, a polymer, a film, an emulsion, or a suspension.

94. The composition according to paragraph 90 or paragraph 91, that is formulated for intravitreal administration.

95. A method of inhibiting neovascularization in a subject, the method comprising administering to the subject a composition according to any one of paragraphs 90-94 in an amount effective to inhibit neovascularization in the subject.

96. A method of inhibiting retinal neovascularization in a subject, the method comprising administering to the subject a composition according to any one of paragraphs 90-94, in an amount effective to inhibit retinal neovascularization in the subject.

97. A method of treating a subject having an ocular disorder associated with retinal neovascularization, the method comprising administering to the subject a composition according to any one of paragraphs 90-95, in an amount effective to inhibit retinal neovascularization in the subject.

98. Use of a composition according to any one of paragraphs 90-94 for inhibiting neovascularization, such as retinal neovascularization or tumor neovascularization, in a subject in need thereof.

99. The method or use according to any one of paragraphs 96-98, wherein the composition is administered locally to the eye of the subject.

100. The method or use according to paragraph 99, wherein the composition is administered by intravitreal injection.

101. The method or use according to paragraph 99, wherein the composition is administered by topical administration.

102. The method or use according to any one of paragraphs 96-101, wherein the composition is administered in an amount effective to inhibit VEGF-C and/or VEGF-D in the eye of the subject from binding to or stimulating VEGFR-2 and/or VEGFR-3 expressed in cells of the eye or vessels of the eye.

103. The method or use of paragraph 97 or 98, wherein the ocular disorder is selected from the group consisting of macular degeneration, diabetic retinopathy and macular telangiectasia.

104. The method or use according to any one of paragraphs 96-103, further comprising administering an antibiotic to the subject.

105. The method according to paragraph 104, wherein the antibiotic is selected from the group consisting of amikacin, gentamicin, kanamycin, neomycin, netilmicin, streptomycin, tobramycin, teicoplanin, vancomycin, azithromycin, clarithromycin, clarithromycin, dirithromycin, erythromycin, roxithromycin, troleandomycin, amoxicillin, ampicillin, azlocillin, carbenicillin, clozacillin, dicloxacillin, flucozacillin, meziocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, oflazacin, trovafloxacin, mafenide, sulfacetamide, sulfamethizole, sulfasalazine, sulfisoxazole, trimethoprim, cotrimoxazole, demeclocycline, soxycycline, minocycline, oxytetracycline, and tetracycline.

106. The method or use according to paragraph 95-98, wherein the subject has been diagnosed with a tumor, and wherein the composition is administered in an amount effective to inhibit neovascularization in the tumor.

107. The method or use according to paragraph 106, wherein the composition is administered locally to the tumor or to the organ or tissue from which the tumor has been surgically removed.

108. The method or use according to paragraph 106, wherein the composition is administered in an amount effective to inhibit VEGF-C and/or VEGF-D in the tumor of the subject from binding to or stimulating VEGFR-2 and/or VEGFR-3 expressed in tumor cells.

This summary of the invention is not intended to be limiting or comprehensive, and additional embodiments are described in the drawings and detailed description, including the examples. All such embodiments are aspects of the invention. Moreover, for the sake of brevity, various details that are applicable to multiple embodiments have not been repeated for every embodiment. Variations reflecting combinations and rearrangements of the embodiments described herein are intended as aspects of the invention. In addition to the foregoing, the invention includes, as an additional aspect, all embodiments of the invention narrower in scope in any way than the variations specifically mentioned above. For example, for aspects described as a genus or range, every subgenus, subrange or species is specifically contemplated as an embodiment of the invention.

BRIEF DESCRIPTION OF THE FIGURE

FIG. 2A and FIG. 2B demonstrate that both VGX-300 and VGX-301-ΔN2 specifically bound to both VEGF-C and VEGF-D.

FIG. 4A and FIG. 4B show VGX-300 and VGX-300-N2 block VEGF-C (FIG. 4A) and VEGF-D (FIG. 4B) binding and cross-linking of VEGFR-3 in a cell-based Ba/F3 assay. Data points represent the average of n≥2±SD.

DETAILED DESCRIPTION

Figure 1A:
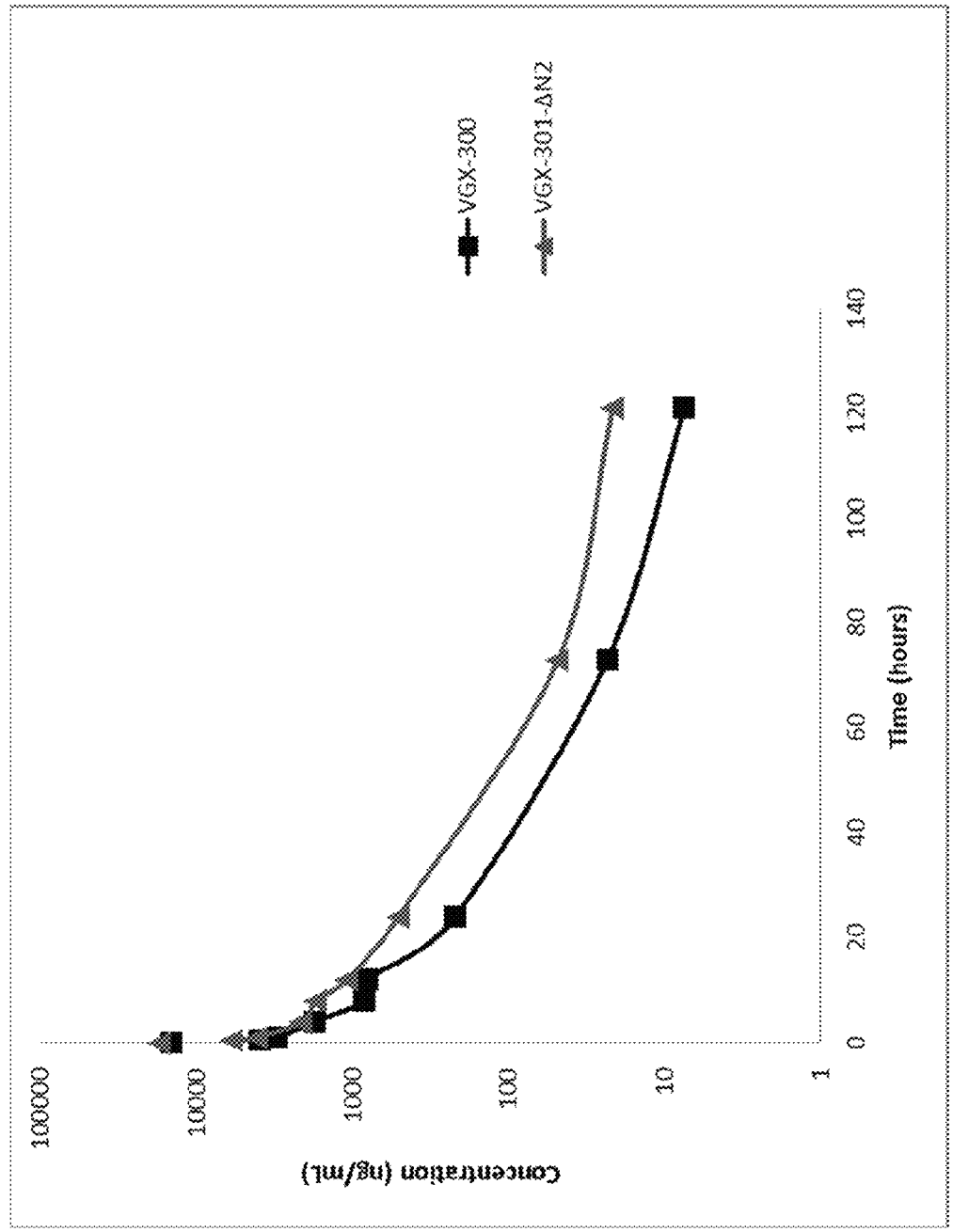
FIG. 1A shows the PK profiles of VGX-300 and VGX-301-ΔN2 produced by transient CHO expression.

The present invention is based in part on research demonstrating that fragments of the ECD of human VEGFR-3 having one or modifications in an N-glycan region of the ECD are capable of binding to and neutralizing human VEGF-C and human VEGF-D in vitro and are also capable of inhibiting vessel development in animal models of age-related macular degeneration.

Growth factor receptor tyrosine kinases generally comprise three principal domains: an extracellular domain (ECD), a transmembrane domain, and an intracellular domain. The ECD binds ligands, the transmembrane domain anchors the receptor to a cell membrane, and the intracellular domain possesses one or more tyrosine kinase enzymatic domains and interacts with downstream signal transduction molecules. The vascular endothelial growth factor receptors (VEGFRs) bind their ligand through their ECDs, which are comprised of multiple immunoglobulin-like domains (Ig-like domains). Ig-like domains are identified herein using the designation "D#." For example "D1" refers to the first Ig-like domain of a particular receptor ECD. "D1-3" refers to a construct containing at least the first three Ig-like domains, and intervening sequence between domains 1 and 2 and 2 and 3, of a particular ligand binding molecule.

The complete ECD of VEGFRs is not required for ligand (growth factor) binding. The ECD of VEGFR-3 has six intact Ig-like domains and one cleaved Ig-like domain—D5 of VEGFR-3 is cleaved post-translationally into disulfide linked subunits leaving VEGFR-3. Veikkola, T., et al., *Cancer Res.* 60:203-212 (2000). In some embodiments, receptor fragments comprising at least the first three Ig-like domains for this family are sufficient to bind ligand. Soluble receptors capable of binding VEGF-C and VEGF-D, thereby inhibiting VEGF-C or VEGF-D activity or signaling via VEGFR-3, are also disclosed in WO2000/023565, WO2000/021560, WO2002/060950 and WO2005/087808, the disclosures of which are incorporated herein by reference in their entireties. Those soluble receptors, modified with the ΔN2 sequon change and optionally other modifications described herein, are contemplated as aspects of the invention.

Table 1 defines approximate boundaries of the Ig-like domains for human VEGFR-3. These boundaries are significant as the boundaries chosen can be used to form ligand binding molecules, and so can influence the binding properties of the resulting constructs.

TABLE 1

Immunoglobulin-like domains for human VEGFR-3

|    | VEGFR-3 SEQ ID NO: 1 positions | VEGFR-3 SEQ ID NO: 2 positions |
|----|-------------------------------|-------------------------------|
| D1 | 158-364                       | 47-115                        |
| D2 | 479-649                       | 154-210                       |
| D3 | 761-961                       | 248-314                       |
| D4 | 1070-1228                     | 351-403                       |
| D5 | 1340-1633                     | 441-538                       |
| D6 | 1739-1990                     | 574-657                       |
| D7 | 2102-2275                     | 695-752                       |

The complete ECD extends to about position 775 of SEQ ID NO: 2.

Soluble receptor constructs for use as a ligand binding molecule for human VEGF-C or VEGF-D preferably comprise at least one Ig-like domain of VEGFR-3 as described in Table 1, to as many as seven. The ligand binding molecule optionally will include sequence before the most N-terminally positioned Ig-like domain, optionally will include sequence beyond the most C-terminally Ig-like domain, and optionally will include sequence between the Ig-like domains as well. Variants, e.g., with one or more amino acid substitutions, additions, or deletions of an amino acid residue, are also contemplated. In some embodiments, the ligand binding molecule comprises a fragment of human VEGFR-3 comprising at least the first three Ig-like domains of human VEGFR-3.

In some embodiments, the ligand binding molecule is a polypeptide that comprises a portion of a human VEGFR-3 ECD, wherein the portion binds to one or both of human VEGF-C and human VEGF-D, and comprises at least the first, second and third Ig-like domains of the VEGFR-3 ECD, wherein the amino acid sequence of the ECD fragment of VEGFR-3 is modified from wildtype VEGFR-3 to eliminate the second putative N-linked glycosylation sequon of wildtype VEGFR-3, and wherein the polypeptide lacks VEGFR-3 Ig-like domains 4-7 and preferably any transmembrane domain and preferably any intracellular domain.

In some embodiments, the ligand binding molecule comprises a polypeptide similar or identical in amino acid sequence to a human VEGFR-3 polypeptide (SEQ ID NO: 2) or fragment thereof, with the proviso that positions of the ligand binding molecule corresponding to positions 104-106 of the human VEGFR-3 polypeptide set forth in SEQ ID NO: 2 are not identical to N-X-S or N-X-T, wherein the ligand binding molecule binds one or more growth factors selected from the group consisting of human VEGF-C and human VEGF-D. The fragment minimally comprises enough of the VEGFR-3 sequence to bind the ligand, and may comprise the complete receptor. ECD fragments are preferred. Preferred polypeptides have an amino acid sequence at least 80% identical to a ligand binding fragment thereof. Fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the VEGFR-3 receptor.

The term "identity", as known in the art, refers to a relationship between the sequences of two or more polypeptide molecules or two or more nucleic acid molecules, as determined by comparing the sequences. In the art, "identity" also means the degree of sequence relatedness nucleic acid molecules or polypeptides sequences, as the case may be, as determined by the match between strings of two or more nucleotide or two or more amino acid sequences. "Identity" measures the percent of identical matches between the smaller of two or more sequences with gap alignments (if any) addressed by particular a mathematical model of computer program (i.e., "algorithms"). Appropriate algorithms for determining the percent identities of the invention include BLASTP and BLASTN, using the most common and accepted default parameters.

Ligand binding molecules may also be described as having an amino acid sequence encoded by a nucleic acid sequence at least 80% identical to a fragment of SEQ ID NO: 1 encoding a ligand binding fragment of VEGFR-3, with the proviso that positions of the ligand binding molecule corresponding to positions 104-106 of the encoded ligand binding fragment of VEGFR-3 are not identical to N-X-S or N-X-T. Nucleic acid fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. For example, a preferred ligand binding molecule comprises an amino acid sequence that binds human VEGF-C and/or human VEGF-D and that is encoded by a nucleotide sequence that hybridizes to the complement of SEQ ID NO: 1 under moderately or highly stringent conditions discussed herein.

In some embodiments, the ligand binding molecule comprises a polypeptide comprising a fragment of human VEGFR-3 (SEQ ID NO: 2) selected from the group consisting of positions 1-226 or 25-226 of SEQ ID NO: 2, positions 1-229 or 25-229 of SEQ ID NO: 2 and positions 1-329 or 25-229 of SEQ ID NO: 2, with the proviso that positions 104-106 of the encoded ligand binding fragment of VEGFR-3 are not identical to N-X-S or N-X-T. In some embodiments, the ligand binding molecule is a polypeptide comprising a fragment of human VEGFR-3 (SEQ ID NO: 2) selected from the group consisting of positions 47-224 of SEQ ID NO: 2, positions 47-225 of SEQ ID NO: 2, positions 47-226 of SEQ ID NO: 2, positions 47-227 of SEQ ID NO: 2, positions 47-228 of SEQ ID NO: 2, positions 47-229 of SEQ ID NO: 2, positions 47-230 of SEQ ID NO: 2, positions 47-231 of SEQ ID NO: 2, positions 47-232 of SEQ ID NO: 2, positions 47-236 of SEQ ID NO: 2, positions 47-240 of SEQ ID NO: 2, and positions 47-245 of SEQ ID NO: 2, with the proviso that positions 104-106 of the encoded ligand binding fragment of VEGFR-3 are not identical to N-X-S or N-X-T. In some embodiments, the ligand binding molecule is a polypeptide comprising a fragment of human VEGFR-3 (SEQ ID NO: 2), selected from the group consisting of positions 47-314 of SEQ ID NO: 2, positions 47-210 of SEQ ID NO: 2, and positions 47-247 of SEQ ID NO: 2, with the proviso that positions 104-106 of the encoded ligand binding fragment of VEGFR-3 are not identical to N-X-S or N-X-T.

Ligand binding molecules can also be described as having an amino acid sequence that is similar or identical to the amino acid sequence set forth in SEQ ID NO: 3. Preferred polypeptides have an amino acid sequence at least 80% identical to the amino acid sequence set forth in SEQ ID NO: 3, with the proviso that positions 80-82 of the polypeptide set forth in SEQ ID NO: 3 are not identical to N-X-S or N-X-T, wherein the ligand binding molecule binds one or more growth factors selected from the group consisting of human VEGF-C and human VEGF-D. Polypeptides that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the VEGFR-3 receptor.

In some embodiments, the ligand binding molecule comprises an amino acid sequence comprising amino acids 22-290 of SEQ ID NO: 3. In some embodiments, the ligand binding molecule comprises an amino acid sequence comprising amino acids 23-290 of SEQ ID NO: 3. In some embodiments, the ligand binding molecule comprises amino acids 22-537 of SEQ ID NO: 3, or amino acids 23-537 of SEQ ID NO: 3 or amino acids 1-537 of SEQ ID NO: 3.

The term "component domain" as used herein to refers to a domain within a ligand binding molecule which is derived from or based on a protein domain within the extracellular portion of a receptor protein. For example, each Ig-domain of VEGFR-3 (D1-D7) and other tyrosine kinase receptor family members (e.g. such as VEGFR-1 and VEGFR-2) constitute component domains. Reference herein to a component domain includes both the complete native wildtype domain and also insertional, deletional and/or substitutional variants thereof which substantially retain the functional characteristics of the intact domain. It will be readily apparent to one of skill in the art that numerous variants of the above domains (e.g. Ig-domains) can be obtained which will retain substantially the same functional characteristics as the wild-type domain.

The growth factor receptors, from which ligand binding molecules may be derived, include splice variants and naturally-occurring allelic variations. Allelic variants are well known in the art, and represent alternative forms or a nucleic acid sequence that comprise substitution, deletion or addition of one or more nucleotides, but which do not result in any substantial functional alteration of the encoded polypeptide. Exemplary allelic variants of VEGFR-3 have been reported in the literature, e.g., at http<colon>//www.uniprot.org/uniprot/P35916, and include positions 149, 378, 494, 527, and 641 within the ECD. Standard methods can readily be used to generate such polypeptides including site-directed mutagenesis of polynucleotides, or specific enzymatic cleavage and ligation. Similarly, use of peptidomimetic compounds or compounds in which one or more amino acid residues are replaced by a non-naturally-occurring amino acid or an amino acid analog that retain binding activity is contemplated. Preferably, where amino acid substitution is used, the substitution is conservative, i.e. an amino acid is replaced by one of similar size and with similar charge properties. As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids that can be substituted for one another include asparagine, glutamine, serine and threonine. The term "conservative substitution" also includes the use of a substituted amino acid in place of an unsubstituted amino acid.

Alternatively, conservative amino acids can be grouped as described in Lehninger, (*Biochemistry*, Second Edition; Worth Publishers, Inc. NY: NY, pp. 71-77 (1975)) as set out in the following:

Non-polar (hydrophobic)
A. Aliphatic: A, L, I, V, P,
B. Aromatic: F, W,
C. Sulfur-containing: M,
D. Borderline: G.
Uncharged-polar
A. Hydroxyl: S, T, Y,
B. Amides: N, Q,
C. Sulfhydryl: C,
D. Borderline: G.
Positively Charged (Basic): K, R, H.
Negatively Charged (Acidic): D, E.

For the avoidance of doubt, "component domain" includes a domain corresponding to D1 of VEGFR-3 in which the N-X-S/T sequon motif at position 104-106 of SEQ ID No: 2 has been mutated, e.g. due to substitution.

In embodiments where the ligand binding molecule comprises multiple component domains, for example component domains D1, D2 and D3 of VEGFR-3, the component domains may be connected directly to each other or may be connected via one or more spacers. Generally, the term "spacer" means one or more molecules, for example nucleic acids or amino acids, or non-peptide moieties, such as polyethylene glycol or disulfide bridges, which may be inserted between one or more component domains forming a covalent bond. Spacer sequences may be used to provide a desirable site of interest between components for ease of manipulation. A spacer may also be provided to enhance expression of the ligand binding polypeptide from a host cell, to decrease steric hindrance such that the component or group of components may assume its/their optimal tertiary structure and/or interact appropriately with its/their target molecule. For spacers and methods of identifying desirable spacers, see, for example, George et al. (2003) Protein Engineering 15:871-879, herein specifically incorporated by reference. A spacer sequence may include one or more amino acids naturally connected to a receptor component, or may be an added sequence used to enhance expression of the ligand binding polypeptides, provide specifically desired sites of interest, allow component domains to form optimal tertiary structures and/or to enhance the interaction of a component or group of components with its/their target molecule. In one embodiment, the spacer comprises one or more peptide sequences between one or more components which is (are) between 1-100 amino acids, preferably 1-50 amino acids in length. In a preferred embodiment, the spacer between two component domains substantially consists of amino acids naturally connected to the receptor component in the wildtype receptor. In the case of a ligand binding molecule comprising multiple component domains from the same receptor which domains are adjacent each other in the native receptor, such as for example D1, D2 and D3 of VEGFR-3, in one embodiment, the domains are connected to each other (e.g. D1 to D2 and D2 to D3) using spacers corresponding to the naturally-occurring amino acid linking sequences.

In some variations, each ligand binding polypeptide is expressed as a fusion with a fusion partner protein, such as an immunoglobulin constant region, and the heterologous fusion partners are linked to form the ligand binding molecule.

Multimers, Multimerizing Components, Fusion Partners and Linkers

The fusion partner is any heterologous component that enhances the functionality of the ligand binding molecule. Thus, for example, a fusion partner may increase the solubility, modulate the clearance, facilitate targeting of particular cell or tissue types, enhance the biological activity, aid the production and/or recovery, enhance a pharmacological property or enhance a pharmacokinetic (PK) profile of the ligand binding polypeptide. With regards to enhancing the PK profile, this may be achieved by, for example, enhancing the serum half-life, tissue penetrability, lack of immunogenicity or stability of the ligand binding molecule. In preferred embodiments, a fusion partner is selected from the group consisting of a multimerizing component, a serum protein or a molecule capable of binding a serum protein.

When the fusion partner is a serum protein or fragment thereof, it is selected from the group consisting of α-1-microglobulin, AGP-1, orosomuciod, α-1-acid glycoprotein, vitamin D binding protein (DBP), hemopexin, human serum albumin (hSA), transferrin, ferritin, afamin, haptoglobin, α-fetoprotein thyroglobulin, α-2-HS-glycoprotein, β-2-glycoprotein, hyaluronan-binding protein, syntaxin, C1R, C1q a chain, galectin3-Mac2 binding protein, fibrinogen, polymeric Ig receptor (PIGR), α-2-macroglobulin, urea transport protein, haptoglobin, IGFBPs, macrophage scavenger receptors, fibronectin, giantin, Fc, α-1-antichyromotrypsin, α-1-antitrypsin, antithrombin III, apolipoprotein A-1, apolipoprotein B, β-2-microglobulin, ceruloplasmin, complement component C3 or C4, CI esterase inhibitor, C-reactive protein, cystatin C, and protein C. In a more specified embodiment, the fusion partner is selected from the group consisting of α-1-microglobulin, AGP-1, orosomuciod, α-1-acid glycoprotein, vitamin D binding protein (DBP), hemopexin, human serum albumin (hSA), afamin, and haptoglobin. The inclusion of a fusion partner component may extend the serum half-life of the fusion polypeptide of the invention when desired. See, for example, U.S. Pat. Nos. 6,423,512, 5,876,969, 6,593,295, and 6,548,653, herein specifically incorporated by reference in their entirety, for examples of serum albumin fusion polypeptides. hSA is widely distributed throughout the body, particularly in the intestinal and blood components, and has an important role in the maintenance of osmolarity and plasma volume. It is slowly cleared in the liver, and typically has an in vivo half-life of 14-20 days in humans (Waldmann et al. (1977) Albumin, Structure Function and Uses; Pergamon Press; pp. 255-275).

When a fusion partner is a molecule capable of binding a serum protein, the molecule may be a synthetic small molecule, a lipid or liposome, a nucleic acid, including a synthetic nucleic acid such as an aptomer, a peptide, or an oligosaccharide. The molecule may further be a protein, such as, for example, FcγR1, FcγR2, FcγR3, polymeric Ig receptor (PIGR), ScFv, and other antibody fragments specific for a serum protein.

When the fusion partner is a multimerizing component, it is any natural or synthetic sequence or compound capable of operably linking a first ligand binding molecule with another ligand binding molecule or another multimerizing component of another ligand binding molecule to form a higher order structure, e.g., a dimer, a trimer, etc. Suitable multimerizing components may include a leucine zipper, including leucine zipper domains derived from c-jun or c-fos; sequences derived from the constant regions of kappa or lambda light chains; synthetic sequences such as helix-loop-helix motifs (Muller et al. (1998) FEBS Lett. 432:45-49), coil-coil motifs, etc., or other generally accepted multimerizing domains known to the art. In some embodiments, the fusion component comprises an immunoglobulin-derived domain from, for example, human IgG, IgM or IgA.

In one aspect, a ligand binding molecule described herein is produced as a multimer. Each subunit of the multimer comprises or consists of a ligand binding molecule, for example a ligand binding polypeptide. These multimers may be homodimeric, heterodimeric, or multimeric soluble receptors, with multimeric receptors consisting of 9 or fewer subunits, preferably 6 or fewer subunits, even more preferably 3 or fewer subunits, and most preferably 2 subunits. Preferably, these multimeric soluble receptors are homodimers of ligand binding molecules.

The at least two subunits in a multimer are operably linked to one another. The term "operably linked" indicates that the subunits are associated through covalent and/or non-covalent bonding. The subunits may be covalently linked by any suitable means, such as via a cross-linking reagent or a linker such as a polypeptide or peptide linker. In another embodiment, the subunits are linked via non-covalent linkages. In some variations, the two subunits (for example two ligand binding polypeptides) are attached by a peptide linkage, either directly or via a "peptide linker". The peptide linker can be as short as 1 to 3 amino acid residues in length (preferably consisting of small amino acids such as glycine, serine, threonine or alanine) or longer, for example 13, 15 or 16 amino acid residues in length, introduced between the subunits. Preferably, the peptide linker is a peptide which is immunologically inert. Said linker may be a tripeptide of the sequence E-F-M (Glu-Phe-Met), for example, a 13-amino acid linker sequence consisting of Glu-Phe-Gly-Ala-Gly-Leu-Val-Leu-Gly-Gly-Gln-Phe-Met (SEQ ID NO: 7), a 15-amino acid linker sequence consisting Of (G4S)3 (SEQ ID NO: 8), a 16-amino acid linker sequence consisting of GGSGG SGGGG SGGGG S (SEQ ID NO: 9) or the hinge region of human IgG (e.g. IgGI, IgG2, IgG3 or IgG4). In some variations, the two subunits are ligand binding polypeptides comprising two distinct polypeptide chains that are linked to each other, e.g, by disulfide bonding or other bonds.

In some embodiments, the ligand binding molecule is in the form of a fusion protein comprising at least two subunits each comprising a ligand binding polypeptide. In this manner, the fusion protein can be produced recombinantly, by direct expression in a host cell of a nucleic acid molecule encoding the same as a single open reading frame.

In some variations, a ligand binding polypeptide is expressed as a fusion with a heterologous protein fusion partner, such as an immunoglobulin constant region, and the heterologous fusion partners are linked to form a multimeric ligand binding molecule. In one embodiment, the subunits are operably linked to a multimerizing component. A multimerizing component includes any natural or synthetic sequence capable of operably linking two or more subunits to form a higher order structure, e.g., a dimer, a trimer, etc. A multimerizing component may operably link two or more subunits by interacting "directly" with the subunits. Alternatively, a multimerizing component for one subunit may interact with another multimerizing component for another subunit to operably link the subunits.

In one embodiment, the subunits are operably linked to an additional amino acid domain that provides for the multimerization of the subunits (in particular the additional domains comprise any functional region providing for dimerization of the subunits). The term "operably linked" indicates that VEGFR-3-based subunit, and the additional amino acid domain are associated through peptide linkage, either directly or via a "peptide linker" (as defined herein), and the VEGFR-3-based subunit retains ligand binding properties. The additional amino acid domain may be located upstream (N-ter) or downstream (C-ter) from the VEGFR-3 subunit sequence. Preferably it is located downsteam (i.e. away from the first immunoglobulin-like domain (Ig-I domain). In this manner, the fusion protein can be produced recombinantly, by direct expression in a host cell of a nucleic acid molecule encoding the same. In such embodiments, a ligand binding molecule described herein is a multimer of fusion proteins containing ligand binding polypeptides and a multimerizing component capable of interacting with the multimerizing component present in another fusion protein to form a higher order structure, such as a dimer. These type of fusion proteins may be prepared by operably linking the VEGFR-3 subunit sequence (i.e., ligand binding polypeptide) to domains isolated from other proteins allowing the formation of dimers, trimers, etc. Examples for protein sequences allowing the multimerization of the ligand polypeptides described herein include, but are not limited to, domains isolated from proteins such as immunoglobulins, hCG (WO 97/30161), collagen X (WO 04/33486), C4BP (WO 04/20639), Erb proteins (WO 98/02540) or coiled coil peptides (WO 01/00814), the disclosure of which are incorporated herein by reference in their entireties.

The multimerizing component may, for example, be selected from (i) an amino acid sequences between 1 to about 500 amino acids in length, (ii) leucine zippers, (iii) helix loop motifs and (iv) coil-coil motifs. When the multimerizing component comprises an amino acid sequence between 1 to about 500 amino acids in length, the sequence may contain one or more cysteine residues capable of forming a disulfide bond with a corresponding cysteine residue on another fusion polypeptide comprising a multimerizing component with one or more cysteine residues.

In a particular aspect, the multimers are dimers of ligand binding polypeptides where the polypeptides are operably linked to an immunoglobulin or a portion of an immunoglobulin as the fusion partner, which may also act as the multimerizing component. The term "operably linked" indicates that the ligand binding polypeptides and the immunoglobulin or portion thereof are associated through peptide linkage, either directly or via a "peptide linker" (as defined herein), and ligand binding properties of the ligand binding polypeptides are retained. In this embodiment, the ligand binding polypeptides are operably linked to all or a portion of an immunoglobulin, particularly a human immunoglobulin, even more particularly the Fc portion of a human immunoglobulin. Typically an Fc portion of a human immunoglobulin contains two constant region domains (the CH2 and CH3 domains) and a hinge region but lacks the variable region. (See e.g. U.S. Pat. Nos. 6,018,026 and 5,750,375, incorporated herein by reference.) The immunoglobulin may be selected from any of the major classes of immunoglobulins, including IgA, IgD, IgE, IgG and IgM, and any subclass or isotype, e.g. IgG1, IgG2, IgG3 and IgG4; IgA-I and IgA-2. In an embodiment, the Fc moiety is of human IgG4, which is stable in solution and has little or no complement activating activity. In another embodiment, the Fc moiety is of human IgGI. The Fc part may be mutated in order to prevent unwanted activities, such as complement binding, binding to Fc receptors, or the like. The amino acid sequence derived from the immunoglobulin may be linked to the C-terminus or to the N-terminus of the ligand binding polypeptide, preferably to the C-terminus. Such fusion proteins can be prepared by transfecting cells with DNA encoding VEGFR-3 zsubunit:Fc fusion protein and expressing the dimers in the same cells. In a particular embodiment, the ligand binding polypeptides are the same on each monomer subunit (i.e the dimer is a homodimer). Methods for making immunoglobulin fusion proteins are well known in the art, such as the ones described in Hollenbaugh and Aruffo ("Construction of Immunoglobulin Fusion Proteins", in Current Protocols in Immunology, Suppl. 4, pages 10.19.1-10.19.11, 1992) or WO 01/03737, for example, both incorporated herein by reference.

Alternatively, the dimers of ligand binding polypeptides of the present invention can be prepared by operably linking one of the ligand binding polypeptides to the constant region of an immunoglobulin heavy chain and operably linking the other ligand binding polypeptide to the constant region of an immunoglobulin light chain. For example, a ligand binding polypeptide can be operably linked to the CH1-hinge-CH2-CH3 region of human IgG1 and another or the same ligand binding polypeptide can be operably linked to the C kappa region of the Ig kappa light chain. In an embodiment, the heavy constant chain is human γ4, which is stable in solution and has little or no complement activating activity. In another embodiment, the heavy constant chain is human γI. The heavy constant chain may be mutated in order to prevent unwanted activities, such as complement binding, binding to Fc receptors, or the like.

Also, if needed, fusion proteins described herein may comprise any functional region facilitating purification or production. Specific examples of such additional amino acid sequences include a GST sequence or a His tag sequence. In some variations, the region facilitating purification is removed for formulation of a composition for pharmaceutical use.

The amino acid sequence derived from the immunoglobulin may be linked to the C-terminus or to the N-terminus of the ligand binding polypeptide, preferably to the C-terminus. Cells transfected with DNA encoding the immunoglobulin light chain fusion protein and the immunoglobulin heavy chain fusion protein express heavy chain/light chain heterodimers containing each a ligand binding polypeptide. Both ligand binding polypeptides advantageously comprise a native or heterologous signal peptide when initially synthesized, to promote secretion from the cell, but the signal sequence is cleaved upon secretion. Variations of any of the foregoing embodiments that include the signal peptide are contemplated. The native signal peptide of human VEGFR-3 comprises residues 1-24 of SEQ ID NO: 2. Numerous other signal peptide proteins are taught in the literature.

In another particular aspect of the present invention, ligand binding polypeptides of the multimers are linked via non-covalent linkages. Non-covalent bonding of the subunits may be achieved by any suitable means that does not interfere with its biological activity (i.e. its ability to bind human VEGF-C and/or VEGF-D). In a particular aspect, these multimers are dimers of ligand binding polypeptides where one ligand binding polypeptide is operably linked to a first compound and another or the same ligand binding polypeptide is operably linked to a second compound that will non-covalently bond to the first compound. Examples of such compounds are biotin and avidin. The dimers of ligand binding polypeptides can be prepared by operably linking one VEGFR-3 subunit to biotin and operably linking the other ligand binding polypeptide to avidin. The receptor is thus formed through the non-covalent interactions of biotin with avidin. Other examples include subunits of heterodimeric proteinaceous hormone. In these embodiments, a DNA construct encoding one ligand binding protein is fused to a DNA construct encoding a subunit of a heterodimeric proteinaceous hormone, such as hCG, and a DNA construct encoding the other ligand binding polypeptide is fused to DNA encoding the other subunit of the heterodimeric proteinaceous hormone, such as hCG (as disclosed in U.S. Pat. No. 6,193,972). These DNA constructs are co-expressed in the same cells leading to the expression of a ligand binding molecule, as each co-expressed sequence contains a corresponding hormone subunit so as to form a heterodimer upon expression. The amino acid sequence derived from the heterodimeric proteinaceous hormone may be linked to the C-terminus or to the N-terminus of the ligand binding polypeptides, preferably to the C-terminus. Both subunits advantageously comprise a native or heterologous signal peptide when initially synthesized, to promote secretion from the cell, but the signal sequence is cleaved upon secretion.

In one embodiment, the ligand binding molecule is operably linked to a non-VEGFR-3 derived binding unit, i.e. a binding unit which contains no component domains derived from VEGFR-3. Such chimeric ligand binding molecules may, for example, comprise heterologous binding units based on other tyrosine kinase receptors. In one embodiment, such heterologous binding units bind to at least one ligand polypeptide selected from VEGF-A (VEGF), VEGF-B, PlGF, PDGF-A, PDGF-B, PDGF-C and PDGF-D. In a preferred embodiment, such heterologous binding units bind to at least VEGF-A (VEGF).

In one embodiment, such heterologous binding units comprise component domains derived from VEGFR-1 or VEGFR-2 or both. An examples of heterologous binding units which may be employed, in combination with the ligand binding molecules of the present invention in the form of chimeric ligand binding molecules, include the VEGF-trap molecules described in, for example, WO 2000/75319, WO 2005/000895 and WO 2006/088650. A preferred heterologous binding unit comprises Ig-domain 2 from VEGFR-1 (R1 D2) and Ig-domain 3 from VEGFR-2 (R2D3), optionally fused to an Fc portion an immunoglobulin. In one embodiment is envisaged a chimeric molecule comprising a ligand binding polypeptide of the present invention linked to an Fc portion of an immunoglobulin operably linked with a R1D2R2D3 binding unit fused to an Fc portion an immunoglobulin. The two binding units are operably linked via disulphide bonding between the two Fc portions.

Linkers

While Ig-like domains of human VEGFR-3 may be directly attached to one another (via a peptide, disulfide or other type of covalent bond) or to Ig-like domains of other receptors, the ligand binding molecules described herein optionally further comprise a (one or more) linker that connects together two or more different binding units, e.g., VEGFR-3 ECD fragments with another VEGFR-3 ECD fragment, or even a copy of itself. A linker may also link a binding unit to other substituents described herein. In some embodiments, the linker comprises a heterologous polypeptide. For example, in some embodiments, the linker comprises a peptide that links the binding units to form a single continuous peptide that can be expressed as a single ligand binding molecule. Linkers may be chosen such that they are less likely to induce an allergic reaction. Polysaccharides or other moieties also may be used to link binding units to form a ligand binding molecule.

More than one linker may be used per ligand binding molecule. The linker may be selected for optimal conformational (steric) freedom between the various ligand binding units to allow them to interact with each other if desired, e.g., to form dimers, or to allow them to interact with ligand. The linker may be linear such that consecutive binding units are linked in series, or the linker may serve as a scaffold to which various binding units are attached, e.g., a branched linker. A linker may also have multiple branches, e.g., as disclosed in Tam, J. Immunol. Methods 196:17 (1996). Binding units may be attached to each other or to the linker scaffold via N-terminal amino groups, C-terminal carboxyl groups, side chains, chemically modified groups, side chains, or other means.

Linker peptides may be designed to have sequences that permit desired characteristics. For example, the use of glycyl residues allow for a relatively large degree of conformational freedom, whereas a proline would tend to have the opposite effect. Peptide linkers may be chosen so that they achieve particular secondary and tertiary structures, e.g., alpha helices, beta sheets or beta barrels. Quaternary structure can also be utilized to create linkers that join two binding units together non-covalently. For example, fusing a protein domain with a hydrophobic face to each binding unit may permit the joining of the two binding units via the interaction between the hydrophobic interaction of the two molecules. In some embodiments, the linker may provide for polar interactions. For example, a leucine zipper domain of the proto-oncoproteins Myc and Max, respectively, may be used. Luscher and Larsson, *Ongogene* 18:2955-2966 (1999). In some embodiments, the linker allows for the formation of a salt bridge or disulfide bond. Linkers may comprise non-naturally occurring amino acids, as well as naturally occurring amino acids that are not naturally incorporated into a polypeptide. In some embodiments, the linker comprises a coordination complex between a metal or other ion and various residues from the multiple peptides joined thereby.

Linear peptide linkers of at least one amino acid residue are contemplated. In some embodiments the linker has more than 10,000 residues. In some embodiments the linker has from 1-10,000 residues, 1-1000 residues, 1-100 residues, 1-50 residues, or 1-10 residues. In some embodiments, the linear peptide linker comprises residues with relatively inert side chains. Peptide linker amino acid residues need not be linked entirely or at all via alpha-carboxy and alpha-amino groups. That is, peptides may be linked via side chain groups of various residues.

The linker may affect whether the polypeptide(s) to which it is fused to is able to dimerize to each other or to another polypeptide. The linker serves a number of functions. Native receptor monomers restrained to the roughly two-dimensional plane of the cell membrane enjoy a relatively high local concentration and in the availability of co-receptors (binding units), increasing the probability of finding a partner. Receptors free in solution lacking such advantages may be aided by a linker that increases the effective concentration of the monomers.

In some embodiments, a ligand binding molecule may comprise more than one type of linker. Suitable linkers may also comprise the chemical modifications discussed above.

The ligand binding molecules described herein may comprise an additional N-terminal amino acid residue, preferably a methionine. Indeed, depending on the expression system and conditions, polypeptides may be expressed in a recombinant host cell with a starting Methionine. This additional amino acid may then be either maintained in the resulting recombinant protein, or eliminated by means of an exopeptidase, such as Methionine Aminopeptidase, according to methods disclosed in the literature (Van Valkenburgh H A and Kahn R A, Methods Enzymol. (2002) 344:186-93; Ben-Bassat A, Bioprocess Technol. (1991) 12:147-59).

Substituents and Other Chemical Modifications

The ligand binding molecules described herein are optionally chemically modified with various substituents. Such modifications preferably do not substantially reduce the growth factor binding affinities or specificities of the ligand binding molecule. Rather, the chemical modifications impart additional desirable characteristics as discussed herein. Chemical modifications may take a number of different forms such as heterologous peptides, polysaccharides, lipids, radioisotopes, non-standard amino acid resides and nucleic acids, metal chelates, and various toxins.

The receptor fragments (or "binding units" or "component domains") and ligand binding molecules described herein are optionally fused to heterologous fusion partners such as heterologous polypeptides to confer various properties, e.g., increased solubility, modulation of clearance, targeting to particular cell or tissue types. In some embodiments, the receptor fragment is linked to an Fc domain of IgG or other immunoglobulin. In some embodiments, a receptor fragment is fused to alkaline phosphatase (AP). Methods for making Fc or AP fusion constructs are found in WO 02/060950. By fusing the ligand binding polypeptide or molecule with protein domains that have specific properties (e.g. half-life, bioavailability, interaction partners) it is possible to confer these properties to the ligand binding molecule (e.g., the molecules is engineered to have a specific tissue distribution or specific biological half-life). In some embodiments, ligand binding molecule includes a co-receptor and a VEGFR fragment.

The particular fusion partner (e.g., heterologous polypeptide) used in a particular ligand binding molecule can influence whether or not a VEGR-3 fragment will dimerize, which in turn may affect ligand binding.

For substituents such as an Fc region of human IgG, the fusion can be fused directly to a ligand binding molecule or fused through an intervening sequence. For example, a human IgG hinge, CH2 and CH3 region may be fused at either the N-terminus or C-terminus of a ligand binding molecule to attach the Fc region. The resulting Fc-fusion construct enables purification via a Protein A affinity column (Pierce, Rockford, Ill.). Peptide and proteins fused to an Fc region can exhibit a substantially greater half-life in vivo than the unfused counterpart. A fusion to an Fc region allows for dimerization/multimerization of the fusion polypeptide. The Fc region may be a naturally occurring Fc region, or may be modified for superior characteristics, e.g., therapeutic qualities, circulation time, reduced aggregation.

Polypeptides can be modified, for instance, by glycosylation, amidation, carboxylation, or phosphorylation, or by the creation of acid addition salts, amides, esters, in particular C-terminal esters, and N-acyl derivatives. Ig-like domains I-III of VEGFR-3 comprises 5 putative N-glycosylation sites (referred to herein as N1, N2, N3, N4 and N5 sequons or regions of VEGFR-3, respectively). N1 corresponds to amino acids 33-35 of SEQ ID NO: 2; N2 corresponds to amino acids 104-106 of SEQ ID NO: 2; N3 corresponds to amino acids 166-168 of SEQ ID NO: 2; N4 corresponds to amino acids 251-253 of SEQ ID NO: 2 and N5 corresponds to amino acids 299-301 of SEQ ID NO: 2. In some embodiments, a ligand binding molecule described herein comprises a modification in the N2 region of the molecule. For example, in some embodiments, the amino acid in the ligand binding molecule corresponding to position 104 of SEQ ID NO: 2 is deleted and replaced with another amino acid. Conservative substitutions are preferred. In some embodiments, the amino acid corresponding to position 104 of SEQ ID NO: 2 is deleted and replaced with an amino acid selected from the group consisting of glutamine, aspartate, glutamate, arginine and lysine. In still other variations, position 106 is substituted to eliminate the N2 sequon. In embodiments where the N2 sequon of SEQ ID NO: 2 is modified as described above, the N1, N3, N4 and N5 sequons of SEQ ID NO: 2 are preferably unmodified.

The proteins also can be modified to create peptide derivatives by forming covalent or noncovalent complexes with other moieties. Covalently bound complexes can be prepared by linking the chemical moieties to functional groups on the side chains of amino acids of the polypeptides, or at the N- or C-terminus.

Polypeptides can be conjugated to a reporter group, including, but not limited to a radiolabel, a fluorescent label, an enzyme (e.g., that catalyzes a calorimetric or fluorometric reaction), a substrate, a solid matrix, or a carrier (e.g., biotin or avidin). Examples of analogs are described in WO 98/28621 and in Olofsson, et al., *Proc. Nat'l. Acad. Sci. USA,* 95:11709-11714 (1998), U.S. Pat. Nos. 5,512,545, and 5,474,982; U.S. Patent Application Nos. 20020164687 and 20020164710.

Cysteinyl residues most commonly are reacted with haloacetates (and corresponding amines), such as chloroacetic acid or chloroacetamide, to give carboxymethyl or carbocyamidomethyl derivatives. Cysteinyl residues also are derivatized by reaction with bromotrifluoroacetone, α-bromo-β(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, orchloro-7-nitrobenzo-2-oxa-1,3-diazole.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylissurea; 2,4 pentanedione; and transaminase catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pK of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using 125I or 131I to prepare labeled proteins for use in radioimmunoassay.

Carboxyl side groups (aspartyl or glutamyl) are selectively modified by reaction with carbodiimides (R1) such as 1-cyclohexyl-3-(2-morpholinyl-(4-ethyl) carbodiimide or 1-ethyl-3 (4 azonia 4,4-dimethylpentyl)carbodiimide. Furthermore, aspartyl and glutamyl residues are converted to asparaginyl and glutaminyl residues by reaction with ammonium ions.

Derivatization with bifunctional agents is useful for cross-linking the ligand binding molecule to water-insoluble support matrixes. Such derivation may also provide the linker that may connect adjacent binding elements in a ligand binding molecule, or a binding elements to a heterologous peptide, e.g., a Fc fragment. Commonly used crosslinking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl) dithio] propioimidate yield photoactivatable intermediates that are capable of forming cross links in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440, incorporated herein by reference, are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecule Properties*, W. H. Freeman & Co., San Francisco, pp. 79-86, 1983), acetylation of the N-terminal amine, and, in some instances, amidation of the C-terminal carboxyl groups. Such derivatives are chemically modified polypeptide compositions in which the ligand binding molecule polypeptide is linked to a polymer. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. The polymer may be of any molecular weight, and may be branched or unbranched. Included within the scope of the ligand binding molecule polypeptide polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water soluble polymer, some molecules will weigh more, some less, than the stated molecular weight). The average molecular weight of each polymer is between about 5 kDa and about 50 kDa, more preferably between about 12 kDa to about 40 kDa and most preferably between about 20 kDa to about 35 kDa.

Suitable water soluble polymers or mixtures thereof include, but are not limited to, N-linked or O-linked carbohydrates, sugars, phosphates, carbohydrates; sugars; phosphates; polyethylene glycol (PEG) (including the forms of PEG that have been used to derivatize proteins, including mono-(C1-C10) alkoxy- or aryloxy-polyethylene glycol); monomethoxy-polyethylene glycol; dextran (such as low molecular weight dextran, of, for example about 6 kD), cellulose; cellulose; other carbohydrate-based polymers, poly-(N-vinyl pyrrolidone)polyethylene glycol, propylene glycol homopolymers, a polypropylene oxide/ethylene oxide co-polymer, polyoxyethylated polyols (e.g., glycerol) and polyvinyl alcohol. Also encompassed by the present invention are bifunctional crosslinking molecules which may be used to prepare covalently attached multimers.

In general, chemical derivatization may be performed under any suitable condition used to react a protein with an activated polymer molecule. Methods for preparing chemical derivatives of polypeptides will generally comprise the steps of (a) reacting the polypeptide with the activated polymer molecule (such as a reactive ester or aldehyde derivative of the polymer molecule) under conditions whereby the ligand binding molecule becomes attached to one or more polymer molecules, and (b) obtaining the reaction product(s). The optimal reaction conditions will be determined based on known parameters and the desired result. For example, the larger the ratio of polymer molecules:protein, the greater the amount of attached polymer molecule. In one embodiment, the ligand binding molecule polypeptide derivative may have a single polymer molecule moiety at the amino terminus. (See, e.g., U.S. Pat. No. 5,234,784).

A particularly preferred water-soluble polymer for use herein is polyethylene glycol (PEG). As used herein, polyethylene glycol is meant to encompass any of the forms of PEG that can be used to derivatize other proteins, such as mono-(C1-C10) alkoxy- or aryloxy-polyethylene glycol. PEG is a linear or branched neutral polyether, available in a broad range of molecular weights, and is soluble in water and most organic solvents. PEG is effective at excluding other polymers or peptides when present in water, primarily through its high dynamic chain mobility and hydrophilic nature, thus creating a water shell or hydration sphere when attached to other proteins or polymer surfaces. PEG is nontoxic, non-immunogenic, and approved by the Food and Drug Administration for internal consumption.

Proteins or enzymes when conjugated to PEG have demonstrated bioactivity, non-antigenic properties, and decreased clearance rates when administered in animals. F. M. Veronese et al., Preparation and Properties of Monomethoxypoly(ethylene glycol)-modified Enzymes for Therapeutic Applications, in J. M. Harris ed., *Poly(Ethylene Glycol) Chemistry—Biotechnical and Biomedical Applications,* 127-36, 1992, incorporated herein by reference. These phenomena are due to the exclusion properties of PEG in preventing recognition by the immune system. In addition, PEG has been widely used in surface modification procedures to decrease protein adsorption and improve blood compatibility. S. W. Kim et al., *Ann. N.Y. Acad. Sci.* 516: 116-30 1987; Jacobs et al., *Artif. Organs* 12: 500-501, 1988; Park et al., *J. Poly. Sci, Part A* 29:1725-31, 1991, incorporated herein by reference. Hydrophobic polymer surfaces, such as polyurethanes and polystyrene can be modified by the grafting of PEG (MW 3,400) and employed as non-thrombogenic surfaces. Surface properties (contact angle) can be more consistent with hydrophilic surfaces, due to the hydrating effect of PEG. More importantly, protein (albumin and other plasma proteins) adsorption can be greatly reduced, resulting from the high chain motility, hydration sphere, and protein exclusion properties of PEG.

PEG (MW 3,400) was determined as an optimal size in surface immobilization studies, Park et al., *J. Biomed. Mat. Res.* 26:739-45, 1992, while PEG (MW 5,000) was most beneficial in decreasing protein antigenicity. (F. M. Veronese et al., In J. M. Harris, et al., *Poly(Ethylene Glycol) Chemistry—Biotechnical and Biomedical Applications,* 127-36.)

Methods for preparing pegylated ligand binding molecules will generally comprise the steps of (a) reacting the polypeptide with polyethylene glycol (such as a reactive ester or aldehyde derivative of PEG) under conditions whereby the ligand molecule becomes attached to one or more PEG groups, and (b) obtaining the reaction product(s). In general, the optimal reaction conditions for the acylation reactions will be determined based on known parameters and the desired result. For example, the larger the ratio of PEG:protein, the greater the percentage of poly-pegylated product. In some embodiments, the ligand binding molecule will have a single PEG moiety at the N-terminus. See U.S. Pat. No. 8,234,784, herein incorporated by reference. In some embodiments, a ligand binding molecule described herein optionally comprises at least one PEG moiety attached to the molecule. For example, in some embodiments, PEG of about 20-40 kDa is attached to the amino terminus of the ligand binding molecule.

Derivatized ligand binding molecules disclosed herein may have additional activities, enhanced or reduced biological activity, or other characteristics, such as increased or decreased half-life, as compared to the non-derivatized molecules.

Polynucleotides Encoding Ligand Binding Molecules and Expression Systems

The invention comprises not only the ligand binding molecules, binding units, and polypeptides described herein, but also nucleic acids encoding such molecules, vectors comprising such molecules and host cells comprising such vectors. Methods employing any of the molecules, units, polypeptides, nucleic acids, vectors and hosts cells are all considered aspects of the invention.

An exemplary human VEGFR-3 coding sequence is set forth in SEQ ID NO: 1, and fragments of SEQ ID NO: 1 (modified at the N2 sequon) are contemplated as coding sequences for ligand binding polypeptides described herein. (For example, fragments encoding all or portions of the VEGFR-3 ECD are contemplated.) Due to the well-known degeneracy of the genetic code, numerous equivalent coding sequences are possible for any polypeptide-encoding sequence, and all such equivalents are contemplated as aspects of the invention.

Furthermore, just as amino acid sequence variation from VEGFR-3 wild type ECD is contemplated, as described above, nucleic acid sequence variation is also contemplated. The nucleic acid sequence variation can be characterized as percent identity relative to SEQ ID NO: 1 (e.g. at least 80, 85, 90, 92, 93, 94, 95, 96, 97, 98, or 99% identity).

Nucleotide sequence variation also can be characterized by ability to hybridize to the complement of a preferred coding sequence. Nucleic acid molecules include those molecules which comprise nucleotide sequences which hybridize under moderately or highly stringent conditions as defined herein with the ECD-encoding sequence of the nucleic acid molecule set forth in SEQ ID NO: 1, or of a molecule encoding a polypeptide, which polypeptide comprises the receptor tyrosine kinase amino acids sequence set forth in SEQ ID NOs: 2 and 3, or of a nucleic acid fragment as described herein, or of a nucleic acid fragment encoding a polypeptide as described herein.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, Fritsch & Maniatis, Molecular Cloning: A Laboratory Manual, 2nd Ed., Cold Spring Harbor Laboratory, (Cold Spring Harbor, N.Y. 1989); and Anderson et al., Nucleic Acid Hybridization: a Practical approach, Ch. 4, IRL Press Limited (Oxford, England). Limited, Oxford, England. Other agents may be included in the hybridization and washing buffers for the purpose of reducing non-specific and/or background hybridization. Examples are 0.1% bovine serum albumin, 0.1% polyvinylpyrrolidone, 0.1% sodium pyrophosphate, 0.1% sodium dodecylsulfate ($NaDodSO_4$ or SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH. See Anderson et al., Nucleic Acid Hybridization: a Practical Approach, Ch. 4, IRL Press Limited (Oxford, England).

Factors affecting the stability of a DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$Tm(°\ C.)=81.5+16.6(\log\ [Na+])+0.41(\%\ G+C)-600/N-0.72(\%\ formamide)$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately" stringent conditions"" refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate and 20% formamide at 37-50° C. By way of example, a "moderately stringent" condition of 50° C. in 0.015 M sodium ion will allow about a 21% mismatch.

A good estimate of the melting temperature in 1M NaCl* for oligonucleotide probes up to about 20 nt is given by:

$$Tm=2°\ C.\ per\ A\text{-}T\ base\ pair+4°\ C.\ per\ G\text{-}C\ base\ pair$$

The sodium ion concentration in 6× salt sodium citrate (SSC) is 1 M. See Suggs et al., Developmental Biology Using Purified Genes, p. 683, Brown and Fox (eds.) (1981).

High stringency washing conditions for oligonucleotides are usually at a temperature of 0-5° C. below the Tm of the oligonucleotide in 6×SSC, 0.1% SDS.

Differences in the nucleic acid sequence may result in conservative and/or non-conservative modifications of the amino acid sequence relative to the amino acid sequence of SEQ ID NO: 2 or SEQ ID NO: 3. The invention is also directed to an isolated and/or purified DNA that corresponds to, or that hybridizes under stringent conditions with, any one of the foregoing DNA sequences.

A nucleic acid molecule encoding all or part of a polypeptide of the invention such as a ligand binding molecule or binding unit described herein can be made in a variety of ways, including, without limitation, chemical synthesis, cDNA or genomic library screening, expression library screening, and/or PCR amplification of cDNA or genomic DNA. These methods and others useful for isolating such DNA are set forth, for example, by Sambrook, et al., "Molecular Cloning: A Laboratory Manual," Cold Spring Harbor Laboratory Press, Cold Spring Harbor, N.Y. (1989), by Ausubel, et al., eds., "Current Protocols In Molecular Biology," Current Protocols Press (1994), and by Berger and Kimmel, "Methods In Enzymology: Guide To Molecular Cloning Techniques," vol. 152, Academic Press, Inc., San Diego, Calif. (1987). Preferred nucleic acid sequences are mammalian sequences, such as human, rat, and mouse.

Chemical synthesis of nucleic acid molecules can be accomplished using methods well known in the art, such as those set forth by Engels, et al., *Angew. Chem. Intl. Ed.*, 28:716-734 (1989). These methods include, inter alia, the phosphotriester, phosphoramidite and H-phosphonate methods of nucleic acid synthesis. Nucleic acids larger than about 100 nucleotides in length can be synthesized as several fragments, each fragment being up to about 100 nucleotides in length. The fragments can then be ligated together, as described below, to form the full length nucleic acid of interest. A preferred method is polymer-supported synthesis using standard phosphoramidite chemistry.

The term "vector" refers to a nucleic acid molecule amplification, replication, and/or expression vehicle, often derived from or in the form of a plasmid or viral DNA or RNA system, where the plasmid or viral DNA or RNA is functional in a selected host cell, such as bacterial, yeast, plant, invertebrate, and/or mammalian host cells. The vector may remain independent of host cell genomic DNA or may integrate in whole or in part with the genomic DNA. The vector will contain all necessary elements so as to be functional in any host cell it is compatible with. Such elements are set forth below.

Where nucleic acid encoding a polypeptide or fragment thereof has been isolated, it is preferably inserted into an amplification and/or expression vector in order to increase the copy number of the gene and/or to express the encoded polypeptide in a suitable host cell and/or to transform cells in a target organism (to express the polypeptide in vivo). Numerous commercially available vectors are suitable, though "custom made" vectors may be used as well. The vector is selected to be functional in a particular host cell or host tissue (i.e., for replication and/or expression). The polypeptide or fragment thereof may be amplified/expressed in prokaryotic and/or eukaryotic host cells, e.g., yeast, insect (baculovirus systems), plant, and mammalian cells. Selection of the host cell will depend at least in part on whether the polypeptide or fragment thereof is to be glycosylated. If so, yeast, insect, or mammalian host cells are preferable; yeast and mammalian cells will glycosylate the polypeptide if a glycosylation site is present on the amino acid sequence.

Typically, the vectors used in any of the host cells will contain 5' flanking sequence and other regulatory elements such as an enhancer(s), a promoter, an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Optionally, the vector may contain a "tag" sequence, i.e., an oligonucleotide sequence located at the 5' or 3' end of the coding sequence that encodes polyHis (such as hexaHis) or another small immunogenic sequence. This tag will be expressed along with the protein, and can serve as an affinity tag for purification of the polypeptide from the host cell. Optionally, the tag can subsequently be removed from the purified polypeptide by various means such as using a selected peptidase.

The vector/expression construct may optionally contain elements such as a 5' flanking sequence, an origin of replication, a transcription termination sequence, a selectable marker sequence, a ribosome binding site, a signal sequence, and one or more intron sequences. The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native polypeptide 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

A transcription termination element is typically located 3' to the end of the polypeptide coding sequence and serves to terminate transcription of the polypeptide. Usually, the transcription termination element in prokaryotic cells is a G-C rich fragment followed by a poly T sequence. Such elements can be cloned from a library, purchased commercially as part of a vector, and readily synthesized.

Selectable marker genes encode proteins necessary for the survival and growth of a host cell in a selective culture medium. Typical selectable marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media.

A ribosome binding element, commonly called the Shine-Dalgarno sequence (prokaryotes) or the Kozak sequence (eukaryotes), is necessary for translation initiation of mRNA. The element is typically located 3' to the promoter and 5' to the coding sequence of the polypeptide to be synthesized. The Shine-Dalgarno sequence is varied but is typically a polypurine (i.e., having a high A-G content). Many Shine-Dalgarno sequences have been identified, each of which can be readily synthesized using methods set forth above.

All of the elements set forth above, as well as others useful in this invention, are well known to the skilled artisan and are described, for example, in Sambrook, et al., "Molecular Cloning: A Laboratory Manual," Cold Spring Harbor Laboratory Press, Cold Spring Harbor, N.Y. (1989) and Berger, et al., eds., "Guide To Molecular Cloning Techniques," Academic Press, Inc., San Diego, Calif. (1987).

For those embodiments of the invention where the recombinant polypeptide is to be secreted, a signal sequence is preferably included to direct secretion from the cell where it is synthesized. Typically, the polynucleotide encoding the signal sequence is positioned at the 5' end of the coding region. Many signal sequences have been identified, and any of them that are functional in a target cell or species may be used in conjunction with the transgene.

In many cases, gene transcription is increased by the presence of one or more introns on the vector. The intron may be naturally-occurring, especially where the transgene is a full length or a fragment of a genomic DNA sequence. The intron may be homologous or heterologous to the transgene and/or to the transgenic mammal into which the gene will be inserted. The position of the intron with respect to the promoter and the transgene is important, as the intron must be transcribed to be effective. A preferred position for an intron is 3' to the transcription start site, and 5' to the polyA transcription termination sequence. For cDNA transgenes, an intron is placed on one side or the other (i.e., 5' or 3') of the transgene coding sequence. Any intron from any source, including any viral, prokaryotic and eukaryotic (plant or animal) organisms, may be used to express the polypeptide, provided that it is compatible with the host cell(s) into which it is inserted. Also included herein are synthetic introns. Optionally, more than one intron may be used in the vector.

Exemplary vectors for recombinant expression are those that are compatible with bacterial, insect, and mammalian host cells. Such vectors include, inter alia, pCRII (Invitrogen Company, San Diego, Calif.), pBSII (Stratagene Company, La Jolla, Calif.), and pETL (BlueBacII; Invitrogen).

After the vector has been constructed and a nucleic acid has been inserted into the proper site of the vector, the completed vector may be inserted into a suitable host cell for amplification and/or polypeptide expression. Commonly used include: Prokaryotic cells such as gram negative or gram positive bacteria, i.e., any strain of E. coli, Bacillus, Streptomyces, Saccharomyces, Salmonella, and the like; eukaryotic cells such as CHO (Chinese hamster ovary) cells; human kidney 293 cells; COS-7 cells; insect cells such as Sf4, Sf5, Sf9, and Sf21 and High 5 (all from the Invitrogen Company, San Diego, Calif.); plant cells and various yeast cells such as Saccharomyces and Pichia. Any transformable or transfectable cell or cell line derived from any organism such as bacteria, yeast, fungi, monocot and dicot plants, plant cells, and animals are suitable.

Insertion (also referred to as "transformation" or "transfection") of the vector into the selected host cell may be accomplished using such methods as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook, et al., supra.

The host cells containing the vector (i.e., transformed or transfected) may be cultured using standard media well known to the skilled artisan. The media will usually contain all nutrients necessary for the growth and survival of the cells. Suitable media for culturing E. coli cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of polypeptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or binding assays.

If the polypeptide has been designed to be secreted from the host cells, the majority of polypeptide will likely be found in the cell culture medium. If, however, the polypeptide is not secreted from the host cells, it will be present in the cytoplasm (for eukaryotic, gram positive bacteria, and insect host cells) or in the periplasm (for gram negative bacteria host cells).

For intracellular polypeptides, the host cells are first disrupted mechanically or osmotically to release the cytoplasmic contents into a buffered solution. The polypeptide is then isolated from this solution.

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type. A cell line substantially enriched in such cells can be then isolated to provide a stable cell line.

A particularly preferred method of high-yield production of a recombinant polypeptide of the present invention is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

Purification of the polypeptide from solution can be accomplished using a variety of techniques. If the polypeptide has been synthesized such that it contains a tag such as hexahistidine or other small peptide at either its carboxyl or amino terminus, it may essentially be purified in a one-step process by passing the solution through an affinity column where the column matrix has a high affinity for the tag or for the polypeptide directly (i.e., a monoclonal antibody specifically recognizing the polypeptide). For example, polyhistidine binds with great affinity and specificity to nickel, thus an affinity column of nickel (such as the Qiagen nickel columns) can be used for purification of the His-tagged polypeptide. (See, for example, Ausubel, et al., eds., "Current Protocols In Molecular Biology," Section 10.11.8, John Wiley & Sons, New York (1993)).

The strong affinity a ligand for its receptor permits affinity purification of ligand binding molecules, and ligand binding molecules using an affinity matrix comprising a complementary binding partner. Affinity chromatography may be employed, e.g., using either natural binding partners (e.g., a ligand when purifying a ligand binding molecule with affinity for the same) or antibodies generated using standard procedures (e.g., immunizing a mouse, rabbit or other animal with an appropriate polypeptide). The peptides of the present invention may be used to generate such antibodies. Known antibodies or antibodies to known growth factor receptors may be employed when they share an epitope with a targeted ligand binding molecule.

In addition, other well-known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity. Preferred methods for purification include polyhistidine tagging and ion exchange chromatography in combination with preparative isoelectric focusing.

Polypeptide found in the periplasmic space of the bacteria or the cytoplasm of eukaryotic cells, the contents of the periplasm or cytoplasm, including inclusion bodies (bacteria) if the processed polypeptide has formed such complexes, can be extracted from the host cell using any standard technique known to the skilled artisan. For example, the host cells can be lysed to release the contents of the periplasm by French press, homogenization, and/or sonication. The homogenate can then be centrifuged.

If the polypeptide has formed inclusion bodies in the periplasm, the inclusion bodies can often bind to the inner and/or outer cellular membranes and thus will be found primarily in the pellet material after centrifugation. The pellet material can then be treated with a chaotropic agent such as guanidine or urea to release, break apart, and solubilize the inclusion bodies. The solubilized polypeptide can then be analyzed using gel electrophoresis, immunoprecipitation or the like. If it is desired to isolate the polypeptide, isolation may be accomplished using standard methods such as those set forth below and in Marston, et al., *Meth. Enz.*, 182:264-275 (1990).

Gene Therapy

In some embodiments, polynucleotides of the invention further comprise additional sequences to facilitate the gene therapy. In one embodiment, a "naked" transgene encoding a ligand binding molecule described herein (i.e. a transgene without a viral, liposomal, or other vector to facilitate transfection) is employed for gene therapy.

Vectors also are useful for "gene therapy" treatment regimens, wherein a polynucleotide that encodes a ligand binding polypeptide or molecule is introduced into a subject in need of inhibition of neovascularization, in a form that causes cells in the subject to express the ligand binding molecule of the invention in vivo. Gene therapy aspects that are described in U.S. Patent Publication No. 2002/0151680 and WO 01/62942 both of which are incorporated herein by reference, also are applicable herein.

Any suitable vector may be used to introduce a polynucleotide that encodes a ligand binding molecule described herein, into the host. Exemplary vectors that have been described in the literature include replication deficient retroviral vectors, including but not limited to lentivirus vectors (Kim et al., J. Virol., 72(1): 811-816, 1998; Kingsman & Johnson, Scrip Magazine, October, 1998, pp. 43-46); adeno-associated viral (AAV) vectors (U.S. Pat. Nos. 5,474, 935I; 5,139,941; 5,622,856; 5,658,776; 5,773,289; 5,789, 390; 5,834,441; 5,863,541; 5,851,521; 5,252,479; Gnatenko et al., J. Invest. Med., 45: 87-98, 1997); adenoviral (AV) vectors (U.S. Pat. Nos. 5,792,453; 5,824,544; 5,707,618; 5,693,509; 5,670,488; 5,585,362; Quantin et al., Proc. Natl. Acad. Sci. USA, 89: 2581-2584, 1992; Stratford Perricadet et al., J. Clin. Invest., 90:626-630, 1992; and Rosenfeld et al., Cell, 68: 143-155, 1992); an adenoviral adeno-associated viral chimeric (U.S. Pat. No. 5,856,152) or a vaccinia viral or a herpesviral (U.S. Pat. Nos. 5,879,934; 5,849,571; 5,830, 727; 5,661,033; 5,328,688); Lipofectin mediated gene transfer (BRL); liposomal vectors (U.S. Pat. No. 5,631,237, Liposomes comprising Sendai virus proteins); and combinations thereof. All of the foregoing documents are incorporated herein by reference in their entireties.

Other non-viral delivery mechanisms contemplated include, but are not limited to, calcium phosphate precipitation (Graham and Van Der Eb, Virology, 52:456-467, 1973; Chen and Okayama, Mol. Cell Biol., 7:2745-2752, 1987; Rippe et al., Mol. Cell Biol., 10:689-695, 1990) DEAE-dextran (Gopal, Mol. Cell Biol., 5:1188-1190, 1985), electroporation (Tur-Kaspa et al., Mol. Cell Biol., 6:716-718, 1986; Potter et al., Proc. Nat. Acad. Sci. USA, 81:7161-7165, 1984), direct microinjection (Harland and Weintraub, J. Cell Biol., 101:1094-1099, 1985.), DNA-loaded liposomes (Nicolau and Sene, Biochim. Biophys. Acta, 721: 185-190, 1982; Fraley et al., Proc. Natl. Acad. Sci. USA, 76:3348-3352, 1979; Feigner, Sci Am. 276(6):102-6, 1997; Feigner, Hum Gene Ther. 7(15):1791-3, 1996), cell sonication (Fechheimer et al., Proc. Natl. Acad. Sci. USA, 84:8463-8467, 1987), gene bombardment using high velocity microprojectiles (Yang et al., Proc. Natl. Acad. Sci USA, 87:9568-9572, 1990), and receptor-mediated transfection (Wu and Wu, J. Biol. Chem., 262:4429-4432, 1987; Wu and Wu, Biochemistry, 27:887-892, 1988; Wu and Wu, Adv. Drug Delivery Rev., 12:159-167, 1993).

The expression construct (or indeed a ligand binding molecule described herein) may be entrapped in a liposome. Liposomes are vesicular structures characterized by a phospholipid bilayer membrane and an inner aqueous medium. Multi-lamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, In: Liver diseases, targeted diagnosis and therapy using specific receptors and ligands, Wu G, Wu C ed., New York: Marcel Dekker, pp. 87-104, 1991). The addition of DNA to cationic liposomes causes a topological transition from liposomes to optically birefringent liquid-crystalline condensed globules (Radler et al., Science, 275 (5301):810-4, 1997). These DNA-lipid complexes are potential non-viral vectors for use in gene therapy and delivery.

Liposome-mediated nucleic acid delivery and expression of foreign DNA in vitro has been successful. Also contemplated in the present invention are various commercial approaches involving "lipofection" technology. In certain embodiments of the invention, the liposome may be complexed with a hemagglutinating virus (HVJ). This has been shown to facilitate fusion with the cell membrane and promote cell entry of liposome-encapsulated DNA (Kaneda et al., Science, 243:375-378, 1989). In other embodiments, the liposome may be complexed or employed in conjunction with nuclear nonhistone chromosomal proteins (HMG-1) (Kato et al., J. Biol. Chem., 266:3361-3364, 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., Nature, 327:70-73, 1987). Several devices for accelerating small particles have been developed. One such device relies on a high voltage discharge to generate an electrical current, which in turn provides the motive force (Yang et al., Proc. Natl. Acad. Sci USA, 87:9568-9572, 1990). The microprojectiles used have consisted of biologically inert substances such as tungsten or gold beads.

In embodiments employing a viral vector, preferred polynucleotides still include a suitable promoter and polyadenylation sequence as described above. Moreover, it will be readily apparent that, in these embodiments, the polynucleotide further includes vector polynucleotide sequences (e.g., adenoviral polynucleotide sequences) operably connected to the sequence encoding a polypeptide of the invention.

Therapeutic Uses of the Ligand Binding Molecules

The ligand binding polypeptides and molecules described herein, and the polynucleotides and vectors that encode them, are useful for inhibiting cellular processes that are mediated through endothelial growth factors inducing signal transduction through VEGFR-2 or VEGFR-3, and have indications for prophylaxis or therapy of disorders associated with aberrant angiogenesis and/or lymphangiogenesis (e.g., various ocular disorders and cancer) that is stimulated by the actions of such growth factors on these receptors. The ligand binding polypeptides and molecules described herein, and the polynucleotides and vectors that encode them, are therapeutically useful for treating or preventing any disease of condition which is improved, ameliorated, inhibited or prevented by the removal, inhibition or reduction of VEGF-C and/or VEGF-D. A non-exhaustive list of specific conditions improved by inhibition or reduction of VEGF-C and/or VEGF-D (and in particular at least VEGF-C) include: clinical conditions that are characterized by excessive vascular endothelial cell proliferation, vascular permeability, edema or inflammation such as brain edema associated with injury, stroke or tumor; edema associated with inflammatory disorders such as psoriasis or arthritis, including rheumatoid arthritis; asthma; generalized edema associated with burns; ascites and pleural effusion associated with tumors, inflammation or trauma; chronic airway inflammation; capillary leak syndrome; sepsis; kidney disease associated with increased leakage of protein; and eye disorders such as age related macular degeneration and diabetic retinopathy.

Although for brevity many of the methods are described below with respect to compositions comprising a ligand binding molecule, it should be understood that practice of the invention with any of the constructs described herein (ligand binding polypeptides, molecules, and constructs, and polynucleotides that encode them, dimers and other multimers, etc.) is contemplated.

An exemplary therapeutic use is a method of inhibiting neovascularization in a subject in need thereof comprising administering to the subject a composition comprising a ligand binding molecule described herein, in an amount effective to inhibit neovascularization in the subject. In some embodiments, the neovascularization comprises choroidal or retinal neovascularization. In some embodiments, the neovascularization is tumor neovascularization that occurs in malignant cancers and other tumors.

In another aspect, described herein is a method of prophylaxis or therapy for an ocular disorder associated with neovascularization comprising administering to a subject in need of prophylaxis or therapy for the ocular disorder a composition comprising a ligand binding molecule described herein.

In another aspect, described herein is a method of prophylaxis or therapy for an ocular disorder which results in retinal edema comprising administering to a subject in need of prophylaxis or therapy for the ocular disorder or disease a composition comprising a ligand binding molecule described herein.

Examples of ocular disorders which may be treated include choroidal neovascularization, diabetic macular edema, age-related macular degeneration, proliferative diabetic retinopathy, retinal vein occlusion and corneal neovascularization/transplant rejection. Preferably, the amount of the ligand binding molecule employed is effective to inhibit the binding of VEGF-C and/or VEGF-D ligand to VEGFR-3 (and preferably also to VEGFR-2) or the stimulatory effect of VEGF-C and/or VEGF-D on VEGFR-3 (and preferably also VEGFR-2).

In one embodiment, the ocular disorder is age-related macular degeneration. Examples of age-related macular degeneration are non-neovascular (also known as "Dry") and neovascular (also known as "Wet") macular degeneration. In a preferred embodiment, the ocular disorder is wet age-related macular degeneration. Treating or preventing wet age-related macular degeneration also encompasses treating or preventing choroidal neovascularization or pigment epithelial detachment.

In one embodiment, the ocular disorder is polypoidal choroidal vasculopathy. Polypoidal choroidal vasculopathy is characterized by a lesion from an inner choroidal vascular network of vessels ending in an aneurysmal bulge or outward projection (Ciardella et al. (2004) Surv Ophthalmol. 49:25-37).

In one embodiment, the ocular disorder is a condition associated with choroidal neovascularization. Examples of conditions associated with choroidal neovascularization include a degenerative, inflammatory, traumatic or idiopathic condition. Treating or preventing a degenerative disorder associated with choroidal neovascularization also encompasses treating or preventing a heredodegenerative disorder. Examples of heredodegenerative disorders include vitelliform macular dystrophy, fundus flavimaculatus and optic nerve head drusen. Examples of degenerative conditions associated with choroidal neovascularization include myopic degeneration or angioid streaks. Treating or preventing an inflammatory disorder associated with choroidal neovascularization also encompasses treating or preventing ocular histoplasmosis syndrome, multifocal choroiditis, serpininous choroiditis, toxoplasmosis, toxocariasis, rubella, Vogt-Koyanagi-Harada syndrome, Behcet syndrome or sympathetic ophthalmia. Treating or preventing a traumatic disorder associated with choroidal neovascularization also encompasses treating or preventing choroidal rupture or a traumatic condition caused by intense photocoagulation.

In one embodiment, the ocular disorder is hypertensive retinopathy.

In one embodiment, the ocular disorder is diabetic retinopathy. Diabetic retinopathy can be non-proliferative or proliferative diabetic retinopathy. Examples of non-proliferative diabetic retinopathy include macular edema and macular ischemia.

In one embodiment, the ocular disorder is sickle cell retinopathy.

In one embodiment, the ocular disorder is a condition associated with peripheral retinal neovascularization. Examples of conditions associated with peripheral retinal neovascularization include ischemic vascular disease, inflammatory disease with possible ischemia, incontinentia pigmenti, retinitis pigmentosa, retinoschisis or chronic retinal detachment.

Examples of ischemic vascular disease include proliferative diabetic retinopathy, branch retinal vein occlusion, branch retinal arteriolar occlusion, carotid cavernous fistula, sickling hemoglobinopathy, non-sickling hemoglobinopathy, IRVAN syndrome (retinal vasculitic disorder characterized by idiopathic retinal vasculitis, an aneurysm, and neuroretinitis), retinal embolization, retinopathy of prematurity, familial exudative vitreoretinopathy, hyperviscosity syndrome, aortic arch syndrome or Eales disease. Examples of sickling hemoglobinopathy include SS hemoglobinopathy and SC hemoglobinopathy. Examples of non-sickling hemoglobinopathy include AC hemoglobinopathy and AS hemoglobinopathy. Examples of hyperviscosity syndrome include leukemia, Waldenstrom macroglobulinemia, multiple myeloma, polycythemia or myeloproliferative disorder.

Treating or preventing an inflammatory disease with possible ischemia also encompasses treating or preventing retinal vasculitis associated with systemic disease, retinal vasculitis associated with an infectious agent, uveitis or birdshot retinopathy. Examples of systemic diseases include systemic lupus erythematosis, Behcet's disease, inflammatory bowel disease, sarcoidosis, multiple sclerosis, Wegener's granulomatosis and polyarteritis nodosa. Examples of infectious agents include a bacterial agent that is the causative agent for syphilis, tuberculosis, Lyme disease or cat-scratch disease, a virus such as herpesvirus, or a parasite such as *Toxocara canis* or *Toxoplasma gondii*. Examples of uveitis include pars planitis or Fuchs uveitis syndrome.

In one embodiment, the ocular disorder is retinopathy of prematurity. Retinopathy of prematurity can result from abnormal growth of blood vessels in the vascular bed supporting the developing retina (Pollan C (2009) Neonatal Netw. 28:93-101).

In one embodiment, the ocular disorder is venous occlusive disease. Examples of venous occlusive disease include branch retinal vein occlusion and central retinal vein occlusion. A branch retinal vein occlusion can be a blockage of the portion of the circulation that drains the retina of blood. The blockage can cause back-up pressure in the capillaries, which can lead to hemorrhages and also to leakage of fluid and other constituents of blood.

In one embodiment, the ocular disorder is arterial occlusive disease. Examples of arterial occlusive disease include branch retinal artery occlusion, central retinal artery occlusion or ocular ischemic syndrome. A branch retinal artery occlusion (BRAO) can occur when one of the branches of the arterial supply to the retina becomes occluded.

In one embodiment, the ocular disorder is central serous chorioretinopathy (CSC). In one embodiment, CSC is characterized by leakage of fluid in the central macula.

In one embodiment, the ocular disorder is cystoid macular edema (CME). In one embodiment, CME affects the central retina or macula. In another embodiment, CME occurs after cataract surgery.

In one embodiment, the ocular disorder is retinal telangiectasia. In one embodiment, retinal telangiectasia is characterized by dilation and tortuosity of retinal vessels and formation of multiple aneurysms. Idiopathic JXT, Leber's miliary aneurysms, and Coats' disease are three types of retinal telangiectasias.

In one embodiment, the ocular disorder is arterial macroaneurysm.

In one embodiment, the ocular disorder is retinal angiomatosis. In one embodiment, retinal angiomatosis occurs when the ocular vessels form multiple angiomas.

In one embodiment, the ocular disorder is radiation-induced retinopathy (RIRP). In one embodiment, RIRP may display symptoms such as macular edema and nonproliferative and proliferative retinopathy.

In one embodiment, the ocular disorder is rubeosis iridis. In another embodiment, rubeosis iridis results in the formation of neovascular glaucoma. In another embodiment, rubeosis iridis is caused by diabetic retinopathy, central retinal vein occlusion, ocular ischemic syndrome, or chronic retinal detachment.

In one embodiment, the ocular disorder is a neoplasm. Examples of neoplams include an eyelid tumor, a conjunctival tumor, a choroidal tumor, an iris tumor, an optic nerve tumor, a retinal tumor, an infiltrative intraocular tumor or an orbital tumor. Examples of an eyelid tumor include basal cell carcinoma, squamous carcinoma, sebaceous carcinoma, malignant melanoma, capillary hemangioma, hydrocystoma, nevus or seborrheic keratosis. Examples of a conjunctival tumor include conjunctival Kaposi's sarcoma, squamous carcinoma, intraepithelial neoplasia of the conjunctiva, epibular dermoid, lymphoma of the conjunctiva, melanoma, pingueculum, or pterygium. Examples of a choroidal tumor include choroidal nevus, choroidal hemangioma, metastatic choroidal tumor, choroidal osteoma, choroidal melanoma, ciliary body melanoma or nevus of Ota. Examples of an iris tumor include anterior uveal metastasis, iris cyst, iris melanocytoma, iris melanoma, or pearl cyst of the iris. Examples of an optic nerve tumor include optic nerve melanocytoma, optic nerve sheath meningioma, choroidal melanoma affecting the optic nerve, or circumpapillary metastasis with optic neuropathy. Examples of a retinal tumor include retinal pigment epithelial (RPE) hypertrophy, RPE adenoma, RPE carcinoma, retinoblastoma, hamartoma of the RPE, or von Hippel angioma. Examples of an infiltrative intraocular tumor include chronic lymphocytic leukemia, infiltrative choroidopathy, or intraocular lymphoma. Examples of an orbital tumor include adenoid cystic carcinoma of the lacrimal gland, cavernous hemangioma of the orbit, lymphangioma of the orbit, orbital mucocele, orbital pseudotumor, orbital rhabdomyosarcoma, periocular hemangioma of childhood, or sclerosing orbital psuedotumor.

In a further aspect, the invention features a method of treating an eye injury, comprising locally administering an effective amount of a ligand binding molecule described herein to a subject in need thereof, such that the eye injury is ameliorated or improved. Preferably, the eye injury is a corneal injury or conjunctival injury and the method of treatment reduces angiogenesis and inflammation associated with the eye injury. In some embodiments, the method is useful to treat acute and sub-acute corneal injury or conjunctival injury. Acute corneal injury may be treated within 24 hours of occurrence, and includes corneal injury or conjunctival injury caused by a penetrating object, a foreign body, or a chemical or burn injury. A sub-acute injury may be treated up to two weeks post-injury and may include the above listed injuries as well as infectious etiologies. In some embodiments, the eye injury is caused by trauma, e.g., surgical injuries, chemical burn, corneal transplant, infectious or inflammatory diseases.

Length of treatment will vary according to the injury, but treatment duration may be short, e.g., up to one month, and may include a 3-6 month observation period, during which retreatment may be provided. Administration may also include a second agent, such as an immunosuppressive agent, for example, one or more of a corticosteroid, dexamethasone, or cyclosporin A. Local administration includes, for example, administration of the ligand binding molecule in eye drops applied to the eye, or subconjunctival injection to the eye.

In a further aspect, described herein is a method of healing an eye injury, comprising locally administering an effective amount of a ligand binding molecule described herein to a subject in need thereof, such that the eye injury heals.

In a further aspect, described herein is a method of reducing or ameliorating angiogenesis associated with an eye injury, comprising locally administering an effective amount of a ligand binding molecule described herein to a subject in need thereof, such that the angiogenesis associated with the eye injury is reduced or ameliorated.

In a further aspect, described herein is a method of reducing or ameliorating inflammation associated with an eye injury, comprising locally administering an effective amount of a ligand binding molecule described herein to a subject in need thereof, such that the inflammation associated with the eye injury is reduced or ameliorated.

In a further aspect, described herein is a method of administering a ligand binding molecule of the present invention for treatment of angiogenesis and/or inflammation associated with eye injury or infection, comprising local administration by eye drops comprising a ligand binding molecule described herein, or subconjunctival administration by injection or implantation.

In a further aspect, the described herein is a method of extending corneal graft survival following corneal transplantation in a patient by administering to the patient an effective amount of a pharmaceutical composition containing a ligand binding molecule described herein (whereby angiogenesis and/or lymphangiogenesis is suppressed in the cornea of the patient).

Dose response studies permit accurate determination of a proper quantity of ligand binding molecule to employ. Effective quantities can be estimated, for example, from measurements of the binding affinity of a polypeptide for a target receptor, of the quantity of receptor present on target cells, of the expected dilution volume (e.g., patient weight and blood volume for in vivo embodiments), and of polypeptide clearance rates. For example, existing literature regarding dosing of known VEGF-C antibodies known also provides guidance for dosing of the ligand binding molecules described herein. Literature describing dosing of Aflibercept (Regeneron), a ligand trap based on VEGFR-1/VEGFR-2, also may be used to provide guidance for dosing of therapeutic molecules described herein.

In some embodiments, when being administered by intravitreal injection, the ligand binding molecule is administered in a concentration of about 2 mg to about 4 mg per eye (or about 1 mg to about 3 mg, or about 1 mg to about 4 mg, or about 3 mg to about 4 mg, or about 1 mg to about 2 mg per eye). In some embodiments, the ligand binding molecule is administered in a concentration of about 1 mg, or about 2 mg, or about 3 mg, or about 4 mg, or about 5 mg, or about 6 mg per eye. The ligand binding molecule, in some embodiments, is present in any of the concentrations listed above in a volume of 10 µl, 15 µl, 20 µl, 25 µl, 30 µl, 35 µl, 40 µl, 45 µl, 50 µl, 60 µl, 70 µl, 80 µl, 90 µl, 95 µl or 100 µl. In some embodiments, the ligand binding molecule is administered at a concentration of about 2-4 mg/50 µl.

The ligand binding molecule described herein can be administered purely as a prophylactic treatment to prevent neovascularization in subjects at risk for developing an ocular disease associated with neovascularization (e.g., diabetic retinopathy, macular degeneration), or as a therapeutic treatment to subjects afflicted the ocular disease, for the purpose of inhibiting neovascularization in the eye of a subject in need thereof.

Subjects who are at risk of developing diabetic retinopathy or macular degeneration include subjects over the age of fifty; subjects afflicted with rheumatoid arthritis, subjects with diabetes, subjects with thyroid abnormalities, subjects with asthma, subjects with cataracts, subjects with glaucoma, subjects with lupus, subjects with high blood pressure and subjects with retinal detachment. Other risk factors include genetics, diet, smoking and sublight exposure.

In some embodiments, described herein is a method of selecting a therapeutic regimen for a subject in need thereof comprising screening a subject for one or more symptoms of an ocular disorder associated with retinal neovascularization and prescribing for the subject administration of a composition comprising a ligand binding molecule described herein. In another embodiment, described herein is a method of treating a subject affected with an ocular disorder associated with retinal neovascularization comprising identifying a subject as having one or more symptoms of the ocular disorder and administering a composition comprising a ligand binding molecule to the subject. Symptoms associated with an ocular disorder associated with retinal neovascularization include, but are not limited to, blurred vision and slow vision loss over time, tiny particles drifting inside the eye, shadows or missing areas of vision, distorted vision and night blindness.

In some embodiments, the methods described herein further comprise prescribing (or administering) a standard of care regimen for the treatment of dry eye disease. In the context of methods described herein, "standard of care" refers to a treatment that is generally accepted by clinicians for a certain type of patient diagnosed with a type of illness. For diabetic retinopathy and macular degeneration, for example, an aspect of the invention is to improve standard of care therapy with co-therapy with a ligand binding molecule described herein that inhibit retinal neovascularization. Exemplary standard of care therapeutic for diabetic retinopathy and macular degeneration include, but are not limited to, eyelid hygiene, topical antibiotics (including, but not limited to erythromycin or bacitracin ointments), oral tetracyclines (tetracycline, doxycycline, or minocycline), anti-inflammatory compounds (including, but not limited to, cyclosporine), corticosteroids, laser photocoagulation and photodynamic therapy.

Also contemplated are methods of treating a mammalian subject with an ocular disorder associated with retinal neovascularization that is hypo-responsive to a standard of care regimen for the treatment of the ocular disorder comprising administering a ligand binding molecule to the subject in an amount effective to treat the disorder.

The mammalian subject is preferably a human subject. Practice of methods of the invention in other mammalian subjects, especially mammals that are conventionally used as models for demonstrating therapeutic efficacy in humans (e.g., primate, porcine, canine, or rabbit animals), is also contemplated.

Combination Therapies and Additional Active Agents

Combination therapy and prophylactic embodiments of the invention include products and methods. Exemplary compounds that may be administered in combination with one or more of the ligand binding molecules described herein include, but are not limited to, the compounds provided below in Table 2.

| Product | Target or Mechanism of Action | Comments |
|---|---|---|
| VEGF-A Inhibitors | | |
| KH902 | VEGF-A inhibitor | VEGF-Receptor-Fc Recombinant fusion protein with ligand binding domain taken from VEGFR-1 and VEGFR-2 that binds all VEGF-A isoforms and PlGF but not VEGF-C or -D |
| VEGF-A DARPin (AGN-150998) | VEGF-A inhibitor | Derived from ankyrin protein with selective binding to VEGF-A and not other members of the VEGF family. |
| ESBA1008 | Single chain antibody fragment to VEGF-A | |
| Ranibizumab (Lucentis ™) | Monoclonal antibody fragment (Fab) | Derived from the same parent mouse antibody as bevacizumab (Avastin ™) |
| Anti-Pericyte (PDGF-B Inhibitors) | | |
| E10030 (Fovista ™) | Anti-PDGF aptamer | Targets pericyte mediated resistance to anti-VEGF-A therapy. |
| Multi-Targeted Kinase Inhibitors | | |
| Vatalanib (PTK787/PTK/ZK | Tyrosine kinase inhibitor | |
| AL-39324 | Tyrosine kinase inhibitor | Injectable. |
| Pazopanib | Tyrosine kinase inhibitor | TKI of VEGFR-1, VEGFR-2, VEGFR-3, PDGFR-a/b and cKit. Topical eye drop application. |
| TG100801 | Tyrosine kinase inhibitor | Prodrug inhibits VEGF, PDGF, FGF receptors and Src family of kinases. Topical administration. |
| Squalamine | Small molecule aminosterol binds calmodulin | Binds calmodulin and prevents modulation of VEGF, PDGF and bFGF. |
| mTOR Pathway Inhibitors | | |
| Sirolimus (DE-109) | mTOR inhibitor | Broad acting anti-proliferative and immune suppressive agent. |
| Sirolimus | mTOR inhibitor | |
| PF-655 (REDD14P) | Synthetic siRNA to RTP801 (mTOR regulator) | Stress induced mTOR inhibitor that stabilises TSC1-TSC2 inhibitory complex and enhances oxidative stress-dependent cell death. |
| Palomid529 | Small molecule TORC1/TORC2 inhibitor (mTOR pathway) | |
| Vascular Disrupting Agents | | |
| Zybrestat | VDA (vascular disrupting agent) and cadherin 5 inhibitor | |
| Fosbretabulin (combretastatin A4 phosphate) | Vascular disrupting agent (VDA) | |

-continued

| Product | Target or Mechanism of Action | Comments |
|---|---|---|
| Anti-Inflammatory Agents Corticosteroids | | |
| Posurdex/SK-0503 | Corticosteroid and VEGF-A inhibitor | |
| Iluvien (fluocinolone acetonide) | Corticosteroid (intravitreal insert) | |
| IBI-20089 | Slow release triamcinolone | |
| Complement Inhibitors | | |
| LFG316 | Anti-C5 (complement pathway) | Selectively targets inflammation associated with AMD |
| ARC1905 | Anti-C5 aptamer | |
| AL-78898A (POT-4) | Anti-C3 cyclic peptide | Targets C3 in the complement pathway. |
| 'Other' Anti-Inflammatory Agents | | |
| Humira (adalimumab) | Anti-TNF mAb | |
| Miscellaneous Targeted Agents | | |
| iSONEP | Anti-S1P mAb | mAb targets the lipid sphingosine-1-phosphate |
| Ocriplasmin | Truncated form of Human serine protease plasmin | Approved for the treatment of symptomatic vitreomacular adhesion |
| Volociximab | Chimeric Ab to a5b1 integrin | Blocks binding of a5b1 integrin to fibronectin involved in vascular stabilisation |
| hI-con1 | Anti-Tissue Factor | Chimeric, IgG-like homodimeric protein composed of a mutant factor V11a domain fused to an effector region (IgG Fc). Mutant fV11 binds to tissue factor which is expressed on the luminal surface of pathologic cells including AMD lesions, triggering immune destruction of h1-con1 targeted cells via effector functions |
| ORA102 | Target unknown. | |
| Gene Therapy | | |
| rAAV.sFlt-1 | Adenovrial gene delivery of soluble form of VEGFR-1. | Sub-retinally delivered gene therapy. 'Traps' VEGFR-1 ligands only (VEGF-A, VEGF-B, PIGF). |
| adPEDF | Adenoviral gene delivery of Pigment epithelium derived factor (PEDF) | PEDF is anti-angiogenic (inhibits VEGF induced proliferation, EC migration and permeability). |
| RetinoStat | Lentiviral delivery of angiostatin & endostatin | Angiostatin (fragment of plasmin) and endostatin (C-term fragement of Type XVIII collagen) are endogenous inhibitors of angiogenesis. |
| AAV2-sFLT01 | Adenoviral gene delivery of soluble form of VEGFR-1 | Intravitreally delivered gene therapy. 'Traps' VEGFR-1 ligands only (VEGF-A, VEGF-B, PIGF) |
| Antisense & siRNA | | |
| GS-101 | Antisense targeting IRS-1 | Topical application of antisense to Insulin-Receptor-Substrate-1 |
| Bevasiranib | siRNA targeting VEGF | |
| AGN211745 | siRNA targeting VEGFR-1 | |

The ligand binding molecules may be administered in combination with one or more additional active compounds or therapies, including a second receptor trap molecule, a cytotoxic agent, surgery, catheter devices and radiation. Exemplary combination products include two or more agents formulated as a single composition or packaged together in separate compositions, e.g., as a unit dose package or kit. Exemplary combination methods include prescribing for administration, or administration of two or more agents simultaneously or concurrently or at staggered times (i.e., sequentially).

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (Cytoxan®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estrainustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol®, Bristol-Myers Squibb Oncology, Princeton, N.J.) and docetaxel (Taxotere®; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

A "growth inhibitory agent" when used herein refers to a compound or composition which inhibits growth of a cell, especially a cancer cell either in vitro or in vivo. Examples of growth inhibitory agents include agents that block cell cycle progression (at a place other than S phase), such as agents that induce G 1 arrest and M-phase arrest. Classical M-phase blockers include the vincas (vincristine and vinblastine), Taxol®, and topo II inhibitors such as doxorubicin, epirubicin, daunorubicin, etoposide, and bleomycin. Those agents that arrest G 1 also spill over into S-phase arrest, for example, DNA alkylating agents such as tamoxifen, prednisone, dacarbazine, mechlorethamine, cisplatin, methotrexate, 5-fluorouracil, and ara-C.

VEGF-A (VEGF) Inhibitor Products

In some embodiments, methods described herein optionally comprise administering a therapeutic active to inhibit VEGF-A binding to one or more of its receptors, especially VEGFR-2. A VEGF-A inhibitor product may be administered in combination with one or more of the ligand binding molecules described herein. In some embodiments, the VEGF-A inhibitor product and the ligand binding molecule are co-administered in a single composition. In other embodiments, the VEGF-A inhibitor product is administered as a separate composition from the ligand binding molecule.

In one embodiment, the VEGF-A inhibitor product is selected from ranibizumab, bevacizumab, aflibercept, KH902 VEGF receptor-Fc fusion protein, 2C3 antibody, ORA102, pegaptanib, bevasiranib, SIRNA-027, decursin, decursinol, picropodophyllin, guggulsterone, PLG101, eicosanoid LXA4, PTK787, pazopanib, axitinib, CDDO-Me, CDDO-Imm, shikonin, beta-hydroxyisovalerylshikonin, EYE001, ganglioside GM3, DC101 antibody, Mab25 antibody, Mab73 antibody, 4A5 antibody, 4E10 antibody, 5F12 antibody, VA01 antibody, BL2 antibody, VEGF-related protein, sFLT01, sFLT02, Peptide B3, TG100801, sorafenib, or G6-31 antibody, or a pharmaceutically acceptable salt thereof of any of the aforementioned.

cDNA and amino acid sequences of human VEGFR-2 ECD are set forth in SEQ ID NOs: 5 and 6, respectively. The "VEGF-A inhibitor product" can be any molecule that acts with specificity to reduce VEGF-A/VEGFR-2 interactions, e.g., by blocking VEGF-A binding to VEGFR-2 or by reducing expression of VEGFR-2. The term "VEGF-A" as used herein refers to the vascular endothelial growth factor that induces angiogenesis or an angiogenic process and includes the various subtypes of VEGF that arise by, e.g., alternative splicing of the VEGF-A gene including $VEGF_{121}$, $VEGF_{165}$ and $VEGF_{189}$ induce angiogenesis or an angiogenic process. The term "VEGF" can be used to refer to a "VEGF" polypeptide or a "VEGF" encoding gene or nucleic acid.

The term "VEGF-A inhibitor product" refers to an agent that reduces, or inhibits, either partially or fully, the activity or production of VEGF-A. A VEGF-A inhibitor product can directly or indirectly reduce or inhibit the activity or production of a specific VEGF-A such as $VEGF_{165}$. Furthermore, "VEGF-A inhibitor products" include agents that act on either a VEGF-A ligand or its cognate receptor so as to reduce or inhibit a VEGF-A associated receptor signal. Examples of "VEGF-A inhibitor products" include antisense molecules, ribozymes or RNAi that target a VEGF-A nucleic acid; VEGF-A aptamers; VEGF-A antibodies; soluble VEGF receptor decoys that prevent binding of a VEGF-A to its cognate receptor; antisense molecules, ribozymes, or RNAi that target a cognate VEGF-A receptor (VEGFR-1 and/or VEGFR-2) nucleic acid; VEGFR-1 and VEGFR-2 aptamers or VEGFR-1 and VEGFR-2 antibodies; and VEGFR-1 and/or VEGFR-2 tyrosine kinase inhibitors.

The VEGF-A inhibitor can be a polypeptide comprising a soluble VEGFR-2 ECD fragment (amino acids 20-764 of SEQ ID NO: 6) that binds VEGF; a soluble VEGFR-1 ECD fragment, a soluble VEGFR-1/R2 based ligand trap, such as Aflibercept (Regeneron); VEGFR-2 anti-sense polynucleotides or short-interfering RNA (siRNA); anti-VEGFR-2 antibodies; a VEGFR-2 inhibitor polypeptide comprising an antigen-binding fragment of an anti-VEGFR-2 antibody that inhibits binding between VEGFR-2 and VEGF; an aptamer that inhibits binding between VEGFR-2 and VEGF-A. In some variations, the VEGFR-2 based ligand trap comprises a fusion protein comprising the soluble VEGFR-2 polypeptide fragment fused to an immunoglobulin constant region fragment (Fc). In some embodiments, a VEGFR-2 polypeptide fragment is fused to alkaline phosphatase (AP). Methods for making Fc or AP fusion constructs are found in WO 02/060950, the disclosure of which is incorporated herein by reference in its entirety.

A number of VEGF-A antibodies have been described, see for example, U.S. Pat. Nos. 8,349,322; 8,236,312; 8,216,571; 8,101,177; 8,092,797; 8,088,375; 8,034,905; 5,730,977; 6,342,219, 6,524,583, 6,451,764, 6,448,077, 6,416,758, 6,342,221 and PCT publications WO 96/30046, WO 97/44453, and WO 98/45331, the contents of which are incorporated by reference in their entirety. Exemplary VEGF-A antibodies include Bevacizumab (Avastin®) and Ranibizumab (Lucentis®). In some embodiments, one or more ligand binding molecules described herein are administered in combination with bevacizumab. In some embodiments, one or more ligand binding molecule described herein are administered in combination with ranibizumab.

In some embodiments, the VEGF-A inhibitor is EYE001 (previously referred to as NX1838), which is a modified, PEGylated aptamer that binds with high and specific affinity to the major soluble human VEGF isoform (see, U.S. Pat. Nos. 6,011,020; 6,051,698; and 6,147,204). The aptamer binds and inactivates VEGF in a manner similar to that of a high-affinity antibody directed towards VEGF. Another useful VEGF aptamer is EYE001 in its non-pegylated form.

In a preferred embodiment, one or more ligand binding molecules described herein are administered in combination with aflibercept (Eylea®) (Holash et al., Proc. Natl. Acad. Sci. USA, 99:11393-11398, 2002, the disclosure of which is incorporated herein by reference in its entirety.

A number of VEGFR-2 antibodies have been described, see for example, U.S. Pat. No. 6,334,339 and U.S. Patent Publication Nos. 2002/0064528, 2005/0214860, and 2005/0234225 (all of which are incorporated herein by reference in their entireties). Antibodies are useful for modulating VEGFR-2/VEGF interactions due to the ability to easily generate antibodies with relative specificity, and due to the continued improvements in technologies for adopting antibodies to human therapy. Thus, the invention contemplates use of antibodies (e.g., monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR sequences which specifically recognize a polypeptide of the invention) specific for VEGFR-2. Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86 95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779 783 (1992); Lonberg et al., Nature 368 856 859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13:65-93 (1995).

PDGF Inhibitor Products

In some embodiments, methods described herein optionally comprise administering a therapeutic active to inhibit PDGF binding to one or more of its receptors. A PDGF Inhibitor Product inhibitor product may be administered in combination with one or more of the ligand binding molecules described herein. In some embodiments, the PDGF inhibitor product and the ligand binding molecule are co-administered in a single composition. In other embodiments, the PDGF inhibitor product is administered as a separate composition from the ligand binding molecule.

The term "PDGF" refers to a platelet-derived growth factor that regulates cell growth or division. As used herein, the term "PDGF" includes the various subtypes of PDGF including PDGF-B, PDGF-A, PDGF-C, PDGF-D, variant forms thereof and dimerized forms thereof, including PDGF-AA, PDGF-AB, PDGF-BB, PDGF-CC, and PDGF-DD. Platelet derived growth factors includes homo- or heterodimers of A-chain (PDGF-A) and B-chain (PDGF-B) that exert their action via binding to and dimerization of two related receptor tyrosine kinase platelet-derived growth factor cell surface receptors (i.e., PDGFRs), PDGFR-α and PDGFR-β. In addition, PDGF-C and PDGF-D, two additional protease-activated ligands for the PDGFR complexes, have been identified (Li et al., (2000) *Nat. Cell. Biol.* 2: 302-9; Bergsten et al., (2001) *Nat. Cell. Biol.* 3: 512-6; and Uutele et al., (2001) *Circulation* 103: 2242-47). Due to the different ligand binding specificities of the PDGFRs, it is known that PDGFR-α/α binds PDGF-AA, PDGF-BB, PDGF-AB, and PDGF-CC; PDGFR-β/β binds PDGF-BB and PDGF-DD; whereas PDGFR-α/β binds PDGF-AB, PDGF-BB, PDGF-CC, and PDGF-DD (Betsholtz et al., (2001) *BioEssays* 23: 494-507). As used herein, the term "PDGF" also refers to those members of the class of growth factors that induce DNA synthesis and mitogenesis through the binding and activation of a PDGFR on a responsive cell type. PDGFs can effect, for example: directed cell migration (chemotaxis) and cell activation; phospholipase activation; increased phosphatidylinositol turnover and prostaglandin metabolism; stimulation of both collagen and collagenase synthesis by responsive cells; alteration of cellular metabolic activities, including matrix synthesis, cytokine production, and lipoprotein uptake; induction, indirectly, of a proliferative response in cells lacking PDGF receptors; and potent vasoconstrictor activity. The term "PDGF" can be used to refer to a "PDGF" polypeptide, a "PDGF" encoding gene or nucleic acid, or a dimerized form thereof.

The term "PDGF inhibitor product" refers to an agent that reduces, or inhibits, either partially or fully, the activity or production of a PDGF. A PDGF inhibitor product can directly or indirectly reduce or inhibit the activity or production of a specific PDGF such as PDGF-B. Furthermore, "PDGF inhibitor products" include agents that act on a PDGF ligand or its cognate receptor so as to reduce or inhibit a PDGF-associated receptor signal. Examples of "PDGF inhibitor products" include antisense molecules, ribozymes or RNAi that target a PDGF nucleic acid; PDGF aptamers, PDGF antibodies to PDGF itself or its receptor, or soluble PDGF receptor decoys that prevent binding of a PDGF to its cognate receptor; antisense molecules, ribozymes or RNAi that target a cognate PDGF receptor (PDGFR) nucleic acid; PDGFR aptamers or PDGFR antibodies that bind to a cognate PDGFR receptor; and PDGFR tyrosine kinase inhibitors.

In one embodiment, the PDGF inhibitor product is selected from: a compound of Formula A, B, C, D or E as described and defined is US 2012/0100136 (the entire contents of which are herein incorporated by reference), p1B3 antibody, CDP860, IMC-3G3, 162.62 antibody, 163.31 antibody, 169.14 antibody, 169.31 antibody, αR1 antibody, 2A1E2 antibody, M4TS.11 antibody, M4TS.22 antibody, Hyb 120.1.2.1.2 antibody, Hyb 121.6.1.1.1 antibody, Hyb 127.5.7.3.1 antibody, Hyb 127.8.2.2.2 antibody, Hyb 1.6.1 antibody, Hyb 1.11.1 antibody, Hyb 1.17.1 antibody, Hyb 1.18.1 antibody, Hyb 1.19.1 antibody, Hyb 1.23.1 antibody, Hyb 1.24 antibody, Hyb 1.25 antibody, Hyb 1.29 antibody, Hyb 1.33 antibody, Hyb 1.38 antibody, Hyb 1.39 antibody, Hyb 1.40 antibody, Hyb 1.45 antibody, Hyb 1.46 antibody, Hyb 1.48 antibody, Hyb 1.49 antibody, Hyb 1.51 antibody, Hyb 6.4.1 antibody, F3 antibody, Humanized F3 antibody, C1 antibody, Humanized C1 antibody, 6.4 antibody, anti-mPDGF-C goat IgG antibody, C3.1 antibody, PDGFR-B1 monoclonal antibody, PDGFR-B2 monoclonal antibody, 6D11 monoclonal antibody, Sis 1 monoclonal antibody, PR7212 monoclonal antibody, PR292 monoclonal antibody, HYB 9610 monoclonal antibody, HYB 9611 monoclonal antibody, HYB 9612 monoclonal antibody, or HYB 9613 monoclonal antibody, or a pharmaceutically acceptable salt thereof of any of any of the aforementioned.

In a preferred embodiment, one or more ligand binding molecules described herein are administered in combination with a PDGFR-beta antibody (such as that being developed by Regeneron Inc. for ocular indications) or an anti-PDGF aptamer (such as E10030 being developed by Ophthotech Inc. for ocular indications).

Antibody fragments, for example of a VEGF-A and PGDF inhibitor product, including Fab, Fab', F(ab')2, Fv, scFv, are also contemplated. The term "specific for," when used to describe antibodies of the invention, indicates that the variable regions of the antibodies of the invention recognize and bind the polypeptide of interest exclusively (i.e., able to distinguish the polypeptides of interest from other known polypeptides of the same family, by virtue of measurable differences in binding affinity, despite the possible existence of localized sequence identity, homology, or similarity between family members). It will be understood that specific antibodies may also interact with other proteins (for example, S. aureus protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies of the invention can be produced using any method well known and routinely practiced in the art.

In another embodiment, methods described herein optionally comprise administering an anti-sense (e.g. antisense to VEGFR-2) nucleic acid molecule to the subject. Antisense nucleic acid molecules to a particular protein (e.g. VEGFR-2) are useful therapeutically to inhibit the translation of mRNAs encoding that protein (e.g. VEGFR-2) where the therapeutic objective involves a desire to eliminate the presence of the protein or to downregulate its levels. VEGFR-2 anti-sense RNA, for example, could be useful as a VEGFR-2 antagonizing agent in the treatment of diseases in which VEGFR-2 is involved as a causative agent, e.g. inflammatory diseases.

An antisense nucleic acid comprises a nucleotide sequence that is complementary to a "sense" nucleic acid encoding a protein (e.g., complementary to the coding strand of a double-stranded cDNA molecule or complementary to an mRNA sequence). (See, e.g., the VEGFR-3 cDNA sequence of SEQ ID NO: 1). Methods for designing and optimizing antisense nucleotides are described in Lima et al., (J Biol Chem; 272:626-38. 1997) and Kurreck et al., (Nucleic Acids Res.; 30:1911-8. 2002). In specific aspects, antisense nucleic acid molecules are provided that comprise a sequence complementary to at least about 10, 25, 50, 100, 250 or 500 nucleotides or an entire protein (e.g. VEGFR-2) coding strand, or to only a portion thereof. Nucleic acid molecules encoding fragments, homologs, derivatives and analogs of a protein (e.g. VEGFR-2) or antisense nucleic acids complementary to a protein (VEGFR-2) nucleic acid sequence are also contemplated.

In one embodiment, an antisense nucleic acid molecule is antisense to a "coding region" of the coding strand of a nucleotide sequence encoding a protein such as, e.g. VEGFR-2. The term "coding region" refers to the region of the nucleotide sequence comprising codons which are translated into amino acid residues. In another embodiment, the antisense nucleic acid molecule is antisense to a "conceding region" of the coding strand of a nucleotide sequence encoding the protein such as, e.g. VEGFR-2. The term "conceding region" refers to 5' and 3' sequences which flank the coding region that are not translated into amino acids (i.e., also referred to as 5' and 3' untranslated regions).

Antisense nucleic acids of the invention can be designed according to the rules of Watson and Crick or Hoogsteen base pairing. The antisense nucleic acid molecule can be complementary to the entire coding region of protein mRNA, but more preferably is an oligonucleotide that is antisense to only a portion of the coding or noncoding region of protein mRNA. An antisense oligonucleotide can be, for example, about 5, 10, 15, 20, 25, 30, 35, 40, 45, or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation.

The antisense nucleic acid molecules are typically administered to a subject or generated in situ such that they hybridize with or bind to cellular mRNA and/or genomic DNA encoding a protein (e.g. VEGFR-2) to thereby inhibit expression of the protein (e.g., by inhibiting transcription and/or translation). The hybridization can be by conventional nucleotide complementarity to form a stable duplex, or, for example, in the case of an antisense nucleic acid molecule that binds to DNA duplexes, through specific interactions in the major groove of the double helix.

In still another embodiment, protein RNA can be used for induction of RNA interference (RNAi), using double stranded (dsRNA) (Fire et al., Nature 391: 806-811. 1998) or short-interfering RNA (siRNA) sequences (Yu et al., Proc Natl Acad Sci USA. 99:6047-52, 2002). "RNAi" is the process by which dsRNA induces homology-dependent degradation of complimentary mRNA. In one embodiment, a nucleic acid molecule of the invention is hybridized by complementary base pairing with a "sense" ribonucleic acid of the invention to form the double stranded RNA. The dsRNA antisense and sense nucleic acid molecules are provided that correspond to at least about 20, 25, 50, 100, 250 or 500 nucleotides or an entire protein (e.g. VEGFR-2) coding strand, or to only a portion thereof. In an alternative embodiment, the siRNAs are 30 nucleotides or less in length, and more preferably 21- to 23-nucleotides, with characteristic 2- to 3-nucleotide 3'-overhanging ends, which are generated by ribonuclease III cleavage from longer dsRNAs. See e.g. Tuschl T. (Nat Biotechnol. 20:446-48. 2002). Preparation and use of RNAi compounds is described in U.S. Patent Publication No. 2004/0023390, the disclosure of which is incorporated herein by reference in its entirety.

Intracellular transcription of small RNA molecules can be achieved by cloning the siRNA templates into RNA polymerase III (Pol III) transcription units, which normally encode the small nuclear RNA (snRNA) U6 or the human RNAse P RNA H1. Two approaches can be used to express siRNAs: in one embodiment, sense and antisense strands constituting the siRNA duplex are transcribed by individual promoters (Lee, et al. Nat. Biotechnol. 20, 500-505. 2002); in an alternative embodiment, siRNAs are expressed as stem-loop hairpin RNA structures that give rise to siRNAs after intracellular processing (Brummelkamp et al. Science 296:550-553. 2002) (incorporated herein by reference).

The dsRNA/siRNA is most commonly administered by annealing sense and antisense RNA strands in vitro before delivery to the organism. In an alternate embodiment, RNAi may be carried out by administering sense and antisense nucleic acids of the invention in the same solution without annealing prior to administration, and may even be performed by administering the nucleic acids in separate vehicles within a very close timeframe. Nucleic acid molecules encoding fragments, homologs, derivatives and analogs of a protein (such as, e.g. VEGFR-2) or antisense nucleic acids complementary to a mVEGFR-2 nucleic acid sequence are also contemplated.

Aptamers are another nucleic acid based method for interfering with the interaction of receptor and its cognate ligand, such as, e.g. a VEGFR-2 with VEGF-A and a PDGFR with PGDF. Aptamers are DNA or RNA molecules that have been selected from random pools based on their ability to bind other molecules. Aptamers have been selected which bind nucleic acid, proteins, small organic compounds, and even entire organisms. Methods and compositions for identifying and making aptamers are known to those of skill in the art and are described e.g., in U.S. Pat. No. 5,840,867 and U.S. Pat. No. 5,582,981 each incorporated herein by reference in their entireties.

Recent advances in the field of combinatorial sciences have identified short polymer sequences with high affinity and specificity to a given target. For example, SELEX technology has been used to identify DNA and RNA aptamers with binding properties that rival mammalian antibodies, the field of immunology has generated and isolated antibodies or antibody fragments which bind to a myriad of compounds and phage display has been utilized to discover new peptide sequences with very favorable binding properties. Based on the success of these molecular evolution techniques, it is certain that molecules can be created which bind to any target molecule. A loop structure is often involved with providing the desired binding attributes as in the case of: aptamers which often utilize hairpin loops created from short regions without complimentary base pairing, naturally derived antibodies that utilize combinatorial arrangement of looped hyper-variable regions and new phage display libraries utilizing cyclic peptides that have shown improved results when compared to linear peptide phage display results. Thus, sufficient evidence has been generated to suggest that high affinity ligands can be created and identified by combinatorial molecular evolution techniques. For the present invention, molecular evolution techniques can be used to isolate ligand binding molecules specific for ligands described herein. For more on aptamers, See generally, Gold, L., Singer, B., He, Y. Y., Brody. E., "Aptamers As Therapeutic And Diagnostic Agents," J. Biotechnol. 74:5-13 (2000). Relevant techniques for generating aptamers may be found in U.S. Pat. No. 6,699,843, which is incorporated by reference in its entirety.

In some embodiments, the aptamer may be generated by preparing a library of nucleic acids; contacting the library of nucleic acids with a growth factor, wherein nucleic acids having greater binding affinity for the growth factor (relative to other library nucleic acids) are selected and amplified to yield a mixture of nucleic acids enriched for nucleic acids with relatively higher affinity and specificity for binding to the growth factor. The processes may be repeated, and the selected nucleic acids mutated and re-screened, whereby a growth factor aptamer is be identified.

In yet another variation, the VEGF-A inhibitor product comprises a soluble ECD fragment of VEGFR-1 that binds VEGF and inhibits VEGF binding to VEGFR-2. cDNA and amino acid sequences of VEGFR-1 are set forth in SEQ ID NOs: 10 and 11. Exemplary ECD fragments of VEGFR-1 are described in U.S. Patent Publication No. 2006/0030000 and International Patent Publication No. WO 2005/087808, the disclosures of which are incorporated herein by reference in their entireties.

Anti-Inflammatory Agents

In another embodiment, the methods described herein optionally comprise administering one or more anti-inflammatory agents to the subject. In some embodiments, the anti-inflammatory agent and the ligand binding molecule are co-administered in a single composition. In other embodiments, the anti-inflammatory agent is administered as a separate composition from the ligand binding molecule. Combinations involving a ligand binding molecule, a VEGF-A inhibitor product, and an anti-inflammatory agent are specifically contemplated. As used herein, the term "anti-inflammatory agent" refers generally to any agent that reduces inflammation or swelling in a subject. A number of exemplary anti-inflammatory agents are recited herein, but it will be appreciated that there may be additional suitable anti-inflammatory agents not specifically recited herein, but which are encompassed by the present invention.

In one variation, the anti-inflammatory agent is a non-steroidal anti-inflammatory drug (NSAID). Exemplary NSAIDs include, but are not limited to: aspirin, Sulfasalazine™' Asacol™, Dipendtum™, Pentasa™, Anaprox™, Anaprox DS™ (naproxen sodium); Ansaid™ (flurbiprofen); Arthrotec™ (diclofenac sodium+misoprostil); Cataflam™/Voltaren™ (diclofenac potassium); Clinoril™ (sulindac); Daypro™ (oxaprozin); Disalcid™ (salsalate); Dolobid™ (diflunisal); EC Naprosyn™ (naproxen sodium); Feldene™ (piroxicam); Indocin™' Indocin SR™ (indomethacin); Lodine™, Lodine XL™ (etodolac); Motrin™ (ibuprofen); Naprelan™ (naproxen); Naprosyn™ (naproxen); Orudis™, (ketoprofen); Oruvail™ (ketoprofen); Relafen™ (nabumetone); Tolectin™, (tolmetin sodium); Trilisate™ (choline magnesium trisalicylate); Cox-1 inhibitors; Cox-2 Inhibitors such as Vioxx™ (rofecoxib); Arcoxia™ (etoricoxib); Celebrex™ (celecoxib); Mobic™ (meloxicam); Bextra™ (valdecoxib), Dynastat™ paracoxib sodium; Prexige™ (lumiracoxib), and nambumetone. Additional suitable NSAIDs, include, but are not limited to, the following: 5-aminosalicyclic acid (5-ASA, mesalamine, lesalazine), ϵ-acetamidocaproic acid, S-adenosylmethionine, 3-amino-4-hydroxybutyric acid, amixetrine, anitrazafen, antrafenine, bendazac, bendazac lysinate, benzydamine, beprozin, broperamole, bucolome, bufezolac, ciproquazone, cloximate, dazidamine, deboxamet, detomidine, difenpiramide, difenpyramide, difisalamine, ditazol, emorfazone, fanetizole mesylate, fenflumizole, floctafenine, flumizole, flunixin, fluproquazone, fopirtoline, fosfosal, guaimesal, guaiazolene, isonixirn, lefetamine HCl, leflunomide, lofemizole, lotifazole, lysin clonixinate, meseclazone, nabumetone, nictindole, nimesulide, orgotein, orpanoxin, oxaceprolm, oxapadol, paranyline, perisoxal, perisoxal citrate, pifoxime, piproxen, pirazolac, pirfenidone, proquazone, proxazole, thielavin B, tiflamizole, timegadine, tolectin, tolpadol, tryptamid and those designated by company code number such as 480156S, AA861, AD1590, AFP802, AFP860, AI77B, AP504, AU8001, BPPC, BW540C, CHINOIN 127, CN100, EB382, EL508, F1044, FK-506, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301 and WY41770.

In another variation, the anti-inflammatory agent comprises be a compound that inhibits the interaction of inflammatory cytokines with their receptors. Examples of cytokine inhibitors useful in combination with the specific binding agents of the invention include, for example, antagonists (such as antibodies) of TGF-α (e.g., Remicade), as well as antagonists (such as antibodies) directed against interleukins involved in inflammation. Such interleukins are described herein and preferably include, but are not limited to, IL-1, IL-2, IL-3, IL-4, IL-5, IL-6, IL-8, IL-9, IL-12, IL-13, IL-17, and IL-18. See Feghali, et al., *Frontiers in Biosci.*, 2:12-26 (1997).

In another variation, the anti-inflammatory agent is a corticosteroid. Exemplary corticosteroids include, but are not limited to, difloroasone diacetate, clobetasol propionate, halobetasol propionate, betamethasone, betamethasone dipropionate, budesonide, cortisone, dexamethasone, fluocinonide, halcinonide desoximethasone, triamcinolone, fluticasone propionate, fluocinolone acetonide, flurandrenolide, mometasone furoate, betamethosone, fluticasone propionate, fluocinolone acetonide, aclometasome dipropionate, methylprednisolone, prednisolone, prednisone, triamcinolone, desonide and hydrocortisone.

In another variation, the anti-inflammatory agent is cyclosporine.

Antibiotics

In another embodiment, the methods described herein optionally further comprise administering an antibiotic to the subject. In some embodiments, the antibiotic and the ligand binding molecule are co-administered in a single composition. In other embodiments, the antibiotic is administered as a separate composition from the ligand binding molecule. Exemplary antibiotics include, but are not limited to, tetracycline, aminoglycosides, penicillins, cephalosporins, sulfonamide drugs, chloramphenicol sodium succinate, erythromycin, vancomycin, lincomycin, clindamycin, nystatin, amphotericin B, amantidine, idoxuridine, p-amino salicyclic acid, isoniazid, rifampin, antinomycin D, mithramycin, daunomycin, adriamycin, bleomycin, vinblastine, vincristine, procarbazine, and imidazole carboxamide.

Tyrosine Kinase Inhibitors

In another embodiment, the methods described herein optionally further comprise administering a tyrosine kinase inhibitor that inhibits VEGFR-2 and/or VEGFR-3 activity.

Exemplary tyrosine kinase inhibitors for use in the methods described herein include, but are not limited to, AEE788 (TKI, VEGFR-2, EGFR: Novartis); ZD6474 (TKI, VEGFR-1, -2,-3, EGFR: Zactima: AstraZeneca); AZD2171 (TKI, VEGFR-1, -2: AstraZeneca); SU 11248 (TKI, VEGFR-1, -2, PDGFR: Sunitinib: Pfizer); AG13925 (TKI, VEGFR-1, -2: Pfizer); AG013736 (TKI, VEGFR-1, -2: Pfizer); CEP-7055 (TKI, VEGFR-1, -2, -3: Cephalon); CP-547,632 (TKI, VEGFR-1, -2: Pfizer); GW7S6024 (TKL VEGFR-1, -2, -3: GlaxoSmithKline); GW786034 (TKI, VEGFR-1, -2, -3: GlaxoSmithKline); sorafenib (TKI, Bay 43-9006, VEGFR-1, -2, PDGFR: Bayer/Onyx); SU4312 (TKI, VEGFR-2, PDGFR: Pfizer); AMG706 (TKI, VEGFR-1, -2, -3: Amgen); XL647 (TKI, EGFR, HER2, VEGFR, ErbB4: Exelixis); XL999 (TKI, FGFR, VEGFR, PDGFR, FII-3: Exelixis); PKC412 (TKI, KIT, PDGFR, PKC, FLT3, VEGFR-2: Novartis); AEE788 (TKI, EGFR, VEGFR2, VEGFR-1: Novartis): OSI-030 (TKI, c-kil, VEGFR: OSI Pharmaceuticals); OS1-817 (TKI c-kit, VEGFR: OSI Pharmaceuticals); DMPQ (TKI, ERGF, PDGFR, ErbB2. p56. pkA, pkC); MLN518 (TKI, Flt3, PDGFR, c-KIT (T53518: Millennium Pharmaceuticals); lestaurinib (TKI, FLT3, CEP-701, Cephalon); ZD 1839 (TKI, EGFR: gefitinib, Iressa: AstraZcneca); OSI-774 (TKI, EGFR: Erlotininb: Tarceva: OSI Pharmaceuticals); lapatinib (TKI, ErbB-2, EGFR, and GD-2016: Tykerb: GlaxoSmithKline).

In some embodiments, the methods described herein further comprise administering a tyrosine kinase inhibitor that inhibits angiogenesis to the subject. Exemplary anti-angiogenic tyrosine kinase inhibits and their targets are provided below in Table 2.

TABLE 2

Antiangiogenic tyrosine kinase receptor inhibitors and their targets

| Agent | VEGFR-1 | VEGFR-2 | VEGFR-3 | PDGFR | EGFR | Other targets |
|---|---|---|---|---|---|---|
| Vandetanib |  | • |  |  | • | RET |
| Sunitinib | • | • | • | • |  | KIT, FLT3, RET |
| Axitinib | • | • | • |  |  |  |
| Sorafenib | • | • | • | • |  | KIT, RAF, FLT3 |
| Vatalanib | • | • | • | • |  | KIT |
| Cediranib | • | • | • | • |  | KIT |
| Motesanib | • | • | • | • |  | KIT, RET |
| Pazopanib | • | • | • | • |  | KIT |
| BIBF 1120 |  | • |  | • |  | FGFR |

Abbreviations: FGFR, fibroblast-like growth factor receptor; FLT3, FMS-like tyrosine kinase 3; KIT, stem cell factor receptor; RET, glial cell line-derived neurotrophic factor receptor: VEGFR, vascular endothelial growth factor receptor.

The ligand binding molecules may be administered in combination with more than one additional active compounds or therapies. In one embodiment, a ligand binding molecule of the present invention is administered in combination with a PDGF inhibitor product and a VEGF-A inhibitor product. For example, a ligand binding molecule (such as that comprising the amino acid sequence of SEQ ID NO: 3) may be administered in combination with (i) Aflibercept (Eylea®) and (ii) a PDGFR antibody (such as that being developed by Regeneron Inc. for ocular indications) or a PDGF apatamer (such as E10030 (Fovista™) being developed by Ophthotech Inc. for ocular indications).

Administration of the Combination Therapy

Combination therapy with one or more of the additional active agents described herein may be achieved by administering to a subject a single composition or pharmacological formulation that includes the ligand binding molecule and the one or more additional active agents, or by administering to the subject two (or more) distinct compositions or formulations, at the same time, wherein one composition includes a ligand binding molecule and the other includes an additional active agent.

Alternatively, the combination therapy employing a ligand binding molecule described herein may precede or follow the second agent treatment by intervals ranging from minutes to weeks. In embodiments where the second agent and the ligand binding molecule are administered separately, one would generally ensure that a significant period of time did not expire between the times of each delivery, such that the agent and the ligand binding molecule would still be able to exert an advantageously combined effect. In such instances, it is contemplated that one would administer both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. Repeated treatments with one or both agents is specifically contemplated.

Formulations and Pharmaceutically Acceptable Carriers

The present invention also provides pharmaceutical compositions comprising a ligand binding molecule of the invention. Such compositions comprise a therapeutically effective amount of one or more ligand binding molecules and a pharmaceutically acceptable carrier. In one embodiment, such compositions comprise one or more ligand binding molecules and optionally, one or more additional active agents (in the case of a combination therapy). In one embodiment, such compositions comprise one or more ligand binding molecules and optionally one or more additional active agents selected from a PDGF inhibitor product and a VEGF-A inhibitor product. In another embodiment, a composition comprising one or more ligand binding molecules of the invention and another composition comprising a PDGF inhibitor product or a VEGF-A inhibitor product are administered.

The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents.

The compositions may be in the form of solutions, suspensions, emulsion, tablets, pills, capsules, powders, granulates, gels including hydrogels, pastes, ointments, creams, delivery devices, sustained-release formulations, suppositories, injectables, implants, sprays, drops, aerosols and the like. Compositions comprising a ligand binding molecule, one or more additional active agents, or both, can be formulated according to conventional pharmaceutical practice (see, e.g., Remington: *The Science and Practice of Pharmacy*, (20th ed.) ed. A. R. Gennaro, 2000, Lippincott Williams & Wilkins, Philadelphia, Pa. and *Encyclopedia of Pharmaceutical Technology*, eds., J. Swarbrick and J. C. Boylan, 1988-2002, Marcel Dekker, New York). Examples of suitable pharmaceutical carriers are described in "Remington's Pharmaceutical Sciences" by E. W. Martin.

Administration of compositions may be by any suitable means that results in an amount of ligand binding molecule and/or additional active agents that is effective for the treatment or prevention of the particular disease or disorder. Each ligand binding molecule, for example, can be admixed with a suitable carrier substance, and is generally present in an amount of 1-95% by weight of the total weight of the composition. The composition may be provided in a dosage form that is suitable for ophthalmic, oral, parenteral (e.g., intravenous, intramuscular, subcutaneous), rectal, transdermal, nasal, or inhalant administration. In one embodiment, the composition is in a form that is suitable for injection directly in the eye The ligand binding molecules of the invention, and, where present in combination therapies, the one or more additional active agents, can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Ligand binding molecules and additional active agents of the present invention can possess a sufficiently basic functional group which can react with any of a number of inorganic and organic acids, to form a pharmaceutically acceptable salt. A pharmaceutically-acceptable acid addition salt is formed from a pharmaceutically-acceptable acid, as is well known in the art. Such salts include the pharmaceutically acceptable salts listed in Journal of Pharmaceutical Science, 66, 2-19 (1977) and The Handbook of Pharmaceutical Salts; Properties, Selection, and Use. P. H. Stahl and C. G. Wermuth (ED.s), Verlag, Zurich (Switzerland) 2002, which are hereby incorporated by reference in their entirety.

Pharmaceutically acceptable salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chloro benzoate, dinitrobenzoate, hydroxybenzoate, methoxybenzoate, methylbenzoate, o-acetoxybenzoate, naphthalene-2-benzoate, isobutyrate, phenylbutyrate, .alpha.-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of a ligand binding molecule and additional active agent having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-, bis-, or tris-(2-hydroxyethyl)amine, 2-hydroxytert-butylamine, or tris(hydroxymethyl)methylamine, N,N-di-lower alkyl-N(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like. The term "pharmaceutically acceptable salt" also includes a hydrate of a compound of the invention.

The compositions are, in one useful aspect, administered parenterally (e.g., by intramuscular, intraperitoneal, intravenous, intraocular, intravitreal, retro-bulbar, subconjunctival, subtenon or subcutaneous injection or implant) or systemically. Formulations for parenteral or systemic administration include sterile aqueous or non-aqueous solutions, suspensions, or emulsions. A variety of aqueous carriers can be used, e.g., water, buffered water, saline, and the like. Examples of other suitable vehicles include polypropylene glycol, polyethylene glycol, vegetable oils, gelatin, hydrogels, hydrogenated naphalenes, and injectable organic esters, such as ethyl oleate. Such formulations may also contain auxiliary substances, such as preserving, wetting, buffering, emulsifying, and/or dispersing agents. Biocompatible, biodegradable lactide polymer, lactide/glycolide copolymer, or polyoxyethylene-polyoxypropylene copolymers may be used to control the release of the active ingredients.

Alternatively, the compositions can be administered by oral ingestion. Compositions intended for oral use can be prepared in solid or liquid forms, according to any method known to the art for the manufacture of pharmaceutical compositions.

Solid dosage forms for oral administration include capsules, tablets, pills, powders, and granules. Generally, these pharmaceutical preparations contain active ingredients admixed with non-toxic pharmaceutically acceptable excipients. These include, for example, inert diluents, such as calcium carbonate, sodium carbonate, lactose, sucrose, glucose, mannitol, cellulose, starch, calcium phosphate, sodium phosphate, kaolin and the like. Binding agents, buffering agents, and/or lubricating agents (e.g., magnesium stearate) may also be used. Tablets and pills can additionally be prepared with enteric coatings. The compositions may optionally contain sweetening, flavoring, coloring, perfuming, and preserving agents in order to provide a more palatable preparation.

Solid dosage forms can be useful for treatment of ocular disorders. Compositions useful for ocular use include tablets comprising one or more ligand binding molecules in admixture with a pharmaceutically acceptable excipient. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Compositions of the present invention may be administered intraocularly by intravitreal injection into the eye as well as by subconjunctival and subtenon injections. Other routes of administration include transcleral, retrobulbar, intraperitoneal, intramuscular, and intravenous. Alternatively, compositions can be administered using a drug delivery device or an intraocular implant.

Liquid dosage forms for oral administration can include pharmaceutically acceptable emulsions, solutions, suspensions, syrups, and soft gelatin capsules. These forms can contain inert diluents commonly used in the art, such as water or an oil medium, and can also include adjuvants, such as wetting agents, emulsifying agents, and suspending agents.

In some instances, the compositions can also be administered topically, for example, by patch or by direct application to a region, such as the epidermis or the eye, susceptible to or affected by a neovascular disorder, or by iontophoresis.

In the case of combination therapies of the present invention, the ligand binding molecules and one or more additional active agents may be admixed in a tablet or other vehicle, or may be partitioned. In one example, the ligand binding molecule is contained on the inside of the tablet, and an additional active agent is on the outside, such that a substantial portion of the additional active agent is released prior to the release of the contained ligand binding molecule.

In one embodiment, compositions that comprise a ligand binding molecule (and optionally one or more additional active agents) can comprise one or more pharmaceutically acceptable excipients. In one embodiment, such excipients include, but are not limited to, buffering agents, non-ionic surfactants, preservatives, tonicity agents, amino acids, sugars and pH-adjusting agents. Suitable buffering agents include, but are not limited to, monobasic sodium phosphate, dibasic sodium phosphate, and sodium acetate. Suitable non-ionic surfactants include, but are not limited to, polyoxyethylene sorbitan fatty acid esters such as polysorbate 20 and polysorbate 80. Suitable preservatives include, but are not limited to, benzyl alcohol. Suitable tonicity agents include, but are not limited to sodium chloride, mannitol, and sorbitol. Suitable sugars include, but are not limited to, α,α-trehalose dehydrate. Suitable amino acids include, but are not limited to glycine and histidine. Suitable pH-adjusting agents include, but are not limited to, hydrochloric acid, acetic acid, and sodium hydroxide. In one embodiment, the pH-adjusting agent or agents are present in an amount effective to provide a pH of about 3 to about 8, about 4 to about 7, about 5 to about 6, about 6 to about 7, or about 7 to about 7.5. In one embodiment, a composition comprising a ligand binding molecule does not comprise a preservative. In another embodiment, a composition comprising a ligand binding molecule does not comprise an antimicrobial agent. In another embodiment, a composition comprising a ligand binding molecule does not comprise a bacteriostat.

In one embodiment, a composition comprising a ligand binding molecule (and optionally one or more additional active agents) is in the form of an aqueous solution that is suitable for injection. In one embodiment, a composition comprises a ligand binding molecule, a buffering agent, a pH-adjusting agent, and water for injection. In another embodiment, a composition comprises a ligand binding molecule, monobasic sodium phosphate, dibasic sodium phosphate, sodium chloride, hydrochloride acid, and sodium hydroxide. In another embodiment, a composition comprises a ligand binding molecule, phosphate (e.g. monobasic sodium phosphate), trehalose, sodium chloride and polysorbate.

Aqueous compositions useful for practicing the methods of the invention in an ocular setting have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers are included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

In some embodiments, the composition comprising a ligand binding molecule of the present invention is formulated for delivery to the eye of a subject. Suitable ophthalmic carriers are known to those skilled in the art and all such conventional carriers may be employed in the present invention. Exemplary compounds incorporated to facilitate and expedite transdermal delivery of topical compositions into ocular or adnexal tissues include, but are not limited to, alcohol (ethanol, propanol, and nonanol), fatty alcohol (lauryl alcohol), fatty acid (valeric acid, caproic acid and capric acid), fatty acid ester (isopropyl myristate and isopropyl n-hexanoate), alkyl ester (ethyl acetate and butyl acetate), polyol (propylene glycol, propanedione and hexanetriol), sulfoxide (dimethylsulfoxide and decylmethylsulfoxide), amide (urea, dimethylacetamide and pyrrolidone derivatives), surfactant (sodium lauryl sulfate, cetyltrimethylannmonium bromide, polaxamers, spans, tweens, bile salts and lecithin), terpene (d-limonene, alphaterpeneol, 1,8-cineole and menthone), and alkanone (N-heptane and N-nonane). Moreover, topically-administered compositions comprise surface adhesion molecule modulating agents including, but not limited to, a cadherin antagonist, a selectin antagonist, and an integrin antagonist. Thus, a particular carrier may take the form of a sterile, ophthalmic ointment, cream, gel, solution, or dispersion. Also including as suitable ophthalmic carriers are slow release polymers, e.g., "Ocusert" polymers, "Hydron" polymers, etc.

Exemplary ophthalmic viscosity enhancers that can be used in the present formulation include: carboxymethyl cellulose sodium; methylcellulose; hydroxypropyl cellulose; hydroxypropylmethyl cellulose; hydroxyethyl cellulose; polyethylene glycol 300; polyethylene glycol 400; polyvinyl alcohol; and providone.

Some natural products, such as veegum, alginates, xanthan gum, gelatin, acacia and tragacanth, may also be used to increase the viscosity of ophthalmic solutions.

A tonicity is important because hypotonic eye drops cause an edema of the cornea, and hypertonic eye drops cause deformation of the cornea. The ideal tonicity is approximately 300 mOsM. The tonicity can be achieved by methods described in Remington: The Science and Practice of Pharmacy, known to those versed in the art.

Stabilizers may also be used such as, for example, chelating agents, e.g., EDTA. Antioxidants may also be used, e.g., sodium bisulfite, sodium thiosulfite, 8-hydroxy quinoline or ascorbic acid. Sterility typically will be maintained by conventional ophthalmic preservatives, e.g., chlorbutanol, benzalkonium chloride, cetylpyridium chloride, phenyl mercuric salts, thimerosal, etc., for aqueous formulations, and used in amounts which are nontoxic and which generally vary from about 0.001 to about 0.1% by weight of the aqueous solution. Conventional preservatives for ointments include methyl and propyl parabens. Typical ointment bases include white petrolatum and mineral oil or liquid petrolatum. However, preserved aqueous carriers are preferred. Solutions may be manually delivered to the eye in suitable dosage form, e.g., eye drops, or delivered by suitable microdrop or spray apparatus typically affording a metered dose of medicament. Examples of suitable ophthalmic carriers include sterile, substantially isotonic, aqueous solutions containing minor amounts, i.e., less than about 5% by weight hydroxypropylmethylcellulose, polyvinyl alcohol, carboxymethylcellulose, hydroxyethylcelullose, glycerine and EDTA. The solutions are preferably maintained at substantially neutral pH and isotonic with appropriate amounts of conventional buffers, e.g., phosphate, borate, acetate, tris.

In some embodiments, penetration enhancers are added to the ophthalmologic carrier.

The amount of the ligand binding molecule that will be effective for its intended therapeutic use can be determined by standard clinical techniques based on the present description. In addition, in vitro assays may optionally be employed to help identify optimal dosage ranges. The amount of ligand binding molecule that is admixed with the carrier materials to produce a single dosage can vary depending upon the mammal being treated and the particular mode of administration.

The dosage of the ligand binding molecule can depend on several factors including the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect dosage used. Furthermore, the exact individual dosages can be adjusted somewhat depending on a variety of factors, including the specific combination therapies being administered, the time of administration, the route of administration, the nature of the formulation, the rate of excretion, the particular disease being treated (e.g. the particular ocular disorder being treated), the severity of the disorder, and the anatomical location of the neovascular disorder. Some variations in the dosage can be expected.

Generally, when orally administered to a mammal, the dosage of a ligand binding molecule of the present invention is normally 0.001 mg/kg/day to 100 mg/kg/day, 0.01 mg/kg/day to 50 mg/kg/day, or 0.1 mg/kg/day to 10 mg/kg/day. Generally, when orally administered to a human, the dosage of an antagonist of the present invention is normally 0.001 mg to 300 mg per day, 1 mg to 200 mg per day, or 5 mg to 50 mg per day. Dosages up to 200 mg per day may be necessary.

For administration of an antagonist of the present invention by parenteral injection, the dosage is normally 0.1 mg to 250 mg per day, 1 mg to 20 mg per day, or 3 mg to 5 mg per day. Injections may be given up to four times daily.

Generally, when orally or parenterally administered, the dosage of a ligand binding molecule for use in the present invention is normally 0.1 mg to 1500 mg per day, or 0.5 mg to 10 mg per day, or 0.5 mg to 5 mg per day. A dosage of up to 3000 mg per day can be administered.

When ophthalmologically administered to a human, for example intravitreally, the dosage of a ligand binding molecule per eye per administration is normally in a range from 0.003 mg, 0.03 mg, 0.03 mg, 0.1 mg or 0.5 mg to 5.0 mg, 4 mg, 3 mg, 2 mg or 1 mg, or 0.5 mg to 1.0 mg. Dosage of a ligand binding molecule is normally in the range 0.003 mg to 5.0 mg per eye per administration, or 0.03 mg to 4.0 mg per eye per administration, or 0.1 mg to 4.0 mg per eye per administration, or 0.03 mg to 3.0 mg per eye per administration, or 0.1 mg to 3.0 mg per eye per administration, or 0.1 mg to 1.0 mg per eye per administration, or 0.5 mg to 4.0 mg per eye per administration, or 0.5 mg to 3.0 mg per eye per administration, 0.5 mg to 2.0 mg per eye per administration, or 1.0 mg to 4.0 mg per eye per administration, or 1.0 mg to 3.0 mg per eye per administration, or 1.0 mg to 2.0 mg per eye per administration. In some embodiments, the ligand binding molecule is administered in a concentration of about 1 mg, or about 2 mg, or about 3 mg, or about 4 mg, or about 5 mg, or about 6 mg per administration per eye. The ligand binding molecule, in some embodiments, is present in any of the concentrations listed above in a volume of 10 µl, 15 µl, 20 µl, 25 µl, 30 µl, 35 µl, 40 µl, 45 µl, 50 µl, 60 µl, 70 µl, 80 µl, 90 µl, 95 µl or 100 µl. In some embodiments, the ligand binding molecule is administered at a concentration of about 2-4 mg/50 µl. The dosage volume can range from 0.01 mL to 0.2 mL administered per eye, or 0.03 mL to 0.15 mL administered per eye, or 0.05 mL to 0.10 mL administered per eye.

In some embodiments, when being administered by intravitreal injection, the ligand binding molecule is administered in a concentration of about 2 mg to about 4 mg per eye (or about 1 mg to about 3 mg, or about 1 mg to about 4 mg, or about 3 mg to about 4 mg, or about 1 mg to about 2 mg per eye). In some embodiments, the ligand binding molecule is administered in a concentration of about 1 mg, or about 2 mg, or about 3 mg, or about 4 mg, or about 5 mg, or about 6 mg per eye. The ligand binding molecule, in some embodiments, is present in any of the concentrations listed above in a volume of 10 µl, 15 µl, 20 µl, 25 µl, 30 µl, 35 µl, 40 µl, 45 µl, 50 µl, 60 µl, 70 µl, 80 µl, 90 µl, 95 µl or 100 µl. In some embodiments, the ligand binding molecule is administered at a concentration of about 2-4 mg/50 µl.

Generally, suitable dosage ranges for intravenous administration are generally about 50-5000 micrograms of active compound per kilogram body weight. Suitable dosage ranges for intranasal administration are generally about 0.01 pg/kg body weight to 1 mg/kg body weight. Effective doses may be extrapolated from dose response curves derived from in vitro or animal model test systems.

For systemic administration, a therapeutically effective dose can be estimated initially from in vitro assays. For example, a dose can be formulated in animal models to achieve a circulating concentration range that includes the 1050 as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable. The therapy may be provided alone or in combination with other drugs.

Administration of the ligand binding molecule and, when present in combination therapies, an additional agent, can, independently, be one to four times daily or one to four times per month or one to six times per year or once every two, three, four or five years. Administration can be for the duration of one day or one month, two months, three months, six months, one year, two years, three years, and may even be for the life of the patient. In one embodiment, the administration is performed once a month for three months. Chronic, long term administration will be indicated in many cases. The dosage may be administered as a single dose or divided into multiple doses. In general, the desired dosage should be administered at set intervals for a prolonged period, usually at least over several weeks or months, although longer periods of administration of several months or years or more may be needed.

In addition to treating pre-existing disorders, the compositions can be administered prophylactically in order to prevent or slow the onset of these disorders. In prophylactic applications, the composition can be administered to a patient susceptible to or otherwise at risk of a particular disorder, such as an ocular disorder.

Routes of Administration

The composition containing the ligand binding molecule described herein can be administered to a patient by a variety of means depending, in part, on the type of agent to be administered and the history, risk factors and symptoms of the patient. Routes of administration suitable for the methods of the invention include both systemic and local administration. As used herein, the term "systemic administration" means a mode of administration resulting in delivery of a pharmaceutical composition to essentially the whole body of the patient. Exemplary modes of systemic administration include, without limitation, intravenous injection and oral administration. The term "local administration," as used herein, means a mode of administration resulting in significantly more pharmaceutical composition being delivered to and about the eyes (or tumor or other target tissue) than to regions distal from the eyes (or tumor or other target tissue).

Systemic and local routes of administration useful in the methods of the invention encompass, without limitation, oral gavage; intravenous injection; intraperitoneal injection; intramuscular injection; subcutaneous injection; transdermal diffusion and electrophoresis; topical eye drops and ointments; periocular and intraocular injection including subconjunctival injection; extended release delivery devices including locally implanted extended release devices; and intraocular and periocular implants including bioerodible and reservoir-based implants.

Thus, in one aspect, a method of treating an ocular disorder associated with retinal neovascularization is practiced by local administration of the ligand binding molecule to the subject. For example, in some embodiments, a pharmaceutical composition comprising the ligand binding molecule is administered topically, or by local injection (e.g., by intraocular, e.g. intravitreal, injection), or is released from an intraocular or periocular implant such as a bioerodible or reservoir-based implant. The composition is preferably administered in an amount effective to inhibit VEGF-C and/or VEGF-D in the eye of the subject from binding to or stimulating VEGFR-2 and/or VEGFR-3 expressed in cells of the eye or vessels of the eye.

In the case of combination therapies, the administration of the ligand binding molecule and the additional agent can be sequential in time or concurrent. When administered sequentially, the administration of each can be by the same or different route. In one embodiment, an additional agent (e.g. a VEGF-A or PDGF inhibitor product) is administered within 90 days, 30 days, 10 days, 5 days, 24 hours, 1 hour, 30 minutes, 10 minutes, 5 minutes or one minute of administration of a ligand binding molecule. Where the additional agent is administered prior to the ligand binding molecule, the ligand binding molecule is administered within a time and in an amount such that the total amount of additional agent and ligand binding molecule is effective to treat or prevent the targeted indication, e.g. ocular disorder. Where the ligand binding molecule is administered prior to the additional agent, the additional agent is administered within a time and in an amount such that the total amount of additional agent and ligand binding molecule is effective to treat or prevent the targeted indication, e.g. ocular disorder.

Pharmaceutical compositions according to the invention may be formulated to release the ligand binding molecule and optionally the additional agent in a combination therapy substantially immediately upon administration or at any predetermined time period after administration, using controlled release formulations. For example, a pharmaceutical composition can be provided in sustained-release form. The use of immediate or sustained release compositions depends on the nature of the condition being treated. If the condition consists of an acute disorder, treatment with an immediate release form can be utilized over a prolonged release composition. For certain preventative or long-term treatments, a sustained released composition can also be appropriate.

Administration of the ligand binding molecule or both the ligand binding molecule and one or more additional agents in controlled release formulations can be useful where the ligand binding molecule, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose (LD50) to median effective dose (ED 5 0)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of degradation or metabolism of the active components. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes. Methods for preparing such sustained or controlled release formulations are well known in the art.

The ligand binding molecule and, if present, an additional agent, can also be delivered using a drug-delivery device such as an implant. As used herein, the term "implant" refers to any material that does not significantly migrate from the insertion site following implantation. An implant can be biodegradable, non-biodegradable, or composed of both biodegradable and non-biodegradable materials. A non-biodegradable implant can include, if desired, a refillable reservoir. Implants useful in the methods of the invention include, for example, patches, particles, sheets, plaques, microcapsules and the like, and can be of any shape and size compatible with the selected site of insertion, which can be, without limitation, the posterior chamber, anterior chamber, suprachoroid or subconjunctiva. It is understood that an implant useful in the invention generally releases the implanted pharmaceutical composition at an effective dosage to the eye of the patient over an extended period of time.

A variety of ocular implants and extended release formulations suitable for ocular release are well known in the art, as described, for example, in U.S. Pat. Nos. 5,869,079 and 5,443,505, the disclosures of which are incorporated herein by reference in their entireties. Ocular drug delivery devices can be inserted into a chamber of the eye, such as the anterior or posterior chamber or can be implanted in or on the sclera, choroidal space, or an avascularized region exterior to the vitreous. In one embodiment, the implant can be positioned over an avascular region, such as on the sclera, so as to allow for transscleral diffusion of the ligand binding molecules and any additional agents to the desired site of treatment, e.g., the intraocular space and macula of the eye. Furthermore, the site of transcleral diffusion can be proximal to a site of neovascularization such as a site proximal to the macula. Suitable drug delivery devices are described, for example, in U.S. Publication Nos. 2008/0286334; 2008/0145406; 2007/0184089; 2006/0233860; 2005/0244500; 2005/0244471; and 2005/0244462, and U.S. Pat. Nos. 6,808,719 and 5,322,691, the contents of each of which is herein incorporated by reference in its entirety.

In other embodiments, a ligand binding molecule described herein is applied to the eye via liposomes. In still another embodiment, the ligand binding molecule is contained within a continuous or selective-release device, for example, membranes such as, but not limited to, those employed in the Ocusert™ System (Alza Corp., Palo Alto, Calif.). As an additional embodiment, the ligand binding molecule is contained within, carried by, or attached to contact lenses which are placed on the eye. In yet another embodiment, the ligand binding molecule is contained within a swab or sponge which can be applied to the ocular surface. Another embodiment of the present invention involves the ligand binding molecule contained within a liquid spray which can be applied to the ocular surface.

In one embodiment, the implant comprises a ligand binding molecule and optionally, if present, an additional agent, dispersed in a biodegradable polymer matrix. The matrix can comprise PLGA (polylactic acid-polyglycolic acid copolymer), an ester-end capped polymer, an acid end-capped polymer, or a mixture thereof. In another embodiment, the implant comprises a ligand binding molecule and optionally, if present, an additional agent, a surfactant and a lipophilic compound. The lipophilic compound can be present in an amount of about 80-99% by weight of the implant. Suitable lipophilic compounds include, but are not limited to, glyceryl palmitostearate, diethylene glycol monostearate, propylene glycol monostearate, glyceryl monostearate, glyceryl monolinoleate, glyceryl monooleate, glyceryl monopalmitate, glyceryl monolaurate, glyceryl dilaurate, glyceryl monomyristate, glyceryl dimyristate, glyceryl monopalmitate, glyceryl dipalmitate, glyceryl mono stearate, glyceryl distearate, glyceryl monooleate, glyceryl dioleate, glyceryl monolinoleate, glyceryl dilinoleate, glyceryl monoarachidate, glyceryl diarachidate, glyceryl monobehenate, glyceryl dibehenate, and mixtures thereof. In another embodiment, the implant comprises a ligand binding molecule and optionally, if present, an additional agent, housed within a hollow sleeve. The ligand binding molecule and optionally, if present, an additional agent, are delivered to the eye by inserting the sleeve into the eye, releasing the implant from the sleeve into the eye, and then removing the sleeve from the eye. An example of this delivery device is described in U.S. Publication No. 2005/0244462, which is hereby incorporated by reference in its entirety.

In one embodiment, the implant is a flexible ocular insert device adapted for the controlled sustained release of a ligand binding molecule and optionally, if present, an additional agent, into the eye. In one embodiment, the device includes an elongated body of a polymeric material in the form of a rod or tube containing a ligand binding molecule and optionally, if present, an additional agent, and with at least two anchoring protrusions extending radially outwardly from the body. The device may have a length of at least 8 mm and the diameter of its body portion including the protrusions does not exceed 1.9 mm. The sustained release mechanism can, for example, be by diffusion or by osmosis or bioerosion. The insert device can be inserted into the upper or lower formix of the eye so as to be independent of movement of the eye by virtue of the formix anatomy. The protrusions can be of various shapes such as, for example, ribs, screw threads, dimples or bumps, truncated cone-shaped segments or winding braid segments. In a further embodiment, the polymeric material for the body is selected as one which swells in a liquid environment. Thus a device of smaller initial size can be employed. The insert device can be of a size and configuration such that, upon insertion into the upper or lower formix, the device remains out of the field of vision so as to be well retained in place and imperceptible by a recipient over a prolonged period of use. The device can be retained in the upper or lower formix for 7 to 14 days or longer. An example of this device is described in U.S. Pat. No. 5,322,691, which is hereby incorporated by reference in its entirety.

In another aspect, a method of inhibiting neovascularization in a subject who has been diagnosed with a tumor practiced by local administration of the ligand binding molecule to the subject. For example, in some embodiments, a pharmaceutical compositions comprising the ligand binding molecule is administered locally to the tumor or to the organ or tissue from which the tumor has been surgically removed. In such embodiments, the composition is preferably administered in an amount effective to inhibit neovascularization in the tumor.

In instances where the ligand binding molecule is a nucleic acid molecule, administration of a pharmaceutical composition containing the nucleic acid molecule can be carried out using one of numerous methods well known in the art of gene therapy. Such methods include, but are not limited to, lentiviral transformation, adenoviral transformation, cytomegaloviral transformation, microinjection and electroporation.

Kits and Unit Doses

The invention also relates to kits comprising one or more pharmaceutical compositions and instructions for use. A ligand binding molecule may be packaged or formulated together with another ligand binding molecule or other therapeutic described herein, e.g., in a kit or package or unit dose, to permit co-administration; these two components may be formulated together (i.e. in admixture) or in separate compositions (i.e. not in admixture) and in individual dosage amounts. Each of the kits' compositions can be contained in a container. In some embodiments, the two components to the kit/unit dose are packaged with instructions for administering the two compounds to a human subject for treatment of one of the disorders and diseases described herein.

The kits can comprise a container. The container can be used to separate components and include, for example, a divided bottle or a divided foil packet. The separate compositions may also, if desired, be contained within a single, undivided container. The kits can also comprise directions for the administration of the components. The kits are particularly advantageous when the separate components are administered in different dosage forms, are administered at different dosage levels, or when titration of the individual antagonists is desired.

All publications and patents mentioned herein are hereby incorporated by reference in their entirety as if each individual publication or patent was specifically and individually indicated to be incorporated by reference. In case of conflict, the present application, including any definitions herein, will control.

EXAMPLES

Example 1—ECD Fragments of VEGFR Proteins

Experiments were performed to characterize fragments and variants and fusions of VEGFR-3 and/or VEGFR-2 and/or VEGFR-1 that are effective to bind target ligands, such as VEGF-C and/or VEGF-D and/or VEGF-A. See International Patent Publication Nos: WO 2005/087808, WO 2005/000895, WO 2006/088650, WO 2006/099154, WO 2004/106378, WO 2005/123104 and U.S. Pat. No. 7,855,178, all of which are incorporated herein by reference in their entireties. These studies demonstrate that the ECDs of these receptors can be truncated, and also that domains from different receptors can be recombined, to form ligand binding molecules.

Example 2—Generation of VGX-301-ΔN2 Ligand Binding Molecule

A ligand binding molecule comprising Ig-like domains I-III of VEGFR-3 (referred to herein as "VGX-300") was prepared as described in Makinen et al., Nat. Med., 7:199-205, 2001, the disclosure of which is incorporated herein by reference in its entirety.

A key feature of the VGX-300 molecule is that it contains 12 glycosylation sites; 2×6 potential N-linked glycosylation sites, 5 on each receptor fragment (VEGFR-3 Ig-like domains I, II, and III) and 1 on each Fc region gamma chain. There is no evidence for O-linked glycosylation.

Glycosylation characteristics can have an effect on PK but, Fc glycans have little effect on PK (Jones et al, Glycobiology, 17(5), 2007 pp. 529-540). Briefly, the asialoglycoprotein receptor binds to complex-type N-linked glycan structures in which two or more sialic acids are absent, wherein the underlying galactose (Gal) residues become the terminal saccharides. In addition, the mannose (Man) receptor recognizes high-Man N-linked glycans and terminal N-acetylglucosamine (tGlcNAc) residues. Both of these receptors can cause rapid metabolic clearance of proteins.

In order to identify which glycosylation sites are important for product activity, sequential deletion of each of the five putative N-linked sites was undertaken. Five primer pairs were used to introduce single mutations into the VGX-300 coding region to destroy the consensus attachment for each of the five N-linked glycans (N-Q).

The primer pairs used are as follows:

N1 sense:
(SEQ ID NO: 12)
5' GACCCCCCCGACCTTGCAGATCACGGAGGAGTCACAC 3'

N1 anti-sense:
(SEQ ID NO: 13)
5' GTGTGACTCCTCCGTGATCTGCAAGGTCGGGGGGGTC 3'

N2 sense:
(SEQ ID NO: 14)
5' CTGCACGAGGTACATGCCCAGGACACAGGCAGCTACGTC 3'

N2 anti-sense:
(SEQ ID NO: 15)
5' GACGTAGCTGCCTGTGTCCTGGGCATGTACCTCGTGCAG 3'

N3 sense:
(SEQ ID NO: 16)
5' GTCCATCCCCGGCCTCCAAGTCACGCTGCGCTCGC 3'

N3 anti-sense:
(SEQ ID NO: 17)
5' GCGAGCGCAGCGTGACTTGGAGGCCGGGGATGGAC 3'

N4 sense:
(SEQ ID NO: 18)
5' GGGAGAAGCTGGTCCTCCAGTGCACCGTGTGGGCTGA 3'

N4 anti-sense:
(SEQ ID NO: 19)
5' TCAGCCCACACGGTGCACTGGAGGACCAGCTTCTCCC 3'

N5 sense:
(SEQ ID NO: 20)
5' AGCATCCTGACCATCCACCAGGTCAGCCAGCACGACCT 3'

N5 anti-sense:
(SEQ ID NO: 21)
5' AGGTCGTGCTGGCTGACCTGGTGGATGGTCAGGATGCT 3'

The presence of mutations was confirmed by sequencing, following which the plasmid vectors were transiently transfected into 293T cells (HEK). Culture samples were analyzed by western blot. Viable constructs were then progressed to transient suspension-adapted 293F cells (HEK) and the supernatants purified by ProSepA chromatography and gel filtration, for further testing by enzyme-linked immunosorbant assay (ELISA) and BaF/3 bioassay to determine yield and activity. Table 3 below summarizes expression data and activity of each resulting mutant.

TABLE 3

| Mutant | Gel Filtration Profile | Yield | Activity | |
|---|---|---|---|---|
| | | | ELISA | BaF/3 |
| Parent | Monomer evident, some aggregate | Fair | Reference | Reference |
| ΔN1 | Monomer evident, substantial aggregate | Poor | ≥1 log less than parent | ≥1 log less than parent |
| ΔN2 | Monomer evident, some aggregate | Fair | Comparable to parent | Comparable to parent |
| ΔN3 | Severe aggregation | Poor | ≥1 log less than parent | ≥1 log less than parent |
| ΔN4 | Some monomer evident, significant aggregate | Poor | ≥1 log less than parent | ≥1 log less than parent |
| ΔN5 | Some monomer evident, significant aggregate | Poor | ≥1 log less than parent | ≥1 log less than parent |

Table 3 shows that only the N2 mutant (referred to herein as "VGX-301-ΔN2") exhibited favorable expression and activity characteristics relative to the parent molecule (i.e., VGX-300). VGX-301-ΔN2 and VGX-300 parent were produced in CHO and HEK cells by transient expression, and the pharmacokinetics (PK) of each molecule was examined as follows. Sprague-Dawley rats were allocated into either groups of 2, 3 or 5 per compound in each experiment. The rats in each group received a single dose of VGX-300 or VGX-301-ΔN2 via intravenous administration as a bolus injection at a dose concentration of 1 mg/kg. Interim blood samples were collected by lateral tail vein puncture on Day −1 (Pre-dose) and a total of 12 time points post-dose, ranging from 5 min to 14-days post-initial treatment. Serum samples were prepared from each blood sample and tested using a quantitative VEGF-C ligand-capture ELISA to determine the circulating concentration of each compound. The results of these analyses were then used for calculation of the pharmacokinetic parameters. PK data of VGX-300 and VGX-301-ΔN2 is provided below in Table 4.

TABLE 4

| Compound | Dose (mg/kg) | $AUC_{0\text{-}last/Dose}$ (hr * ng/mL) | $C_{max}$ (ng/mL) | $T_{1/2}$ (el) (hr) |
|---|---|---|---|---|
| Transient CHO Expression (Expt 1) | | | | |
| VGX-300 | 1 | 15,115 | 5,702 | 16.9 |
| VG-301-ΔN2 | 1 | 23,236 | 12,076 | 22.6 |
| Transient CHO Expression (Expt 2) | | | | |
| VGX-300 | 1 | 35,310 | 16,000 | 46 |
| VGX-301-ΔN2 | 1 | 55,071 | 20,000 | 42 |
| Transient HEK Expression | | | | |
| VGX-300 | 1 | 18,738 | 8,500 | 6.4 |
| VGX-301-ΔN2 | 1 | 90,750 | 13,250 | 15.3 |

Figure 1B:
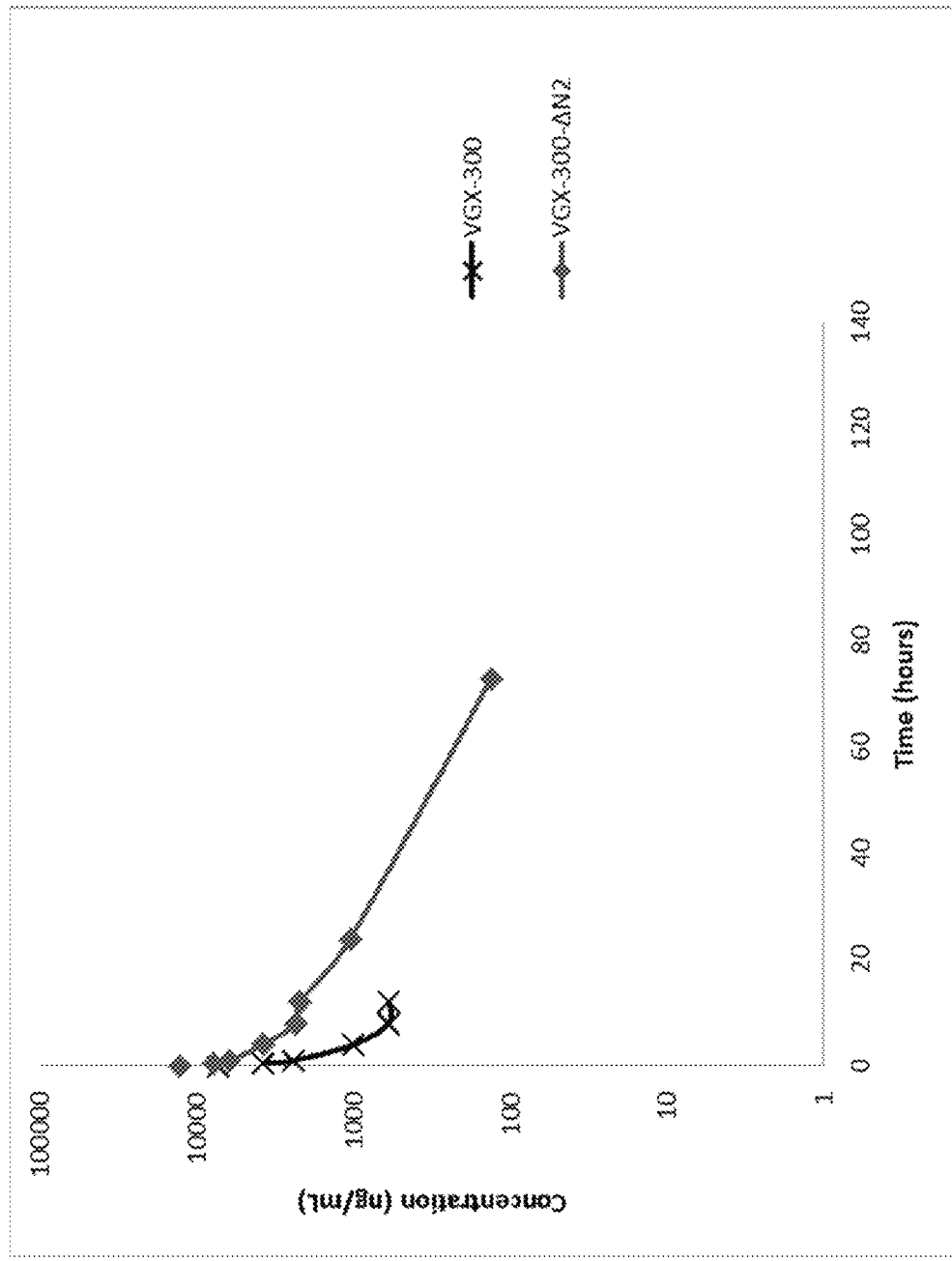
FIG. 1B shows the PK profiles of VGX-300 and VGX-301-ΔN2 produced by transient HEK expression.

The PK curves provided in FIGS. 1A and 1B and the data from Table 4 show that the VGX-301-ΔN2 may have a beneficial effect on PK by comparison to VGX-300 produced in the same expression system.

Figure 2A:
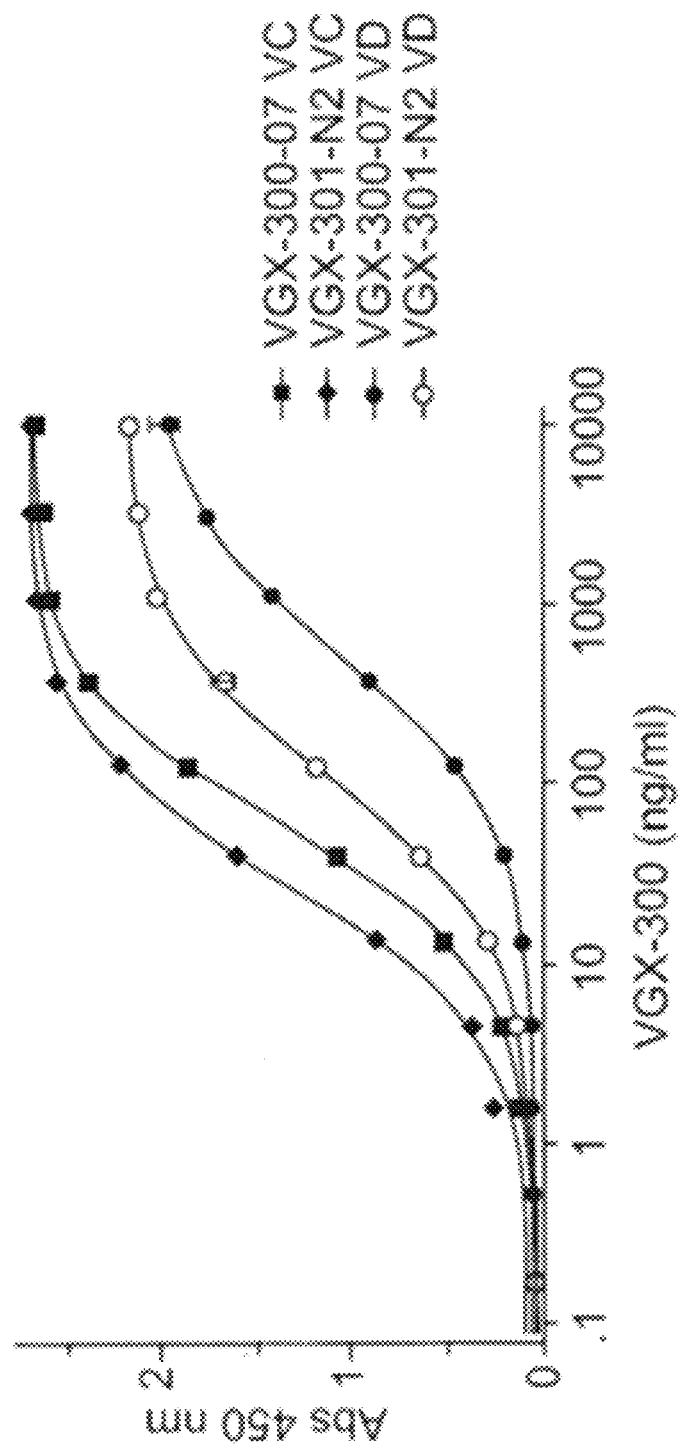
Figure 3A:
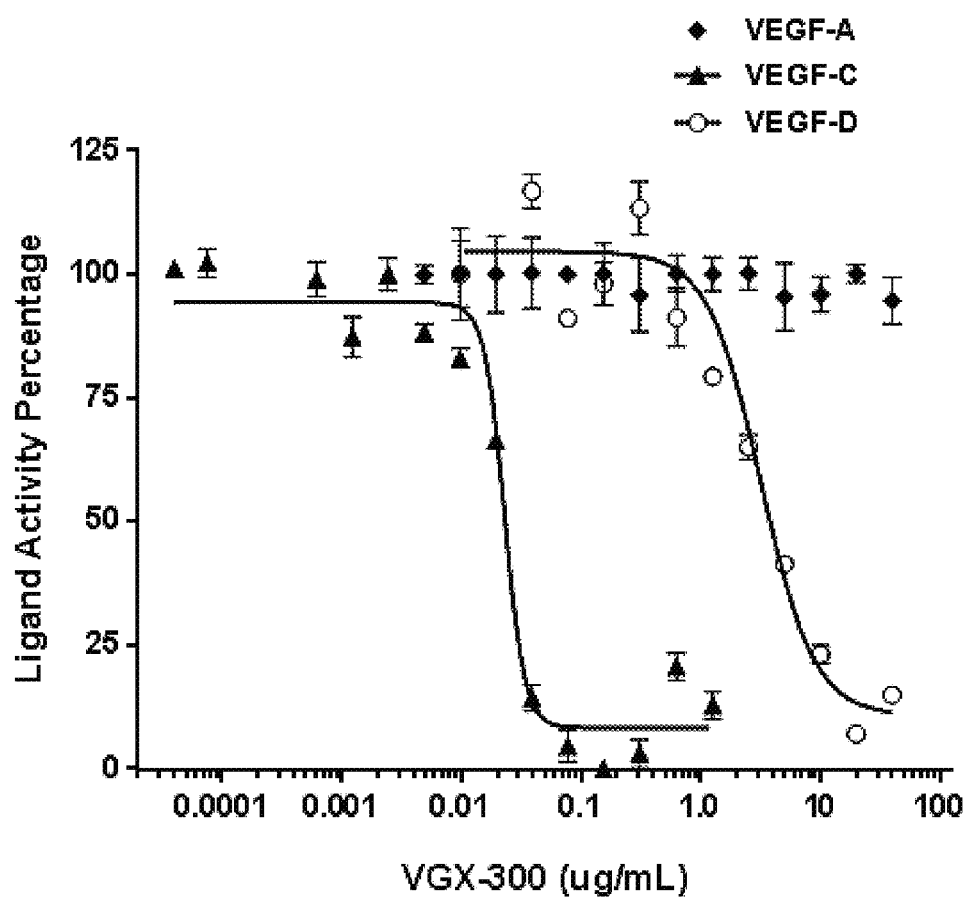
FIG. 3A and FIG. 3B show VGX-300 blocks VEGF-C and VEGF-D binding and cross-linking of VEGFR-2 (FIG. 3A) and VEGFR-3 (FIG. 3B).
Figure 3B:
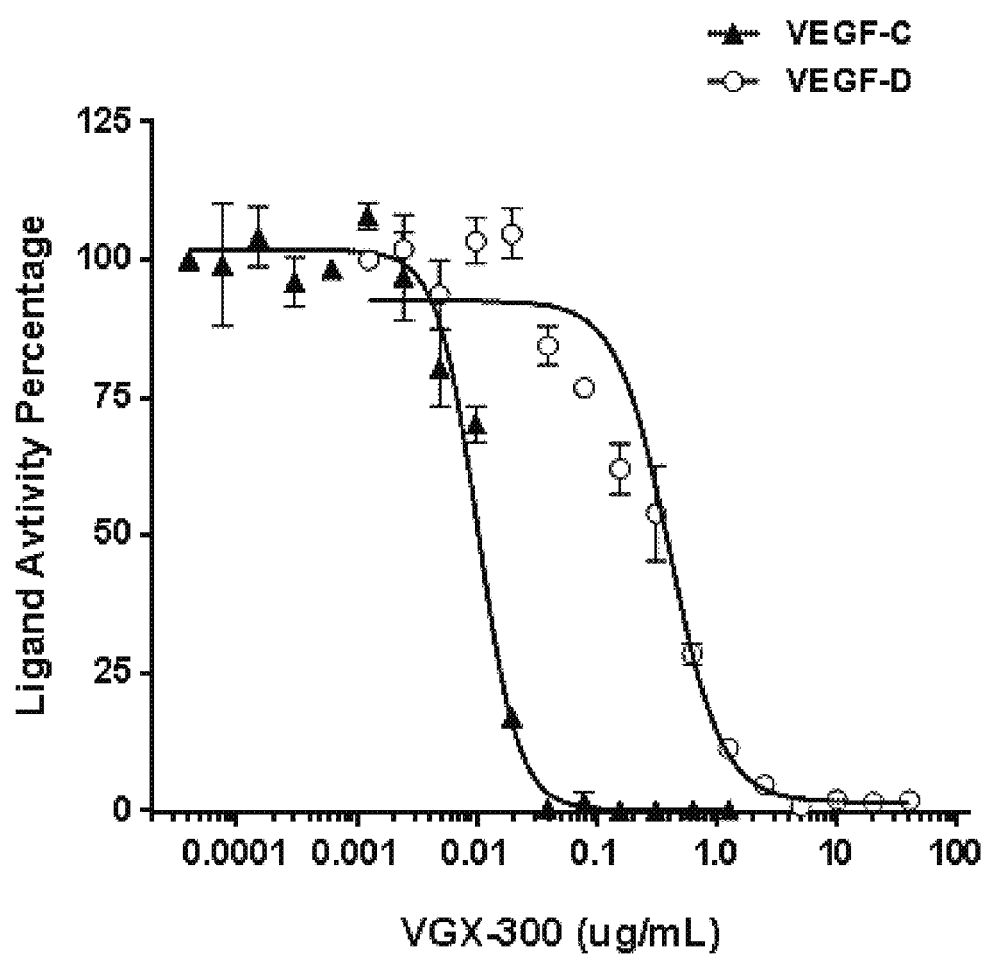
Figure 4B:
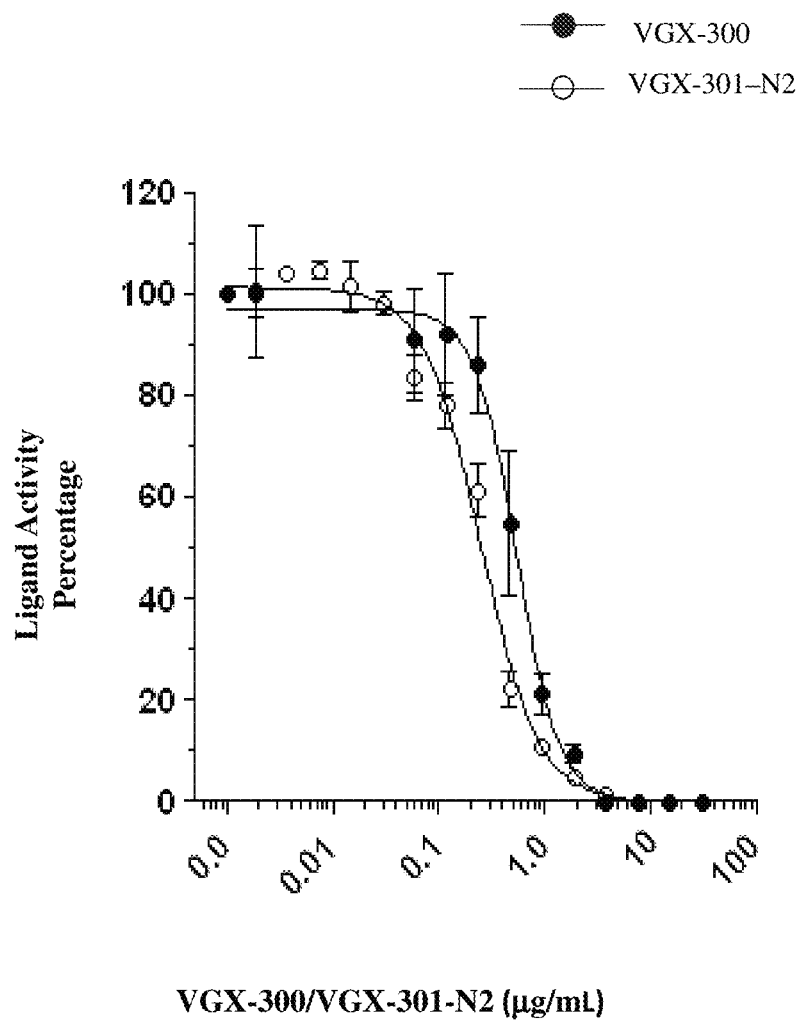
Figure 5A:
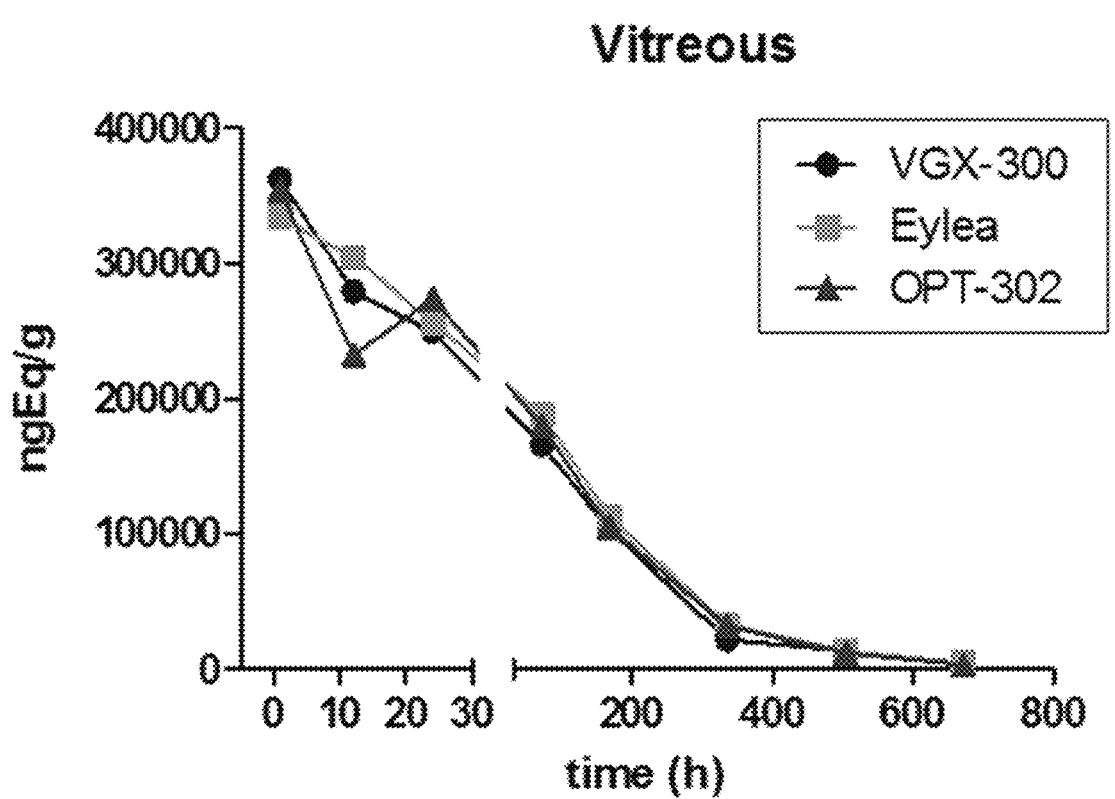
FIG. 5A-FIG. 5E show the pharmacokinetics and ocular biodistribution in rabbits following intravitreal administration.
Figure 5B:
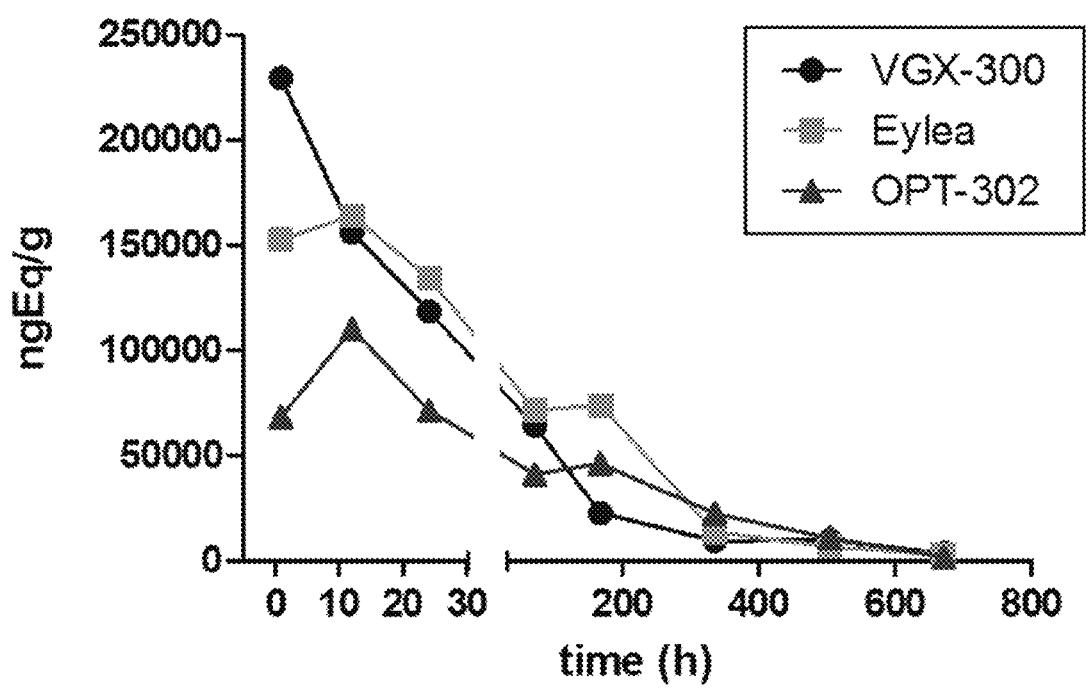
Figure 5C:
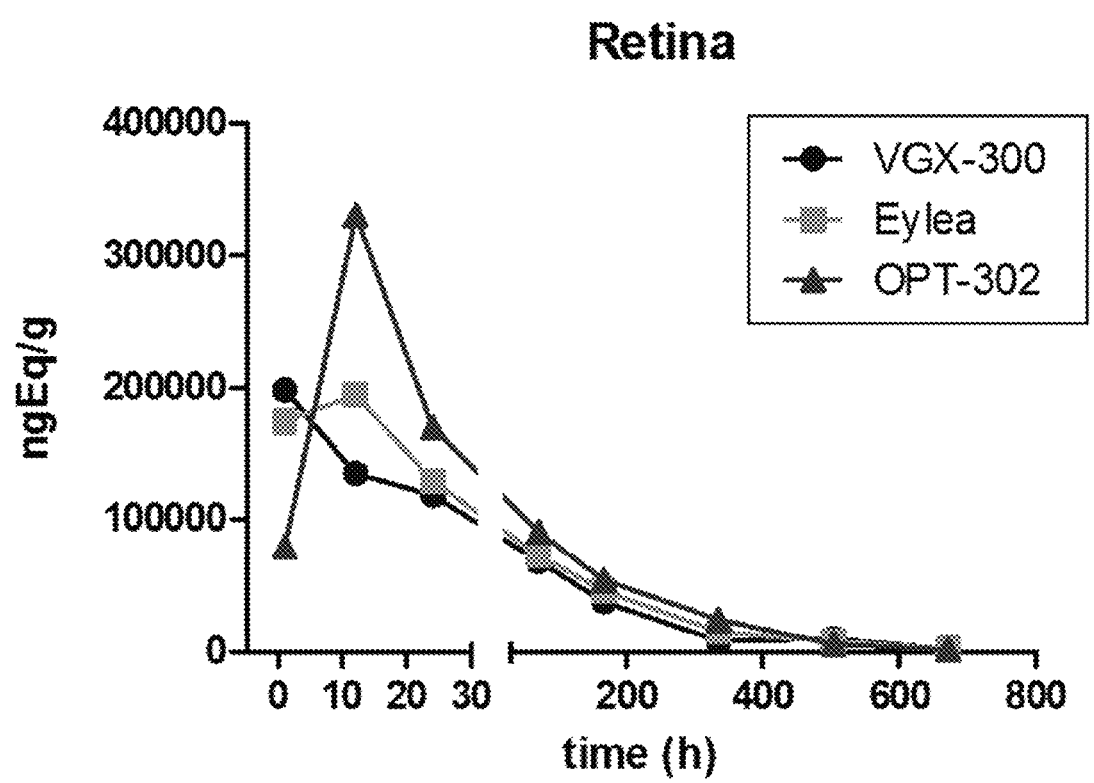
Figure 5D:
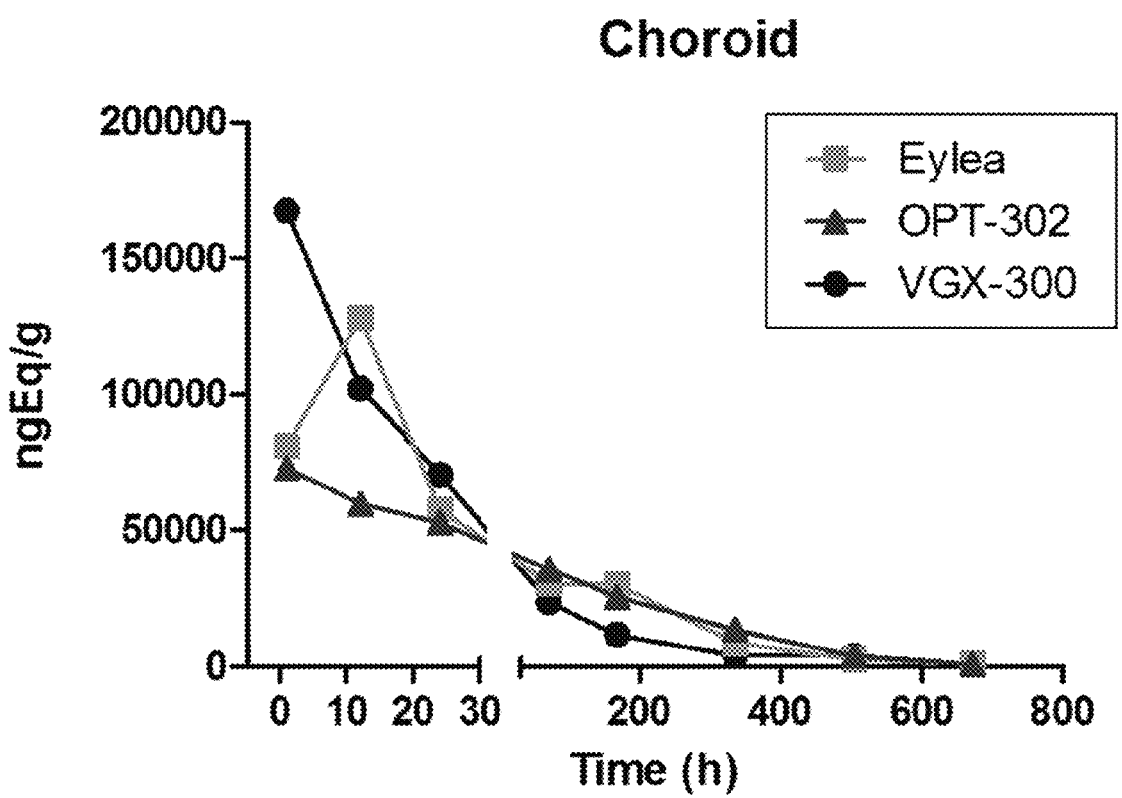
Figure 5E:
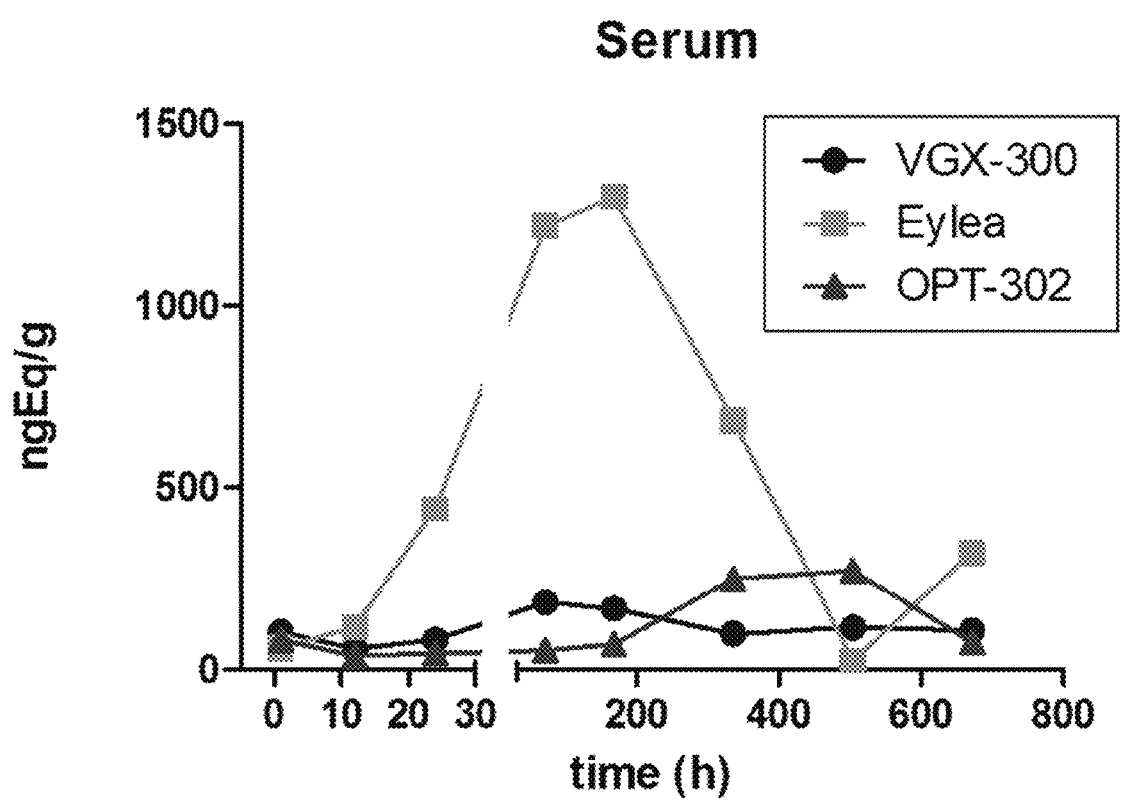

To determine the specificity of VGX-300 and VGX-301-ΔN2 binding to VEGF-C and VEGF-D, VEGF-C or VEGF-D (2 pg/mL) were pre-coated onto ELISA plates and used as capture antigens. Increasing concentrations of either VGX-300 or VGX-301-ΔN2 (0 to 10 pg/mL) were applied to the plate and detected with rabbit anti-human IgG-horseradish peroxidase conjugate using a tetramethylbenzidine substrate kit. Results indicated that both VGX-300 and VGX-301-ΔN2 bound to both VEGF-C and VEGF-D. See FIG. 2. Surprisingly, VGX-301-ΔN2 demonstrated stronger binding to both ligands than VGX-300.

Example 4—VGX-300 and VGX-301-ΔN2 Binding Affinity

The binding of VEGF-C and VEGF-D to VGX-300 or VGX-301-ΔN2 was analyzed by surface plasmon resonance (SPR) performed using the PrateOn XPR36 biosensor (Bio-Rad). Either VGX-300 or VGX-301-ΔN2 was captured onto protein G' immobilized onto a GLM sensor chip and the affinity of the molecule to VEGF-C or VEGF-D was measured. The results of the affinity experiment are provided below in Table 5.

TABLE 5

| | $k_a$ (M$^{-1}$s$^{-1}$) × 10$^6$ | $K_d$ (s$^{-1}$) × 10$^{-5}$ | $K_D$ (pM) |
|---|---|---|---|
| Human VEGF-C | | | |
| VGX-300 | 2.18 ± 0.05 | 1.11 ± 0.12 | 5.1 ± 0.6 |
| VGX-301-ΔN2 | 2.79 ± 0.04 | 1.03 ± 0.08 | 3.7 ± 0.3 |
| Human VEGF-D | | | |
| VGX-300 | 4.9 ± 0.1 | 3.23 ± 0.16 | 625 ± 21 |
| VGX-301-ΔN2 | 5.7 ± 0.1 | 3.88 ± 0.03 | 677 ± 12 |

The data presented in Table 5 above shows that the VGX-300 and VGX-301-ΔN2 samples bound human VEGF-C and VEGF-D with near identical affinities, with both molecules showing stronger binding to VEGF-C than VEGF-D.

Example 5—VGX-301-ΔN2 Blocks VEGF-C and VEGF-D Binding and Cross-Linking of VEGFR-3

Cell-based assays have been developed to evaluate the capacity of VEGF family ligands to bind and cross-link VEGFR-2 and VEGFR-3. These bioassays have been employed to study the neutralizing activity of VGX-300 and VGX-301-ΔN2. The bioassay cell lines consist of the mouse IL-3 dependent pro-B cell line Ba/F3, stably transfected with a chimeric receptor consisting of the ECD of VEGFR-2 or VEGFR-3, fused in-frame to the transmembrane and intracellular domains of the mouse erythropoietin receptor (as described in Example 5 of WO 2005/087808, the disclosure of which is incorporated herein by reference in its entirety). In the absence of IL-3, these cells survive and proliferate only in the presence of growth factors capable of binding and cross-linking the ECD of the respective VEGFR.

Briefly, Ba/F3 cells transfected with VEGFR-2 or VEGFR-3 (10,000 cells/well; 96 well plate) were cultured in media supplemented with VEGF-C or VEGF-D in the presence of increasing concentrations of VGX-300 of VGX-301-ΔN2 (0-100 μg/mL) for 48 hours at 37° C. Cell proliferation was measured using WST 1 reagent; cells were incubated for 4 hours at 37° C. with WST-1 and the absorbance measured at 450 nm (n=3; error bars=standard error of the mean, SEM).

Results indicated that VGX-300 neutralized the activity of VEGF-C and VEGF-D, as demonstrated by the dose-responsive inhibition of VEGF-C and VEGF-D in the VEGFR-2 and VEGFR-3 Ba/F3 bioassays. VGX-300 showed enhanced potency in neutralizing VEGF-C compared to VEGF-D in both the VEGFR-2 and -3 assays. See FIGS. 3A-3B and 4A-4B.

Analysis of VGX-301-ΔN2 demonstrated that this molecule was also able to block both VEGF-C and VEGF-D from binding to VEGFR-3. The neutralizing activity of VGX-301-N2 was slightly stronger than that of VGX-300. See FIGS. 4A-4B. Table 6 shows the binding (IC50) of VGX-300 and VGX-301-ΔN2 to VEGF-C and VEGF-D in the VEGFR-3 Ba/F3 bioassay.

TABLE 6

| | VGX-300 $IC_{50}$ | VGX-301-ΔN2 $IC_{50}$ |
|---|---|---|
| VEGF-D ligand 300 ng/mL | 544.9 | 251.7 |
| VEGF-C ligand 5 ng/mL | 6.8 | 4.5 |

Example 6—Ocular Distribution and Pharmacokinetics of VGX-300 and VGX-301ΔN2 Following Intravitreal Administration This study was conducted to investigate the ocular distribution and pharmacokinetics of VGX-300, VGX-301-ΔN2 and Aflibercept (EYLEA) following a single intravitreal dose to pigmented rabbits.

The study design consisted of 3 groups, 8 female rabbits allocated per group. Animals are administered 500 μg of radiolabelled VGX-300, VGX-301-ΔN2 or Aflibercept via a 50 μL bolus intravitreal injection into both eyes.

| Group | Number of Females | Formulation | Dose Route | Target Dose Level | Target Dose Volume (µL/eye) | Samples Collected |
|---|---|---|---|---|---|---|
| 1 | 8 | [$^{125}$I]VGX-300 | IVT | 500 µg | 50 | Blood and ocular tissues |
| 2 | 8 | [$^{125}$I]Aflibercept (EYLEA) | IVT | 500 µg | 50 | Blood and ocular tissues |
| 3 | 8 | [$^{125}$I]VGX-301-ΔN2 | IVT | 500 µg | 50 | Blood and ocular tissues |

One animal per group was euthanized at 1, 12, 24, 72, 168, 366, 504 and 672 hours following dose administration. Blood, processed to serum, and selected ocular tissues were collected at each time point and the concentration of radioactivity determined by radioanalysis. The ocular tissues collected included the aqueous humor, choroid, cornea, iris-cilary body (ICB), lens, optic nerve, retina, retinal pigmented epithelium (RPE), sclera, trabecular meshwork and vitreous humor. FIGS. 5A-5E show the mean concentrations of radioactivity in various tissues and serum over the time period monitored.

The test articles, $^{125}$I-VGX-300, $^{125}$I-Aflibercept (EYLEA) and $^{125}$I-VGX-301-ΔN2, were well tolerated, stable in the vitreous humor and had prolonged exposure to ocular tissues of both the posterior segment and the anterior segment. Although there were differences in the serum exposure of $^{125}$I-VGX-300 and $^{125}$I-VGX-301-ΔN2 following intravitreal administration, both $^{125}$I-VGX-300 and $^{125}$I-VGX-301-ΔN2 had only minor systemic exposure compared to that of aflibercept (EYLEA), likely as a result of clearance via absorption into the choroid and also by aqueous humor outflow. The PK and biodistribution of $^{125}$I-VGX-300 and $^{125}$I-VGX-301-ΔN2 observed in this study were similar for both compounds, and comparable to that of $^{125}$I-Aflibercept (EYLEA).

Example 7—Retinopathy of Prematurity Model

The following Example is an exemplary assay to evaluate VGX-300 and VGX-301-ΔN2 for their ability to inhibit the onset of retinal neovascularization using the ROP model. In this model, postnatal day 7 (P7) mice are exposed to hyperoxia (75% oxygen) for 5 days (to P12). After hyperoxic exposure, P12 mice are returned to normoxia, and administered an intravitreal injection of human isotype control antibody, VGX-300, VGX-301-ΔN2, Eylea (VEGF-Trap), VGX-300+Eylea or VGX-301-ΔN2+Eylea. All mice are then housed under normoxic conditions for 5 days before sacrifice at P17, enucleation and fixation in 10% formalin/PBS. Vessels will be quantified in each group using H&E and/or IHC staining methods.

Example 8—Argon Laser-Induced Choroidal Neovascularization (CNV)

In this model of age-related macular degeneration (AMD), CNV is induced by argon laser-induced rupture of Bruch's membrane in mice on Day 0 (3 burns per mouse). Groups of 10 mice are studied and treatment administered via weekly intravitreal injections (at day 0 and day 7) of human isotype control antibody, VGX-301-ΔN2, VGX-300, Eylea (VEGF-Trap), VGX-301-ΔN2+Eylea or VGX-300+Eylea. At day 14, animals are sacrificed and choroidal flat mounts prepared and stained with ICAM-2 to visualize the neovascularisation by fluorescence microscopy.

It is contemplated that VGX-301-ΔN2, as a single-agent, will significantly inhibit choroidal neovascularisation in a mouse model of neovascular AMD, comparable to the effect demonstrated by Eylea®.

Example 9—Inhibitory Effect of Ligand Binding Molecules on VEGF-C Mediated Tumor Growth and Metastasis To demonstrate the ability of a ligand binding molecule described herein to inhibit tumor growth and/or metastasis, any accepted tumor model may be employed. Exemplary models include animals predisposed to developing various types of cancers, animals injected with tumors or tumor cells or tumor cell lines from the same or different species, including optionally cells transformed to recombinantly overexpress one or more growth factors such as VEGF-C, or VEGF-D. To provide a model for tumors in vivo in which multiple growth factors are detectable, it is possible to transform tumor cell lines with exogenous DNA to cause expression of multiple growth factors.

A ligand binding molecule described herein may be administered directly, e.g., in protein form by i.v. transfusion or by implanted micropumps, or in nucleic acid form as part of a gene therapy regimen. Subjects are preferably grouped by sex, weight, age, and medical history to help minimize variations amongst subjects.

Efficacy is measured by a decrease in tumor, size (volume) and weight. One may also examine the nature of the effect on tumor size, spreads (metastases) and number of tumors. For example, use of specific cell markers can be used to show the effect on angiogenesis relative to lymphangiogenesis, a VEGF-A binding construct expected to have a greater effect on the former, and a VEGF-C binding construct expected to have a greater effect on the latter. Animals may be looked at as a whole for survival time and changes in weight. Tumors and specimens are examined for evidence of angiogenesis, lymphangiogenesis, and/or necrosis.

SCID mice may be used as subjects for the ability of a ligand binding molecule described herein to inhibit or prevent the growth of tumors. The ligand binding molecule used in the therapy is generally chosen such that it binds to a growth factor ligand expressed by the tumor cell, especially growth factors that are overexpressed by the tumor cell relative to non-neoplastic cells in the subject. In the SCID model, tumor cells, e.g., MCF-7 cells, may be transfected with a virus encoding a particular growth factor under the control of a promoter or other expression control sequence that provides for overexpression of the growth factor as described in WO 02/060950. Alternatively, other cell lines may be employed, e.g., HT-1080, as described in U.S. Pat. No. 6,375,929. One may transfect the tumor cells with as many growth factor ligands as one desires to overexpress, or a tumor cell line may be chosen that already overexpresses one or more growth factor ligands of interest. One group of subjects is implanted with cells that have been mock-transfected, i.e., with a vector lacking a growth factor ligand insert.

Either before, concurrently with, or after the tumor implantation of the above-described cells, subjects are treated with a particular ligand binding molecule. There are a number of different ways of administering the ligand binding molecule. In vivo and/or ex vivo gene therapy may be employed. For example, cells may be transfected with a adenovirus, or other vector, that encodes the ligand binding molecule and implanted with the tumor cells expressing the growth factor(s), the cells transfected with the ligand binding molecule may be the same as those transformed with growth factor(s) (or already overexpressing the growth factor(s)). In some embodiments, an adenovirus that encodes that ligand binding molecule is injected in vivo, e.g., intravenously. In some embodiments, the ligand binding molecule itself (e.g., in protein form) is administered either systematically or locally, e.g., using a micropump. When testing the efficacy of a particular binding construct, at least one control is normally employed. For example, in the case of a vector-based therapy, a vector with an empty insert or LacZ is employed, or the insert may be a ligand binding molecule comprising a complete ECD of VEGFR-3 capable of binding VEGF-C or VEGF-D, such a control may employ more than one ECD construct if necessary (e.g., for binding multiple ligands if binding constructs with multiple ligand binding affinities are employed).

A. Exemplary Procedures

Preparation of Plasmid Expression Vectors, Transfection of Cells, and Testing of the Same A cDNA encoding VEGF-C or VEGF-D or combinations thereof are introduced into a pEBS7 plasmid (Peterson and Legerski, *Gene*, 107: 279-84, 1991.). This same vector may be used for the expression of the ligand binding molecule.

The MCF-7S1 subclone of the human MCF-7 breast carcinoma cell line is transfected with the plasmid DNA by electroporation and stable cell pools are selected and cultured as previously described (Egeblad and Jaattela, *Int. J. Cancer*, 86: 617-25, 2000). The cells are metabolically labeled in methionine and cysteine free MEM (Gibco) supplemented with 100 µCi/ml $^{35}$S-methionine and $^{35}$S-cysteine (Redivue Pro-Mix, Amersham Pharmacia Biotech). The labeled growth factors are immunoprecipitated from the conditioned medium using antibodies against the expressed growth factor(s). The immunocomplexes and the binding complexes are precipitated using protein A sepharose (Amersham Pharmacia Biotech), washed twice in 0.5% BSA, 0.02% Tween 20 in PBS and once in PBS and analyzed in SDS-PAGE under reducing conditions.

Subject Preparation and Treatment

Cells (20,000/well) are plated in quadruplicate in 24-wells, trypsinized on replicate plates after 1, 4, 6, or 8 days and counted using a hemocytometer. Fresh medium is provided after 4 and 6 days. For the tumorgenesis assay, sub-confluent cultures are harvested by trypsination, washed twice and $10^7$ cells in PBS are inoculated into the fat pads of the second (axillar) mammary gland of ovariectomized SCID mice, carrying subcutaneous 60-day slow-release pellets containing 0.72 mg 17β-estradiol (Innovative Research of America). The ovarectomy and implantation of the pellets are performed 4-8 days before tumor cell inoculation.

The cDNA coding for the binding construct(s) is subcloned into the pAdBgIII plasmid and the adenoviruses produced as previously described (Laitinen et al., *Hum. Gene Ther.*, 9: 1481-6, 1998). The ligand binding molecule(s) or LacZ control (Laitinen et al., *Hum. Gene Ther.*, 9: 1481-6, 1998) adenoviruses, $10^9$ pfu/mouse, are injected intravenously into the SCID mice 3 hours before the tumor cell inoculation.

Analysis of Treatment Efficacy

Tumor length and width are measured twice weekly in a blinded manner, and the tumor volume are calculated as the length×width×depth×0.5, assuming that the tumor is a hemi-ellipsoid and the depth is the same as the width (Benz et al., *Breast Cancer Res. Treat.*, 24: 85-95, 1993).

The tumors are excised, fixed in 4% paraformaldehyde (pH 7.0) for 24 hours, and embedded in paraffin. Sections (7 µm) are immunostained with monoclonal antibodies against, for example, PECAM-1 (Pharmingen), VEGFR-1, VEGFR-2, VEGFR-3 (Kubo et al., *Blood*, 96: 546-553, 2000) or PCNA (Zymed Laboratories), PDGFR-α, PDGFR-β or polyclonal antibodies against LYVE-1 (Banerji et al., J Cell Biol, 144: 789-801, 1999), VEGF-C (Joukov et al., *EMBO J.*, 16: 3898-911, 1997), laminin according to published protocols (Partanen et al., *Cancer*, 86: 2406-12, 1999), or any of the growth factors. The average of the number of the PECAM-1 positive vessels are determined from three areas (60× magnification) of the highest vascular density (vascular hot spots) in a section. All histological analyses are performed using blinded tumor samples.

Three weeks after injection of adenovirus constructs and/or protein therapy, four mice from each group are narcotized, the ventral skin is opened and a few microliters 3% Evan's blue dye (Sigma) in PBS is injected into the tumor. The drainage of the dye from the tumor is followed macroscopically.

Imaging and monitoring of blood and blood proteins to provide indication of the health of subjects and the extent of tumor vasculature may also be performed.

Example 10—Effects on Tumor Progression in Subjects Using a Combined Therapy of a Ligand Binding Molecule and a Chemotherapeutic Agent This study is carried out to test the efficacy of using a ligand binding molecule described herein in combination with other anti-cancer therapies. Such therapies include chemotherapy, radiation therapy, anti-sense therapy, RNA interference, and monoclonal antibodies directed to cancer targets. The combinatorial effect may be additive, but it is preferably synergistic in its anti-cancer effects, e.g., prevention, suppression, regression, and elimination of cancers, prolongation of life, and/or reduction in side-effects.

Subjects are divided into groups with one group receiving a chemotherapeutic agent, one group receiving a ligand binding molecule, and one group receiving both a chemotherapeutic agent and a ligand binding molecule at regular periodic intervals, e.g., daily, weekly or monthly. In human studies, the subjects are generally grouped by sex, weight, age, and medical history to help minimize variations among subjects. Ideally, the subjects have been diagnosed with the same type of cancer. In human or non-human subjects, progress can be followed by measuring tumor size, metastases, weight gain/loss, vascularization in tumors, and white blood cells counts.

Biopsies of tumors are taken at regular intervals both before and after beginning treatment. For example, biopsies are taken just prior to treatment, at one week, and then at one month intervals, thereafter, or whenever possible, e.g., as tumors are excised. One examines the biopsies for cell markers, and overall cell and tissue morphology to assess the effectiveness of the treatment. In addition, or in the alternative, imagining techniques may be employed.

For non-human animal studies, an additional placebo control may be employed. Animal studies, performed in accordance with NIH guidelines, also provide the advantage of the insertion of relatively uniform cancer cell population, and tumors that selectively overproduce the one or more growth factors targeted by the ligand binding molecule.

The invention claimed is:

1. A purified or isolated, soluble, ligand binding polypeptide comprising an amino acid sequence having at least 95% identity to the sequence of amino acids defined by positions 47-115 of SEQ ID NO: 2, with the proviso that positions of the polypeptide corresponding to positions 104-106 of SEQ ID NO: 2 are not identical to N-X-S or N-X-T,
wherein the polypeptide binds to at least one ligand polypeptide selected from human VEGF-C, VEGF-D, and PlGF.

2. The purified or isolated, soluble, ligand binding polypeptide according to claim 1, comprising an amino acid sequence having at least 95% identity to the sequence of amino acids defined by positions 47-210 of SEQ ID NO: 2, with the proviso that positions of the polypeptide corresponding to positions 104-106 of SEQ ID NO: 2 are not identical to N-X-S or N-X-T.

3. The purified or isolated, soluble, ligand binding polypeptide according to claim 1, comprising an amino acid sequence having at least 95% identity to the sequence of amino acids defined by positions 47-314 of SEQ ID NO: 2, with the proviso that positions of the polypeptide corresponding to positions 104-106 of SEQ ID NO: 2 are not identical to N-X-S or N-X-T.

4. The purified or isolated, soluble, ligand binding polypeptide according to claim 1, comprising an amino acid sequence having at least 95% identity to the sequence of amino acids defined by positions 25-314 of SEQ ID NO: 2, with the proviso that positions of the polypeptide corresponding to positions 104-106 of SEQ ID NO: 2 are not identical to N-X-S or N-X-T.

5. The purified or isolated, soluble, ligand binding polypeptide according to claim 4 that retains four N-glycosylation sequon sites corresponding to positions 33-35 of SEQ ID NO: 2, positions 166-168 of SEQ ID NO: 2, positions 251-253 of SEQ ID NO: 2, and positions 299-301 of SEQ ID NO: 2.

6. The purified or isolated, soluble, ligand binding polypeptide according to claim 5, that is glycosylated at said four N-glycosylation sequon sites.

7. The purified or isolated, soluble, ligand binding polypeptide according to claim 4 that binds human VEGF-C with a $K_d$ or 1 nM or less.

8. The purified or isolated, soluble, ligand binding polypeptide according to claim 4, that binds human VEGF-D with a $K_d$ of 5 nM or less.

9. The purified or isolated, soluble, ligand binding polypeptide according to claim 4, wherein the amino acid in the polypeptide corresponding to position 104 of SEQ ID NO: 2 is deleted or replaced with another amino acid.

10. The purified or isolated, soluble, ligand binding polypeptide according to claim 4, wherein the amino acid corresponding to position 104 of SEQ ID NO: 2 is deleted or replaced with another amino acid selected from the group consisting of glutamine, aspartate, glutamate, arginine, and lysine.

11. The purified or isolated, soluble, ligand binding polypeptide according to claim 4, further comprising a signal peptide.

12. The purified or isolated, soluble, ligand binding polypeptide according to claim 4, further comprising at least one polyethylene glycol moiety attached to the polypeptide.

13. The purified or isolated, soluble, ligand binding polypeptide according to claim 12, comprising polyethylene glycol of about 20-40 kDa attached to the amino terminus of the polypeptide.

14. A soluble, ligand binding molecule comprising the soluble, ligand binding polypeptide according to claim 4 connected to a heterologous peptide.

15. The soluble, ligand binding molecule according to claim 14, wherein the heterologous peptide comprises an immunoglobulin constant domain fragment.

16. The soluble, ligand binding molecule according to claim 15, wherein the immunoglobulin constant fragment comprises amino acids 306-537 of SEQ ID NO: 3.

17. The soluble, ligand binding molecule according to claim 15, wherein the immunoglobulin constant domain fragment is an IgG constant domain fragment.

18. The soluble, ligand binding molecule according to claim 14, optionally comprising a linker connecting the heterologous peptide to the soluble, ligand binding polypeptide.

19. The soluble, ligand binding molecule according to claim 14 that comprises a polypeptide in which a C-terminal amino acid of the soluble, ligand binding polypeptide is directly attached to an N-terminal amino acid of the heterologous peptide by a peptide bond.

20. The soluble, ligand binding molecule according to claim 14, further comprising a signal peptide that directs secretion of the molecule from a cell that expresses the molecule.

21. The soluble, ligand binding molecule according to claim 14, wherein the molecule comprises the amino acid sequence set forth in SEQ ID NO: 3.

22. The soluble, ligand binding molecule according to claim 14, wherein the ligand binding polypeptide and the heterologous peptide are linked by amide bonding to form a single polypeptide chain.

23. The soluble, ligand binding molecule according to claim 14 further comprising a detectable label.

24. A conjugate comprising the soluble, ligand binding molecule according to claim 14 and a chemotherapeutic agent.

25. The soluble, ligand binding polypeptide according to claim 4 further comprising a detectable label.

26. A conjugate comprising the soluble, ligand binding polypeptide according to claim 4 and a chemotherapeutic agent.

27. A composition comprising a purified or isolated, soluble, ligand binding polypeptide or ligand binding molecule according to claim 4 and a pharmaceutically acceptable diluent, adjuvant, excipient, or carrier.

28. The composition according to claim 27, that is formulated for topical administration.

29. The composition according to claim 28, that is in the form of a solid, a paste, an ointment, a gel, a liquid, an aerosol, a mist, a polymer, a film, an emulsion, or a suspension.

30. The composition according to claim 27, that is formulated for intravitreal administration.

31. A method of inhibiting neovascularization in a subject, the method comprising administering to the subject a composition according to claim 27 in an amount effective to inhibit neovascularization in the subject.

32. The method according to claim 31, wherein the subject has been diagnosed with a tumor, and wherein the composition is administered in an amount effective to inhibit neovascularization in the tumor.

33. The method according to claim 32, wherein the composition is administered locally to the tumor or to the organ or tissue from which the tumor has been surgically removed.

34. The method according to claim 32, wherein the composition is administered in an amount effective to inhibit VEGF-C and/or VEGF-D in the tumor of the subject from binding to or stimulating VEGFR-2 and/or VEGFR-3 expressed in tumor cells.

35. A method of inhibiting choroidal or retinal neovascularization in a subject, the method comprising administering to the subject a composition according to claim 27, in an amount effective to inhibit retinal neovascularization in the subject.

36. The method according to claim 35, wherein the composition is administered locally to the eye of the subject.

37. The method according to claim 36, wherein the composition is administered by intravitreal injection.

38. The method according to claim 36, wherein the composition is administered by intravitreal implant.

39. The method according to claim 36, wherein the composition is administered by topical administration.

40. The method according to claim 35, wherein the composition is administered in an amount effective to inhibit VEGF-C and/or VEGF-D in the eye of the subject from binding to or stimulating VEGFR-2 and/or VEGFR-3 expressed in cells of the eye or vessels of the eye.

41. The method according to claim 35, further comprising administering an antibiotic to the subject.

42. The method according to claim 41, wherein the antibiotic is selected from the group consisting of amikacin, gentamicin, kanamycin, neomycin, netilmicin, streptomycin, tobramycin, teicoplanin, vancomycin, azithromycin, clarithromycin, dirithromycin, erythromycin, roxithromycin, troleandomycin, amoxicillin, ampicillin, azlocillin, carbenicillin, clozacillin, dicloxacillin, flucoxacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, sulfacetamide, sulfamethizole, sulfasalazine, sulfisoxazole, trimethoprim, cotrimoxazole, demeclocycline, soxycycline, minocycline, oxytetracycline, and tetracycline.

43. A method of treating a subject having an ocular disorder associated with retinal neovascularization, the method comprising administering to the subject a composition according to claim 27, in an amount effective to inhibit retinal neovascularization in the subject.

44. The method of claim 43, wherein the ocular disorder is selected from the group consisting of macular degeneration, diabetic retinopathy and macular telangiectasia.

45. The purified or isolated, soluble, ligand binding polypeptide according to claim 1, comprising an amino acid sequence that is identical to the sequence of amino acids defined by positions 47-115 of SEQ ID NO: 2, positions 47-210 of SEQ ID NO: 2, positions 47-314 of SEQ ID NO: 2, or positions 47-752 of SEQ ID NO: 2, with the proviso that positions of the polypeptide corresponding to positions 104-106 of SEQ ID NO: 2 are not identical to N-X-S or N-X-T.

46. The purified or isolated, soluble, ligand polypeptide according to claim 1, wherein the polypeptide comprises amino acids 23-290 of SEQ ID NO: 3.

47. The purified or isolated, soluble, ligand binding polypeptide according to claim 1, comprising an amino acid sequence having at least 95% identity to the sequence of amino acids defined by positions 25-752 of SEQ ID NO: 2, with the proviso that positions of the polypeptide corresponding to positions 104-106 of SEQ ID NO: 2 are not identical to N-X-S or N-X-T.

48. A purified or isolated, ligand binding polypeptide comprising an amino acid sequence having at least 95% identity to the sequence of amino acids defined by positions 25-314 of SEQ ID NO: 2, with the proviso that positions of the polypeptide corresponding to positions 104-106 of SEQ ID NO: 2 are not identical to N-X-S or N-X-T,
- wherein the polypeptide lacks VEGFR-3 Ig-like domains 4-7, lacks a VEGFR-3 transmembrane domain, and lacks a VEGFR-3 intracellular domain, and
- wherein the polypeptide binds human VEGF-C or human VEGF-D.

49. A purified or isolated, soluble, ligand binding polypeptide comprising an amino acid sequence having at least 95% identity to the sequence of amino acids defined by positions 25-314 of SEQ ID NO: 2, with the proviso that positions of the polypeptide corresponding to positions 104-106 of SEQ ID NO: 2 are not identical to N-X-S or N-X-T,
- wherein the polypeptide binds human VEGF-C or human VEGF-D and inhibits VEGF-C- or VEGF-D-binding to VEGFR-3 or inhibits VEGF-C- or VEGF-D-mediated stimulation of VEGFR-3 in a cell expressing VEGFR-3 on its surface.

* * * * *

SEQUENCE LISTING

<160> NUMBER OF SEQ ID NOS: 21

<210> SEQ ID NO 1
<211> LENGTH: 4195
<212> TYPE: DNA
<213> ORGANISM: Homo sapiens
<220> FEATURE:
<221> NAME/KEY: CDS
<222> LOCATION: (20)..(3913)

<400> SEQUENCE: 1

```
ccacgcgcag cggccggag atg cag cgg ggc gcc gcg ctg tgc ctg cga ctg      52
                     Met Gln Arg Gly Ala Ala Leu Cys Leu Arg Leu
                      1               5                  10 tgg ctc tgc ctg gga ctc ctg gac ggc ctg gtg agt ggc tac tcc atg       100
Trp Leu Cys Leu Gly Leu Leu Asp Gly Leu Val Ser Gly Tyr Ser Met
        15                  20                  25 acc ccc ccg acc ttg aac atc acg gag gag tca cac gtc atc gac acc       148
Thr Pro Pro Thr Leu Asn Ile Thr Glu Glu Ser His Val Ile Asp Thr
    30                  35                  40 ggt gac agc ctg tcc atc tcc tgc agg gga cag cac ccc ctc gag tgg       196
Gly Asp Ser Leu Ser Ile Ser Cys Arg Gly Gln His Pro Leu Glu Trp
45                  50                  55 gct tgg cca gga gct cag gag gcg cca gcc acc gga gac aag gac agc       244
Ala Trp Pro Gly Ala Gln Glu Ala Pro Ala Thr Gly Asp Lys Asp Ser
60                  65                  70                  75 gag gac acg ggg gtg gtg cga gac tgc gag ggc aca gac gcc agg ccc       292
Glu Asp Thr Gly Val Val Arg Asp Cys Glu Gly Thr Asp Ala Arg Pro
                80                  85                  90 tac tgc aag gtg ttg ctg ctg cac gag gta cat gcc aac gac aca ggc       340
Tyr Cys Lys Val Leu Leu Leu His Glu Val His Ala Asn Asp Thr Gly
        95                  100                 105 agc tac gtc tgc tac tac aag tac atc aag gca cgc atc gag ggc acc       388
Ser Tyr Val Cys Tyr Tyr Lys Tyr Ile Lys Ala Arg Ile Glu Gly Thr
    110                 115                 120 acg gcc gcc agc tcc tac gtg ttc gtg aga gac ttt gag cag cca ttc       436
Thr Ala Ala Ser Ser Tyr Val Phe Val Arg Asp Phe Glu Gln Pro Phe
125                 130                 135 atc aac aag cct gac acg ctc ttg gtc aac agg aag gac gcc atg tgg       484
Ile Asn Lys Pro Asp Thr Leu Leu Val Asn Arg Lys Asp Ala Met Trp
140                 145                 150                 155 gtg ccc tgt ctg gtg tcc atc ccc ggc ctc aat gtc acg ctg cgc tcg       532
Val Pro Cys Leu Val Ser Ile Pro Gly Leu Asn Val Thr Leu Arg Ser
                160                 165                 170 caa agc tcg gtg ctg tgg cca gac ggg cag gag gtg gtg tgg gat gac       580
Gln Ser Ser Val Leu Trp Pro Asp Gly Gln Glu Val Val Trp Asp Asp
        175                 180                 185 cgg cgg ggc atg ctc gtg tcc acg cca ctg ctg cac gat gcc ctg tac       628
Arg Arg Gly Met Leu Val Ser Thr Pro Leu Leu His Asp Ala Leu Tyr
    190                 195                 200 ctg cag tgc gag acc acc tgg gga gac cag gac ttc ctt tcc aac ccc       676
Leu Gln Cys Glu Thr Thr Trp Gly Asp Gln Asp Phe Leu Ser Asn Pro
205                 210                 215 ttc ctg gtg cac atc aca ggc aac gag ctc tat gac atc cag ctg ttg       724
Phe Leu Val His Ile Thr Gly Asn Glu Leu Tyr Asp Ile Gln Leu Leu
220                 225                 230                 235
```

|   |   |   |   |   |   |   |   |   |   |   |   |   |   |   |   |     |
|---|---|---|---|---|---|---|---|---|---|---|---|---|---|---|---|-----|
| ccc | agg | aag | tcg | ctg | gag | ctg | ctg | gta | ggg | gag | aag | ctg | gtc | ctg | aac | 772 |
| Pro | Arg | Lys | Ser | Leu | Glu | Leu | Leu | Val | Gly | Glu | Lys | Leu | Val | Leu | Asn |     |
|     |     |     |     | 240 |     |     |     | 245 |     |     |     | 250 |     |     |     |     |

|   |   |   |   |   |   |   |   |   |   |   |   |   |   |   |   |     |
|---|---|---|---|---|---|---|---|---|---|---|---|---|---|---|---|-----|
| tgc | acc | gtg | tgg | gct | gag | ttt | aac | tca | ggt | gtc | acc | ttt | gac | tgg | gac | 820 |
| Cys | Thr | Val | Trp | Ala | Glu | Phe | Asn | Ser | Gly | Val | Thr | Phe | Asp | Trp | Asp |     |
|     |     |     | 255 |     |     |     |     | 260 |     |     |     |     | 265 |     |     |     |

|   |   |   |   |   |   |   |   |   |   |   |   |   |   |   |   |     |
|---|---|---|---|---|---|---|---|---|---|---|---|---|---|---|---|-----|
| tac | cca | ggg | aag | cag | gca | gag | cgg | ggt | aag | tgg | gtg | ccc | gag | cga | cgc | 868 |
| Tyr | Pro | Gly | Lys | Gln | Ala | Glu | Arg | Gly | Lys | Trp | Val | Pro | Glu | Arg | Arg |     |
|     |     | 270 |     |     |     |     | 275 |     |     |     |     | 280 |     |     |     |     |

|   |   |   |   |   |   |   |   |   |   |   |   |   |   |   |   |     |
|---|---|---|---|---|---|---|---|---|---|---|---|---|---|---|---|-----|
| tcc | cag | cag | acc | cac | aca | gaa | ctc | tcc | agc | atc | ctg | acc | atc | cac | aac | 916 |
| Ser | Gln | Gln | Thr | His | Thr | Glu | Leu | Ser | Ser | Ile | Leu | Thr | Ile | His | Asn |     |
|     | 285 |     |     |     |     | 290 |     |     |     |     | 295 |     |     |     |     |     |

|   |   |   |   |   |   |   |   |   |   |   |   |   |   |   |   |     |
|---|---|---|---|---|---|---|---|---|---|---|---|---|---|---|---|-----|
| gtc | agc | cag | cac | gac | ctg | ggc | tcg | tat | gtg | tgc | aag | gcc | aac | aac | ggc | 964 |
| Val | Ser | Gln | His | Asp | Leu | Gly | Ser | Tyr | Val | Cys | Lys | Ala | Asn | Asn | Gly |     |
| 300 |     |     |     |     | 305 |     |     |     |     | 310 |     |     |     |     | 315 |     |

|   |   |   |   |   |   |   |   |   |   |   |   |   |   |   |   |      |
|---|---|---|---|---|---|---|---|---|---|---|---|---|---|---|---|------|
| atc | cag | cga | ttt | cgg | gag | agc | acc | gag | gtc | att | gtg | cat | gaa | aat | ccc | 1012 |
| Ile | Gln | Arg | Phe | Arg | Glu | Ser | Thr | Glu | Val | Ile | Val | His | Glu | Asn | Pro |      |
|     |     |     | 320 |     |     |     |     | 325 |     |     |     |     | 330 |     |     |      |

|   |   |   |   |   |   |   |   |   |   |   |   |   |   |   |   |      |
|---|---|---|---|---|---|---|---|---|---|---|---|---|---|---|---|------|
| ttc | atc | agc | gtc | gag | tgg | ctc | aaa | gga | ccc | atc | ctg | gag | gcc | acg | gca | 1060 |
| Phe | Ile | Ser | Val | Glu | Trp | Leu | Lys | Gly | Pro | Ile | Leu | Glu | Ala | Thr | Ala |      |
|     |     | 335 |     |     |     |     | 340 |     |     |     |     | 345 |     |     |     |      |

|   |   |   |   |   |   |   |   |   |   |   |   |   |   |   |   |      |
|---|---|---|---|---|---|---|---|---|---|---|---|---|---|---|---|------|
| gga | gac | gag | ctg | gtg | aag | ctg | ccc | gtg | aag | ctg | gca | gcg | tac | ccc | ccg | 1108 |
| Gly | Asp | Glu | Leu | Val | Lys | Leu | Pro | Val | Lys | Leu | Ala | Ala | Tyr | Pro | Pro |      |
|     |     | 350 |     |     |     |     | 355 |     |     |     |     | 360 |     |     |     |      |

|   |   |   |   |   |   |   |   |   |   |   |   |   |   |   |   |      |
|---|---|---|---|---|---|---|---|---|---|---|---|---|---|---|---|------|
| ccc | gag | ttc | cag | tgg | tac | aag | gat | gga | aag | gca | ctg | tcc | ggg | cgc | cac | 1156 |
| Pro | Glu | Phe | Gln | Trp | Tyr | Lys | Asp | Gly | Lys | Ala | Leu | Ser | Gly | Arg | His |      |
| 365 |     |     |     |     | 370 |     |     |     |     | 375 |     |     |     |     |     |      |

|   |   |   |   |   |   |   |   |   |   |   |   |   |   |   |   |      |
|---|---|---|---|---|---|---|---|---|---|---|---|---|---|---|---|------|
| agt | cca | cat | gcc | ctg | gtg | ctc | aag | gag | gtg | aca | gag | gcc | agc | aca | ggc | 1204 |
| Ser | Pro | His | Ala | Leu | Val | Leu | Lys | Glu | Val | Thr | Glu | Ala | Ser | Thr | Gly |      |
| 380 |     |     |     |     | 385 |     |     |     |     | 390 |     |     |     |     | 395 |      |

|   |   |   |   |   |   |   |   |   |   |   |   |   |   |   |   |      |
|---|---|---|---|---|---|---|---|---|---|---|---|---|---|---|---|------|
| acc | tac | acc | ctc | gcc | ctg | tgg | aac | tcc | gct | gct | ggc | ctg | agg | cgc | aac | 1252 |
| Thr | Tyr | Thr | Leu | Ala | Leu | Trp | Asn | Ser | Ala | Ala | Gly | Leu | Arg | Arg | Asn |      |
|     |     |     | 400 |     |     |     |     | 405 |     |     |     |     | 410 |     |     |      |

|   |   |   |   |   |   |   |   |   |   |   |   |   |   |   |   |      |
|---|---|---|---|---|---|---|---|---|---|---|---|---|---|---|---|------|
| atc | agc | ctg | gag | ctg | gtg | gtg | aat | gtg | ccc | ccc | cag | ata | cat | gag | aag | 1300 |
| Ile | Ser | Leu | Glu | Leu | Val | Val | Asn | Val | Pro | Pro | Gln | Ile | His | Glu | Lys |      |
|     |     | 415 |     |     |     |     | 420 |     |     |     |     | 425 |     |     |     |      |

|   |   |   |   |   |   |   |   |   |   |   |   |   |   |   |   |      |
|---|---|---|---|---|---|---|---|---|---|---|---|---|---|---|---|------|
| gag | gcc | tcc | tcc | ccc | agc | atc | tac | tcg | cgt | cac | agc | cgc | cag | gcc | ctc | 1348 |
| Glu | Ala | Ser | Ser | Pro | Ser | Ile | Tyr | Ser | Arg | His | Ser | Arg | Gln | Ala | Leu |      |
|     |     | 430 |     |     |     |     | 435 |     |     |     |     | 440 |     |     |     |      |

|   |   |   |   |   |   |   |   |   |   |   |   |   |   |   |   |      |
|---|---|---|---|---|---|---|---|---|---|---|---|---|---|---|---|------|
| acc | tgc | acg | gcc | tac | ggg | gtg | ccc | ctg | cct | ctc | agc | atc | cag | tgg | cac | 1396 |
| Thr | Cys | Thr | Ala | Tyr | Gly | Val | Pro | Leu | Pro | Leu | Ser | Ile | Gln | Trp | His |      |
|     | 445 |     |     |     |     | 450 |     |     |     |     | 455 |     |     |     |     |      |

|   |   |   |   |   |   |   |   |   |   |   |   |   |   |   |   |      |
|---|---|---|---|---|---|---|---|---|---|---|---|---|---|---|---|------|
| tgg | cgg | ccc | tgg | aca | ccc | tgc | aag | atg | ttt | gcc | cag | cgt | agt | ctc | cgg | 1444 |
| Trp | Arg | Pro | Trp | Thr | Pro | Cys | Lys | Met | Phe | Ala | Gln | Arg | Ser | Leu | Arg |      |
| 460 |     |     |     |     | 465 |     |     |     |     | 470 |     |     |     |     | 475 |      |

|   |   |   |   |   |   |   |   |   |   |   |   |   |   |   |   |      |
|---|---|---|---|---|---|---|---|---|---|---|---|---|---|---|---|------|
| cgg | cgg | cag | cag | caa | gac | ctc | atg | cca | cag | tgc | cgt | gac | tgg | agg | gcg | 1492 |
| Arg | Arg | Gln | Gln | Gln | Asp | Leu | Met | Pro | Gln | Cys | Arg | Asp | Trp | Arg | Ala |      |
|     |     |     | 480 |     |     |     |     | 485 |     |     |     |     | 490 |     |     |      |

|   |   |   |   |   |   |   |   |   |   |   |   |   |   |   |   |      |
|---|---|---|---|---|---|---|---|---|---|---|---|---|---|---|---|------|
| gtg | acc | acg | cag | gat | gcc | gtg | aac | ccc | atc | gag | agc | ctg | gac | acc | tgg | 1540 |
| Val | Thr | Thr | Gln | Asp | Ala | Val | Asn | Pro | Ile | Glu | Ser | Leu | Asp | Thr | Trp |      |
|     |     |     | 495 |     |     |     |     | 500 |     |     |     |     | 505 |     |     |      |

|   |   |   |   |   |   |   |   |   |   |   |   |   |   |   |   |      |
|---|---|---|---|---|---|---|---|---|---|---|---|---|---|---|---|------|
| acc | gag | ttt | gtg | gag | gga | aag | aat | aag | act | gtg | agc | aag | ctg | gtg | atc | 1588 |
| Thr | Glu | Phe | Val | Glu | Gly | Lys | Asn | Lys | Thr | Val | Ser | Lys | Leu | Val | Ile |      |
|     |     |     | 510 |     |     |     |     | 515 |     |     |     |     | 520 |     |     |      |

|   |   |   |   |   |   |   |   |   |   |   |   |   |   |   |   |      |
|---|---|---|---|---|---|---|---|---|---|---|---|---|---|---|---|------|
| cag | aat | gcc | aac | gtg | tct | gcc | atg | tac | aag | tgt | gtg | gtc | tcc | aac | aag | 1636 |
| Gln | Asn | Ala | Asn | Val | Ser | Ala | Met | Tyr | Lys | Cys | Val | Val | Ser | Asn | Lys |      |
|     | 525 |     |     |     |     | 530 |     |     |     |     | 535 |     |     |     |     |      |

|   |   |   |   |   |   |   |   |   |   |   |   |   |   |   |   |      |
|---|---|---|---|---|---|---|---|---|---|---|---|---|---|---|---|------|
| gtg | ggc | cag | gat | gag | cgg | ctc | atc | tac | ttc | tat | gtg | acc | acc | atc | ccc | 1684 |
| Val | Gly | Gln | Asp | Glu | Arg | Leu | Ile | Tyr | Phe | Tyr | Val | Thr | Thr | Ile | Pro |      |
| 540 |     |     |     |     | 545 |     |     |     |     | 550 |     |     |     |     | 555 |      |

```
gac ggc ttc acc atc gaa tcc aag cca tcc gag gag cta cta gag ggc    1732
Asp Gly Phe Thr Ile Glu Ser Lys Pro Ser Glu Glu Leu Leu Glu Gly
                560                 565                 570 cag ccg gtg ctc ctg agc tgc caa gcc gac agc tac aag tac gag cat    1780
Gln Pro Val Leu Leu Ser Cys Gln Ala Asp Ser Tyr Lys Tyr Glu His
        575                 580                 585 ctg cgc tgg tac cgc ctc aac ctg tcc acg ctg cac gat gcg cac ggg    1828
Leu Arg Trp Tyr Arg Leu Asn Leu Ser Thr Leu His Asp Ala His Gly
            590                 595                 600 aac ccg ctt ctg ctc gac tgc aag aac gtg cat ctg ttc gcc acc cct    1876
Asn Pro Leu Leu Leu Asp Cys Lys Asn Val His Leu Phe Ala Thr Pro
605                 610                 615 ctg gcc gcc agc ctg gag gag gtg gca cct ggg gcg cgc cac gcc acg    1924
Leu Ala Ala Ser Leu Glu Glu Val Ala Pro Gly Ala Arg His Ala Thr
620                 625                 630                 635 ctc agc ctg agt atc ccc cgc gtc gcg ccc gag cac gag ggc cac tat    1972
Leu Ser Leu Ser Ile Pro Arg Val Ala Pro Glu His Glu Gly His Tyr
                640                 645                 650 gtg tgc gaa gtg caa gac cgg cgc agc cat gac aag cac tgc cac aag    2020
Val Cys Glu Val Gln Asp Arg Arg Ser His Asp Lys His Cys His Lys
            655                 660                 665 aag tac ctg tcg gtg cag gcc ctg gaa gcc cct cgg ctc acg cag aac    2068
Lys Tyr Leu Ser Val Gln Ala Leu Glu Ala Pro Arg Leu Thr Gln Asn
        670                 675                 680 ttg acc gac ctc ctg gtg aac gtg agc gac tcg ctg gag atg cag tgc    2116
Leu Thr Asp Leu Leu Val Asn Val Ser Asp Ser Leu Glu Met Gln Cys
685                 690                 695 ttg gtg gcc gga gcg cac gcg ccc agc atc gtg tgg tac aaa gac gag    2164
Leu Val Ala Gly Ala His Ala Pro Ser Ile Val Trp Tyr Lys Asp Glu
700                 705                 710                 715 agg ctg ctg gag gaa aag tct gga gtc gac ttg gcg gac tcc aac cag    2212
Arg Leu Leu Glu Glu Lys Ser Gly Val Asp Leu Ala Asp Ser Asn Gln
                720                 725                 730 aag ctg agc atc cag cgc gtg cgc gag gag gat gcg gga cgc tat ctg    2260
Lys Leu Ser Ile Gln Arg Val Arg Glu Glu Asp Ala Gly Arg Tyr Leu
            735                 740                 745 tgc agc gtg tgc aac gcc aag ggc tgc gtc aac tcc tcc gcc agc gtg    2308
Cys Ser Val Cys Asn Ala Lys Gly Cys Val Asn Ser Ser Ala Ser Val
        750                 755                 760 gcc gtg gaa ggc tcc gag gat aag ggc agc atg gag atc gtg atc ctt    2356
Ala Val Glu Gly Ser Glu Asp Lys Gly Ser Met Glu Ile Val Ile Leu
765                 770                 775 gtc ggt acc ggc gtc atc gct gtc ttc ttc tgg gtc ctc ctc ctc        2404
Val Gly Thr Gly Val Ile Ala Val Phe Phe Trp Val Leu Leu Leu Leu
780                 785                 790                 795 atc ttc tgt aac atg agg agg ccg gcc cac gca gac atc aag acg ggc    2452
Ile Phe Cys Asn Met Arg Arg Pro Ala His Ala Asp Ile Lys Thr Gly
                800                 805                 810 tac ctg tcc atc atc atg gac ccc ggg gag gtg cct ctg gag gag caa    2500
Tyr Leu Ser Ile Ile Met Asp Pro Gly Glu Val Pro Leu Glu Glu Gln
            815                 820                 825 tgc gaa tac ctg tcc tac gat gcc agc cag tgg gaa ttc ccc cga gag    2548
Cys Glu Tyr Leu Ser Tyr Asp Ala Ser Gln Trp Glu Phe Pro Arg Glu
        830                 835                 840 cgg ctg cac ctg ggg aga gtg ctc ggc tac ggc gcc ttc ggg aag gtg    2596
Arg Leu His Leu Gly Arg Val Leu Gly Tyr Gly Ala Phe Gly Lys Val
845                 850                 855 gtg gaa gcc tcc gct ttc ggc atc cac aag ggc agc agc tgt gac acc    2644
Val Glu Ala Ser Ala Phe Gly Ile His Lys Gly Ser Ser Cys Asp Thr
```

-continued

| | | | |
|---|---|---|---|
| 860 | 865 | 870 | 875 | gtg gcc gtg aaa atg ctg aaa gag ggc gcc acg gcc agc gag cac cgc   2692
Val Ala Val Lys Met Leu Lys Glu Gly Ala Thr Ala Ser Glu His Arg
              880             885             890 gcg ctg atg tcg gag ctc aag atc ctc att cac atc ggc aac cac ctc   2740
Ala Leu Met Ser Glu Leu Lys Ile Leu Ile His Ile Gly Asn His Leu
              895             900             905 aac gtg gtc aac ctc ctc ggg gcg tgc acc aag ccg cag ggc ccc ctc   2788
Asn Val Val Asn Leu Leu Gly Ala Cys Thr Lys Pro Gln Gly Pro Leu
              910             915             920 atg gtg atc gtg gag ttc tgc aag tac ggc aac ctc tcc aac ttc ctg   2836
Met Val Ile Val Glu Phe Cys Lys Tyr Gly Asn Leu Ser Asn Phe Leu
              925             930             935 cgc gcc aag cgg gac gcc ttc agc ccc tgc gcg gag aag tct ccc gag   2884
Arg Ala Lys Arg Asp Ala Phe Ser Pro Cys Ala Glu Lys Ser Pro Glu
940             945             950             955 cag cgc gga cgc ttc cgc gcc atg gtg gag ctc gcc agg ctg gat cgg   2932
Gln Arg Gly Arg Phe Arg Ala Met Val Glu Leu Ala Arg Leu Asp Arg
              960             965             970 agg cgg ccg ggg agc agc gac agg gtc ctc ttc gcg cgg ttc tcg aag   2980
Arg Arg Pro Gly Ser Ser Asp Arg Val Leu Phe Ala Arg Phe Ser Lys
              975             980             985 acc gag ggc gga gcg agg cgg gct tct cca gac caa gaa gct gag gac   3028
Thr Glu Gly Gly Ala Arg Arg Ala Ser Pro Asp Gln Glu Ala Glu Asp
              990             995             1000 ctg tgg ctg agc ccg ctg acc atg gaa gat ctt gtc tgc tac agc   3073
Leu Trp Leu Ser Pro Leu Thr Met Glu Asp Leu Val Cys Tyr Ser
     1005             1010             1015 ttc cag gtg gcc aga ggg atg gag ttc ctg gct tcc cga aag tgc   3118
Phe Gln Val Ala Arg Gly Met Glu Phe Leu Ala Ser Arg Lys Cys
     1020             1025             1030 atc cac aga gac ctg gct gct cgg aac att ctg ctg tcg gaa agc   3163
Ile His Arg Asp Leu Ala Ala Arg Asn Ile Leu Leu Ser Glu Ser
     1035             1040             1045 gac gtg gtg aag atc tgt gac ttt ggc ctt gcc cgg gac atc tac   3208
Asp Val Val Lys Ile Cys Asp Phe Gly Leu Ala Arg Asp Ile Tyr
     1050             1055             1060 aaa gac cct gac tac gtc cgc aag ggc agt gcc cgg ctg ccc ctg   3253
Lys Asp Pro Asp Tyr Val Arg Lys Gly Ser Ala Arg Leu Pro Leu
     1065             1070             1075 aag tgg atg gcc cct gaa agc atc ttc gac aag gtg tac acc acg   3298
Lys Trp Met Ala Pro Glu Ser Ile Phe Asp Lys Val Tyr Thr Thr
     1080             1085             1090 cag agt gac gtg tgg tcc ttt ggg gtg ctt ctc tgg gag atc ttc   3343
Gln Ser Asp Val Trp Ser Phe Gly Val Leu Leu Trp Glu Ile Phe
     1095             1100             1105 tct ctg ggg gcc tcc ccg tac cct ggg gtg cag atc aat gag gag   3388
Ser Leu Gly Ala Ser Pro Tyr Pro Gly Val Gln Ile Asn Glu Glu
     1110             1115             1120 ttc tgc cag cgg ctg aga gac ggc aca agg atg agg gcc ccg gag   3433
Phe Cys Gln Arg Leu Arg Asp Gly Thr Arg Met Arg Ala Pro Glu
     1125             1130             1135 ctg gcc act ccc gcc ata cgc cgc atc atg ctg aac tgc tgg tcc   3478
Leu Ala Thr Pro Ala Ile Arg Arg Ile Met Leu Asn Cys Trp Ser
     1140             1145             1150 gga gac ccc aag gcg aga cct gca ttc tcg gag ctg gtg gag atc   3523
Gly Asp Pro Lys Ala Arg Pro Ala Phe Ser Glu Leu Val Glu Ile
     1155             1160             1165 ctg ggg gac ctg ctc cag ggc agg ggc ctg caa gag gaa gag gag   3568
Leu Gly Asp Leu Leu Gln Gly Arg Gly Leu Gln Glu Glu Glu Glu -continued

| | | | | | | | | | | | | | | |
|---|---|---|---|---|---|---|---|---|---|---|---|---|---|---|
| Leu | Gly | Asp | Leu | Leu | Gln | Gly | Arg | Gly | Leu | Gln | Glu | Glu | Glu | Glu |
| | 1170 | | | | 1175 | | | | | 1180 | | | | |

```
gtc tgc atg gcc ccg cgc agc tct cag agc tca gaa gag ggc agc    3613
Val Cys Met Ala Pro Arg Ser Ser Gln Ser Ser Glu Glu Gly Ser
1185                1190                1195 ttc tcg cag gtg tcc acc atg gcc cta cac atc gcc cag gct gac    3658
Phe Ser Gln Val Ser Thr Met Ala Leu His Ile Ala Gln Ala Asp
1200                1205                1210 gct gag gac agc ccg cca agc ctg cag cgc cac agc ctg gcc gcc    3703
Ala Glu Asp Ser Pro Pro Ser Leu Gln Arg His Ser Leu Ala Ala
1215                1220                1225 agg tat tac aac tgg gtg tcc ttt ccc ggg tgc ctg gcc aga ggg    3748
Arg Tyr Tyr Asn Trp Val Ser Phe Pro Gly Cys Leu Ala Arg Gly
1230                1235                1240 gct gag acc cgt ggt tcc tcc agg atg aag aca ttt gag gaa ttc    3793
Ala Glu Thr Arg Gly Ser Ser Arg Met Lys Thr Phe Glu Glu Phe
1245                1250                1255 ccc atg acc cca acg acc tac aaa ggc tct gtg gac aac cag aca    3838
Pro Met Thr Pro Thr Thr Tyr Lys Gly Ser Val Asp Asn Gln Thr
1260                1265                1270 gac agt ggg atg gtg ctg gcc tcg gag gag ttt gag cag ata gag    3883
Asp Ser Gly Met Val Leu Ala Ser Glu Glu Phe Glu Gln Ile Glu
1275                1280                1285 agc agg cat aga caa gaa agc ggc ttc agg tagctgaagc agagagagag  3933
Ser Arg His Arg Gln Glu Ser Gly Phe Arg
1290                1295 aaggcagcat acgtcagcat tttcttctct gcacttataa gaaagatcaa agactttaag    3993
actttcgcta tttcttctac tgctatctac tacaaacttc aaagaggaac caggaggaca    4053
agaggagcat gaaagtggac aaggagtgtg accactgaag caccacaggg aaggggttag    4113
gcctccggat gactgcgggc aggcctggat aatatccagc ctcccacaag aagctggtgg    4173
agcagagtgt tccctgactc ct    4195

<210> SEQ ID NO 2
<211> LENGTH: 1298
<212> TYPE: PRT
<213> ORGANISM: Homo sapiens

<400> SEQUENCE: 2

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
                20                  25                  30

Asn Ile Thr Glu Glu Ser His Val Ile Asp Thr Gly Asp Ser Leu Ser
            35                  40                  45

Ile Ser Cys Arg Gly Gln His Pro Leu Glu Trp Ala Trp Pro Gly Ala
        50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140
```

-continued

```
Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
            165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
            195                 200                 205

Thr Trp Gly Asp Gln Asp Phe Leu Ser Asn Pro Phe Leu Val His Ile
210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
            245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
            275                 280                 285

Thr Glu Leu Ser Ser Ile Leu Thr Ile His Asn Val Ser Gln His Asp
290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
            325                 330                 335

Trp Leu Lys Gly Pro Ile Leu Glu Ala Thr Ala Gly Asp Glu Leu Val
            340                 345                 350

Lys Leu Pro Val Lys Leu Ala Ala Tyr Pro Pro Pro Glu Phe Gln Trp
            355                 360                 365

Tyr Lys Asp Gly Lys Ala Leu Ser Gly Arg His Ser Pro His Ala Leu
370                 375                 380

Val Leu Lys Glu Val Thr Glu Ala Ser Thr Gly Thr Tyr Thr Leu Ala
385                 390                 395                 400

Leu Trp Asn Ser Ala Ala Gly Leu Arg Arg Asn Ile Ser Leu Glu Leu
            405                 410                 415

Val Val Asn Val Pro Pro Gln Ile His Glu Lys Glu Ala Ser Ser Pro
            420                 425                 430

Ser Ile Tyr Ser Arg His Ser Arg Gln Ala Leu Thr Cys Thr Ala Tyr
            435                 440                 445

Gly Val Pro Leu Pro Leu Ser Ile Gln Trp His Trp Arg Pro Trp Thr
            450                 455                 460

Pro Cys Lys Met Phe Ala Gln Arg Ser Leu Arg Arg Arg Gln Gln Gln
465                 470                 475                 480

Asp Leu Met Pro Gln Cys Arg Asp Trp Arg Ala Val Thr Thr Gln Asp
            485                 490                 495

Ala Val Asn Pro Ile Glu Ser Leu Asp Thr Trp Thr Glu Phe Val Glu
            500                 505                 510

Gly Lys Asn Lys Thr Val Ser Lys Leu Val Ile Gln Asn Ala Asn Val
            515                 520                 525

Ser Ala Met Tyr Lys Cys Val Val Ser Asn Lys Val Gly Gln Asp Glu
            530                 535                 540

Arg Leu Ile Tyr Phe Tyr Val Thr Thr Ile Pro Asp Gly Phe Thr Ile
545                 550                 555                 560
```

-continued

```
Glu Ser Lys Pro Ser Glu Glu Leu Leu Glu Gly Gln Pro Val Leu Leu
                565                 570                 575

Ser Cys Gln Ala Asp Ser Tyr Lys Tyr Glu His Leu Arg Trp Tyr Arg
            580                 585                 590

Leu Asn Leu Ser Thr Leu His Asp Ala His Gly Asn Pro Leu Leu Leu
        595                 600                 605

Asp Cys Lys Asn Val His Leu Phe Ala Thr Pro Leu Ala Ala Ser Leu
    610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
                645                 650                 655

Asp Arg Arg Ser His Asp Lys His Cys His Lys Lys Tyr Leu Ser Val
            660                 665                 670

Gln Ala Leu Glu Ala Pro Arg Leu Thr Gln Asn Leu Thr Asp Leu Leu
        675                 680                 685

Val Asn Val Ser Asp Ser Leu Glu Met Gln Cys Leu Val Ala Gly Ala
    690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
                725                 730                 735

Arg Val Arg Glu Glu Asp Ala Gly Arg Tyr Leu Cys Ser Val Cys Asn
            740                 745                 750

Ala Lys Gly Cys Val Asn Ser Ser Ala Ser Val Ala Val Glu Gly Ser
        755                 760                 765

Glu Asp Lys Gly Ser Met Glu Ile Val Ile Leu Val Gly Thr Gly Val
    770                 775                 780

Ile Ala Val Phe Phe Trp Val Leu Leu Leu Leu Ile Phe Cys Asn Met
785                 790                 795                 800

Arg Arg Pro Ala His Ala Asp Ile Lys Thr Gly Tyr Leu Ser Ile Ile
                805                 810                 815

Met Asp Pro Gly Glu Val Pro Leu Glu Glu Gln Cys Glu Tyr Leu Ser
            820                 825                 830

Tyr Asp Ala Ser Gln Trp Glu Phe Pro Arg Glu Arg Leu His Leu Gly
        835                 840                 845

Arg Val Leu Gly Tyr Gly Ala Phe Gly Lys Val Val Glu Ala Ser Ala
    850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
                885                 890                 895

Leu Lys Ile Leu Ile His Ile Gly Asn His Leu Asn Val Val Asn Leu
            900                 905                 910

Leu Gly Ala Cys Thr Lys Pro Gln Gly Pro Leu Met Val Ile Val Glu
        915                 920                 925

Phe Cys Lys Tyr Gly Asn Leu Ser Asn Phe Leu Arg Ala Lys Arg Asp
    930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Arg Pro Gly Ser
                965                 970                 975

Ser Asp Arg Val Leu Phe Ala Arg Phe Ser Lys Thr Glu Gly Gly Ala
```

```
                980                985                990
Arg Arg Ala Ser Pro Asp Gln Glu  Ala Glu Asp Leu Trp  Leu Ser Pro
            995                1000               1005

Leu Thr Met Glu Asp Leu Val  Cys Tyr Ser Phe Gln  Val Ala Arg
    1010                1015               1020

Gly Met Glu Phe Leu Ala Ser  Arg Lys Cys Ile His  Arg Asp Leu
    1025                1030               1035

Ala Ala Arg Asn Ile Leu Leu  Ser Glu Ser Asp Val  Val Lys Ile
    1040                1045               1050

Cys Asp Phe Gly Leu Ala Arg  Asp Ile Tyr Lys Asp  Pro Asp Tyr
    1055                1060               1065

Val Arg Lys Gly Ser Ala Arg  Leu Pro Leu Lys Trp  Met Ala Pro
    1070                1075               1080

Glu Ser Ile Phe Asp Lys Val  Tyr Thr Thr Gln Ser  Asp Val Trp
    1085                1090               1095

Ser Phe Gly Val Leu Leu Trp  Glu Ile Phe Ser Leu  Gly Ala Ser
    1100                1105               1110

Pro Tyr Pro Gly Val Gln Ile  Asn Glu Glu Phe Cys  Gln Arg Leu
    1115                1120               1125

Arg Asp Gly Thr Arg Met Arg  Ala Pro Glu Leu Ala  Thr Pro Ala
    1130                1135               1140

Ile Arg Arg Ile Met Leu Asn  Cys Trp Ser Gly Asp  Pro Lys Ala
    1145                1150               1155

Arg Pro Ala Phe Ser Glu Leu  Val Glu Ile Leu Gly  Asp Leu Leu
    1160                1165               1170

Gln Gly Arg Gly Leu Gln Glu  Glu Glu Glu Val Cys  Met Ala Pro
    1175                1180               1185

Arg Ser Ser Gln Ser Ser Glu  Glu Gly Ser Phe Ser  Gln Val Ser
    1190                1195               1200

Thr Met Ala Leu His Ile Ala  Gln Ala Asp Ala Glu  Asp Ser Pro
    1205                1210               1215

Pro Ser Leu Gln Arg His Ser  Leu Ala Ala Arg Tyr  Tyr Asn Trp
    1220                1225               1230

Val Ser Phe Pro Gly Cys Leu  Ala Arg Gly Ala Glu  Thr Arg Gly
    1235                1240               1245

Ser Ser Arg Met Lys Thr Phe  Glu Glu Phe Pro Met  Thr Pro Thr
    1250                1255               1260

Thr Tyr Lys Gly Ser Val Asp  Asn Gln Thr Asp Ser  Gly Met Val
    1265                1270               1275

Leu Ala Ser Glu Glu Phe Glu  Gln Ile Glu Ser Arg  His Arg Gln
    1280                1285               1290

Glu Ser Gly Phe Arg
    1295

<210> SEQ ID NO 3
<211> LENGTH: 537
<212> TYPE: PRT
<213> ORGANISM: Homo sapiens

<400> SEQUENCE: 3

Tyr Ser Met Thr Pro Pro Thr Leu Asn Ile Thr Glu Glu Ser His Val
1               5                   10                  15

Ile Asp Thr Gly Asp Ser Leu Ser Ile Ser Cys Arg Gly Gln His Pro
            20                  25                  30
```

-continued

Leu Glu Trp Ala Trp Pro Gly Ala Gln Glu Ala Pro Ala Thr Gly Asp
         35                  40                  45
Lys Asp Ser Glu Asp Thr Gly Val Val Arg Asp Cys Glu Gly Thr Asp
 50                  55                  60
Ala Arg Pro Tyr Cys Lys Val Leu Leu Leu His Glu Val His Ala Gln
 65                  70                  75                  80
Asp Thr Gly Ser Tyr Val Cys Tyr Tyr Lys Tyr Ile Lys Ala Arg Ile
             85                  90                  95
Glu Gly Thr Thr Ala Ala Ser Ser Tyr Val Phe Val Arg Asp Phe Glu
            100                 105                 110
Gln Pro Phe Ile Asn Lys Pro Asp Thr Leu Leu Val Asn Arg Lys Asp
        115                 120                 125
Ala Met Trp Val Pro Cys Leu Val Ser Ile Pro Gly Leu Asn Val Thr
    130                 135                 140
Leu Arg Ser Gln Ser Ser Val Leu Trp Pro Asp Gly Gln Glu Val Val
145                 150                 155                 160
Trp Asp Asp Arg Arg Gly Met Leu Val Ser Thr Pro Leu Leu His Asp
                165                 170                 175
Ala Leu Tyr Leu Gln Cys Glu Thr Thr Trp Gly Asp Gln Asp Phe Leu
            180                 185                 190
Ser Asn Pro Phe Leu Val His Ile Thr Gly Asn Glu Leu Tyr Asp Ile
        195                 200                 205
Gln Leu Leu Pro Arg Lys Ser Leu Glu Leu Leu Val Gly Glu Lys Leu
    210                 215                 220
Val Leu Asn Cys Thr Val Trp Ala Glu Phe Asn Ser Gly Val Thr Phe
225                 230                 235                 240
Asp Trp Asp Tyr Pro Gly Lys Gln Ala Glu Arg Gly Lys Trp Val Pro
                245                 250                 255
Glu Arg Arg Ser Gln Gln Thr His Thr Glu Leu Ser Ser Ile Leu Thr
            260                 265                 270
Ile His Asn Val Ser Gln His Asp Leu Gly Ser Tyr Val Cys Lys Ala
        275                 280                 285
Asn Asn Gly Ile Gln Arg Phe Arg Glu Ser Thr Glu Val Ile Val His
    290                 295                 300
Glu Glu Pro Lys Ser Cys Asp Lys Thr His Thr Cys Pro Pro Cys Pro
305                 310                 315                 320
Ala Pro Glu Leu Leu Gly Gly Pro Ser Val Phe Leu Phe Pro Pro Lys
                325                 330                 335
Pro Lys Asp Thr Leu Met Ile Ser Arg Thr Pro Glu Val Thr Cys Val
            340                 345                 350
Val Val Asp Val Ser His Glu Asp Pro Glu Val Lys Phe Asn Trp Tyr
        355                 360                 365
Val Asp Gly Val Glu Val His Asn Ala Lys Thr Lys Pro Arg Glu Glu
    370                 375                 380
Gln Tyr Asn Ser Thr Tyr Arg Val Val Ser Val Leu Thr Val Leu His
385                 390                 395                 400
Gln Asp Trp Leu Asn Gly Lys Glu Tyr Lys Cys Lys Val Ser Asn Lys
                405                 410                 415
Ala Leu Pro Ala Pro Ile Glu Lys Thr Ile Ser Lys Ala Lys Gly Gln
            420                 425                 430
Pro Arg Glu Pro Gln Val Tyr Thr Leu Pro Pro Ser Arg Asp Glu Leu
        435                 440                 445
Thr Lys Asn Gln Val Ser Leu Thr Cys Leu Val Lys Gly Phe Tyr Pro

```
                    450              455              460
Ser Asp Ile Ala Val Glu Trp Glu Ser Asn Gly Gln Pro Glu Asn Asn
465                 470              475                  480

Tyr Lys Thr Thr Pro Pro Val Leu Asp Ser Asp Gly Ser Phe Phe Leu
                    485              490                  495

Tyr Ser Lys Leu Thr Val Asp Lys Ser Arg Trp Gln Gln Gly Asn Val
                500                  505                  510

Phe Ser Cys Ser Val Met His Glu Ala Leu His Asn His Tyr Thr Gln
            515                  520                  525

Lys Ser Leu Ser Leu Ser Pro Gly Lys
            530                  535

<210> SEQ ID NO 4
<211> LENGTH: 10
<212> TYPE: PRT
<213> ORGANISM: Artificial Sequence
<220> FEATURE:
<223> OTHER INFORMATION: Synthetic linker

<400> SEQUENCE: 4

Pro Ile Glu Gly Arg Gly Gly Gly Gly Gly
1               5                   10

<210> SEQ ID NO 5
<211> LENGTH: 2292
<212> TYPE: DNA
<213> ORGANISM: Homo sapiens
<220> FEATURE:
<221> NAME/KEY: CDS
<222> LOCATION: (1)..(2292)

<400> SEQUENCE: 5
```

| | | | | | | | | | | | | | | | | |
|---|---|---|---|---|---|---|---|---|---|---|---|---|---|---|---|---|
| atg | gag | agc | aag | gtg | ctg | ctg | gcc | gtc | gcc | ctg | tgg | ctc | tgc | gtg | gag | 48 |
| Met | Glu | Ser | Lys | Val | Leu | Leu | Ala | Val | Ala | Leu | Trp | Leu | Cys | Val | Glu | |
| 1 | | | | 5 | | | | | 10 | | | | | 15 | | |
| acc | cgg | gcc | gcc | tct | gtg | ggt | ttg | cct | agt | gtt | tct | ctt | gat | ctg | ccc | 96 |
| Thr | Arg | Ala | Ala | Ser | Val | Gly | Leu | Pro | Ser | Val | Ser | Leu | Asp | Leu | Pro | |
| | | | 20 | | | | | 25 | | | | | 30 | | | |
| agg | ctc | agc | ata | caa | aaa | gac | ata | ctt | aca | att | aag | gct | aat | aca | act | 144 |
| Arg | Leu | Ser | Ile | Gln | Lys | Asp | Ile | Leu | Thr | Ile | Lys | Ala | Asn | Thr | Thr | |
| | | 35 | | | | | 40 | | | | | 45 | | | | |
| ctt | caa | att | act | tgc | agg | gga | cag | agg | gac | ttg | gac | tgg | ctt | tgg | ccc | 192 |
| Leu | Gln | Ile | Thr | Cys | Arg | Gly | Gln | Arg | Asp | Leu | Asp | Trp | Leu | Trp | Pro | |
| | 50 | | | | | 55 | | | | | 60 | | | | | |
| aat | aat | cag | agt | ggc | agt | gag | caa | agg | gtg | gag | gtg | act | gag | tgc | agc | 240 |
| Asn | Asn | Gln | Ser | Gly | Ser | Glu | Gln | Arg | Val | Glu | Val | Thr | Glu | Cys | Ser | |
| 65 | | | | | 70 | | | | | 75 | | | | | 80 | |
| gat | ggc | ctc | ttc | tgt | aag | aca | ctc | aca | att | cca | aaa | gtg | atc | gga | aat | 288 |
| Asp | Gly | Leu | Phe | Cys | Lys | Thr | Leu | Thr | Ile | Pro | Lys | Val | Ile | Gly | Asn | |
| | | | | 85 | | | | | 90 | | | | | 95 | | |
| gac | act | gga | gcc | tac | aag | tgc | ttc | tac | cgg | gaa | act | gac | ttg | gcc | tcg | 336 |
| Asp | Thr | Gly | Ala | Tyr | Lys | Cys | Phe | Tyr | Arg | Glu | Thr | Asp | Leu | Ala | Ser | |
| | | | 100 | | | | | 105 | | | | | 110 | | | |
| gtc | att | tat | gtc | tat | gtt | caa | gat | tac | aga | tct | cca | ttt | att | gct | tct | 384 |
| Val | Ile | Tyr | Val | Tyr | Val | Gln | Asp | Tyr | Arg | Ser | Pro | Phe | Ile | Ala | Ser | |
| | | 115 | | | | | 120 | | | | | 125 | | | | |
| gtt | agt | gac | caa | cat | gga | gtc | gtg | tac | att | act | gag | aac | aaa | aac | aaa | 432 |
| Val | Ser | Asp | Gln | His | Gly | Val | Val | Tyr | Ile | Thr | Glu | Asn | Lys | Asn | Lys | |
| | 130 | | | | | 135 | | | | | 140 | | | | | |
| act | gtg | gtg | att | cca | tgt | ctc | ggg | tcc | att | tca | aat | ctc | aac | gtg | tca | 480 |
| Thr | Val | Val | Ile | Pro | Cys | Leu | Gly | Ser | Ile | Ser | Asn | Leu | Asn | Val | Ser | |

| | | | | | | | | | | | | | | | |
|---|---|---|---|---|---|---|---|---|---|---|---|---|---|---|---|
| | | 145 | | | | 150 | | | | 155 | | | | 160 | |
| ctt | tgt | gca | aga | tac | cca | gaa | aag | aga | ttt | gtt | cct | gat | ggt | aac | aga | 528
| Leu | Cys | Ala | Arg | Tyr | Pro | Glu | Lys | Arg | Phe | Val | Pro | Asp | Gly | Asn | Arg |
| | | 165 | | | | 170 | | | | 175 | | | | | |
| att | tcc | tgg | gac | agc | aag | aag | ggc | ttt | act | att | ccc | agc | tac | atg | atc | 576
| Ile | Ser | Trp | Asp | Ser | Lys | Lys | Gly | Phe | Thr | Ile | Pro | Ser | Tyr | Met | Ile |
| | | | 180 | | | | 185 | | | | 190 | | | | |
| agc | tat | gct | ggc | atg | gtc | ttc | tgt | gaa | gca | aaa | att | aat | gat | gaa | agt | 624
| Ser | Tyr | Ala | Gly | Met | Val | Phe | Cys | Glu | Ala | Lys | Ile | Asn | Asp | Glu | Ser |
| | | | | 195 | | | | 200 | | | | 205 | | | |
| tac | cag | tct | att | atg | tac | ata | gtt | gtc | gtt | gta | ggg | tat | agg | att | tat | 672
| Tyr | Gln | Ser | Ile | Met | Tyr | Ile | Val | Val | Val | Val | Gly | Tyr | Arg | Ile | Tyr |
| | 210 | | | | 215 | | | | 220 | | | | | | |
| gat | gtg | gtt | ctg | agt | ccg | tct | cat | gga | att | gaa | cta | tct | gtt | gga | gaa | 720
| Asp | Val | Val | Leu | Ser | Pro | Ser | His | Gly | Ile | Glu | Leu | Ser | Val | Gly | Glu |
| 225 | | | | | 230 | | | | 235 | | | | 240 | | |
| aag | ctt | gtc | tta | aat | tgt | aca | gca | aga | act | gaa | cta | aat | gtg | ggg | att | 768
| Lys | Leu | Val | Leu | Asn | Cys | Thr | Ala | Arg | Thr | Glu | Leu | Asn | Val | Gly | Ile |
| | | | | 245 | | | | 250 | | | | 255 | | | |
| gac | ttc | aac | tgg | gaa | tac | cct | tct | tcg | aag | cat | cag | cat | aag | aaa | ctt | 816
| Asp | Phe | Asn | Trp | Glu | Tyr | Pro | Ser | Ser | Lys | His | Gln | His | Lys | Lys | Leu |
| | | 260 | | | | 265 | | | | 270 | | | | | |
| gta | aac | cga | gac | cta | aaa | acc | cag | tct | ggg | agt | gag | atg | aag | aaa | ttt | 864
| Val | Asn | Arg | Asp | Leu | Lys | Thr | Gln | Ser | Gly | Ser | Glu | Met | Lys | Lys | Phe |
| | 275 | | | | 280 | | | | 285 | | | | | | |
| ttg | agc | acc | tta | act | ata | gat | ggt | gta | acc | cgg | agt | gac | caa | gga | ttg | 912
| Leu | Ser | Thr | Leu | Thr | Ile | Asp | Gly | Val | Thr | Arg | Ser | Asp | Gln | Gly | Leu |
| 290 | | | | | 295 | | | | 300 | | | | | | |
| tac | acc | tgt | gca | gca | tcc | agt | ggg | ctg | atg | acc | aag | aag | aac | agc | aca | 960
| Tyr | Thr | Cys | Ala | Ala | Ser | Ser | Gly | Leu | Met | Thr | Lys | Lys | Asn | Ser | Thr |
| 305 | | | | | 310 | | | | 315 | | | | 320 | | |
| ttt | gtc | agg | gtc | cat | gaa | aaa | cct | ttt | gtt | gct | ttt | gga | agt | ggc | atg | 1008
| Phe | Val | Arg | Val | His | Glu | Lys | Pro | Phe | Val | Ala | Phe | Gly | Ser | Gly | Met |
| | | | | 325 | | | | 330 | | | | 335 | | | |
| gaa | tct | ctg | gtg | gaa | gcc | acg | gtg | ggg | gag | cgt | gtc | aga | atc | cct | gcg | 1056
| Glu | Ser | Leu | Val | Glu | Ala | Thr | Val | Gly | Glu | Arg | Val | Arg | Ile | Pro | Ala |
| | | 340 | | | | 345 | | | | 350 | | | | | |
| aag | tac | ctt | ggt | tac | cca | ccc | cca | gaa | ata | aaa | tgg | tat | aaa | aat | gga | 1104
| Lys | Tyr | Leu | Gly | Tyr | Pro | Pro | Pro | Glu | Ile | Lys | Trp | Tyr | Lys | Asn | Gly |
| | 355 | | | | 360 | | | | 365 | | | | | | |
| ata | ccc | ctt | gag | tcc | aat | cac | aca | att | aaa | gcg | ggg | cat | gta | ctg | acg | 1152
| Ile | Pro | Leu | Glu | Ser | Asn | His | Thr | Ile | Lys | Ala | Gly | His | Val | Leu | Thr |
| | 370 | | | | 375 | | | | 380 | | | | | | |
| att | atg | gaa | gtg | agt | gaa | aga | gac | aca | gga | aat | tac | act | gtc | atc | ctt | 1200
| Ile | Met | Glu | Val | Ser | Glu | Arg | Asp | Thr | Gly | Asn | Tyr | Thr | Val | Ile | Leu |
| 385 | | | | | 390 | | | | 395 | | | | 400 | | |
| acc | aat | ccc | att | tca | aag | gag | aag | cag | agc | cat | gtg | gtc | tct | ctg | gtt | 1248
| Thr | Asn | Pro | Ile | Ser | Lys | Glu | Lys | Gln | Ser | His | Val | Val | Ser | Leu | Val |
| | | | | 405 | | | | 410 | | | | 415 | | | |
| gtg | tat | gtc | cca | ccc | cag | att | ggt | gag | aaa | tct | cta | atc | tct | cct | gtg | 1296
| Val | Tyr | Val | Pro | Pro | Gln | Ile | Gly | Glu | Lys | Ser | Leu | Ile | Ser | Pro | Val |
| | | | 420 | | | | 425 | | | | 430 | | | | |
| gat | tcc | tac | cag | tac | ggc | acc | act | caa | acg | ctg | aca | tgt | acg | gtc | tat | 1344
| Asp | Ser | Tyr | Gln | Tyr | Gly | Thr | Thr | Gln | Thr | Leu | Thr | Cys | Thr | Val | Tyr |
| | | 435 | | | | 440 | | | | 445 | | | | | |
| gcc | att | cct | ccc | ccg | cat | cac | atc | cac | tgg | tat | tgg | cag | ttg | gag | gaa | 1392
| Ala | Ile | Pro | Pro | Pro | His | His | Ile | His | Trp | Tyr | Trp | Gln | Leu | Glu | Glu |
| | 450 | | | | 455 | | | | 460 | | | | | | |
| gag | tgc | gcc | aac | gag | ccc | agc | caa | gct | gtc | tca | gtg | aca | aac | cca | tac | 1440

```
                Glu Cys Ala Asn Glu Pro Ser Gln Ala Val Ser Val Thr Asn Pro Tyr
                465                 470                 475                 480 cct tgt gaa gaa tgg aga agt gtg gag gac ttc cag gga gga aat aaa      1488
Pro Cys Glu Glu Trp Arg Ser Val Glu Asp Phe Gln Gly Gly Asn Lys
                485                 490                 495 att gaa gtt aat aaa aat caa ttt gct cta att gaa gga aaa aac aaa      1536
Ile Glu Val Asn Lys Asn Gln Phe Ala Leu Ile Glu Gly Lys Asn Lys
                500                 505                 510 act gta agt acc ctt gtt atc caa gcg gca aat gtg tca gct ttg tac      1584
Thr Val Ser Thr Leu Val Ile Gln Ala Ala Asn Val Ser Ala Leu Tyr
                515                 520                 525 aaa tgt gaa gcg gtc aac aaa gtc ggg aga gga gag agg gtg atc tcc      1632
Lys Cys Glu Ala Val Asn Lys Val Gly Arg Gly Glu Arg Val Ile Ser
                530                 535                 540 ttc cac gtg acc agg ggt cct gaa att act ttg caa cct gac atg cag      1680
Phe His Val Thr Arg Gly Pro Glu Ile Thr Leu Gln Pro Asp Met Gln
545                 550                 555                 560 ccc act gag cag gag agc gtg tct ttg tgg tgc act gca gac aga tct      1728
Pro Thr Glu Gln Glu Ser Val Ser Leu Trp Cys Thr Ala Asp Arg Ser
                565                 570                 575 acg ttt gag aac ctc aca tgg tac aag ctt ggc cca cag cct ctg cca      1776
Thr Phe Glu Asn Leu Thr Trp Tyr Lys Leu Gly Pro Gln Pro Leu Pro
                580                 585                 590 atc cat gtg gga gag ttg ccc aca cct gtt tgc aag aac ttg gat act      1824
Ile His Val Gly Glu Leu Pro Thr Pro Val Cys Lys Asn Leu Asp Thr
                595                 600                 605 ctt tgg aaa ttg aat gcc acc atg ttc tct aat agc aca aat gac att      1872
Leu Trp Lys Leu Asn Ala Thr Met Phe Ser Asn Ser Thr Asn Asp Ile
610                 615                 620 ttg atc atg gag ctt aag aat gca tcc ttg cag gac caa gga gac tat      1920
Leu Ile Met Glu Leu Lys Asn Ala Ser Leu Gln Asp Gln Gly Asp Tyr
625                 630                 635                 640 gtc tgc ctt gct caa gac agg aag acc aag aaa aga cat tgc gtg gtc      1968
Val Cys Leu Ala Gln Asp Arg Lys Thr Lys Lys Arg His Cys Val Val
                645                 650                 655 agg cag ctc aca gtc cta gag cgt gtg gca ccc acg atc aca gga aac      2016
Arg Gln Leu Thr Val Leu Glu Arg Val Ala Pro Thr Ile Thr Gly Asn
                660                 665                 670 ctg gag aat cag acg aca agt att ggg gaa agc atc gaa gtc tca tgc      2064
Leu Glu Asn Gln Thr Thr Ser Ile Gly Glu Ser Ile Glu Val Ser Cys
                675                 680                 685 acg gca tct ggg aat ccc cct cca cag atc atg tgg ttt aaa gat aat      2112
Thr Ala Ser Gly Asn Pro Pro Pro Gln Ile Met Trp Phe Lys Asp Asn
                690                 695                 700 gag acc ctt gta gaa gac tca ggc att gta ttg aag gat ggg aac cgg      2160
Glu Thr Leu Val Glu Asp Ser Gly Ile Val Leu Lys Asp Gly Asn Arg
705                 710                 715                 720 aac ctc act atc cgc aga gtg agg aag gag gac gaa ggc ctc tac acc      2208
Asn Leu Thr Ile Arg Arg Val Arg Lys Glu Asp Glu Gly Leu Tyr Thr
                725                 730                 735 tgc cag gca tgc agt gtt ctt ggc tgt gca aaa gtg gag gca ttt ttc      2256
Cys Gln Ala Cys Ser Val Leu Gly Cys Ala Lys Val Glu Ala Phe Phe
                740                 745                 750 ata ata gaa ggt gcc cag gaa aag acg aac ttg gaa                      2292
Ile Ile Glu Gly Ala Gln Glu Lys Thr Asn Leu Glu
                755                 760

<210> SEQ ID NO 6
<211> LENGTH: 764
<212> TYPE: PRT
```

-continued

<213> ORGANISM: Homo sapiens

<400> SEQUENCE: 6

Met Glu Ser Lys Val Leu Leu Ala Val Ala Leu Trp Leu Cys Val Glu
1               5                  10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

```
Thr Asn Pro Ile Ser Lys Glu Lys Gln Ser His Val Val Ser Leu Val
                405                 410                 415
Val Tyr Val Pro Pro Gln Ile Gly Glu Lys Ser Leu Ile Ser Pro Val
            420                 425                 430
Asp Ser Tyr Gln Tyr Gly Thr Thr Gln Thr Leu Thr Cys Thr Val Tyr
        435                 440                 445
Ala Ile Pro Pro Pro His His Ile His Trp Tyr Trp Gln Leu Glu Glu
    450                 455                 460
Glu Cys Ala Asn Glu Pro Ser Gln Ala Val Ser Val Thr Asn Pro Tyr
465                 470                 475                 480
Pro Cys Glu Glu Trp Arg Ser Val Glu Asp Phe Gln Gly Gly Asn Lys
                485                 490                 495
Ile Glu Val Asn Lys Asn Gln Phe Ala Leu Ile Glu Gly Lys Asn Lys
            500                 505                 510
Thr Val Ser Thr Leu Val Ile Gln Ala Ala Asn Val Ser Ala Leu Tyr
        515                 520                 525
Lys Cys Glu Ala Val Asn Lys Val Gly Arg Gly Glu Arg Val Ile Ser
    530                 535                 540
Phe His Val Thr Arg Gly Pro Glu Ile Thr Leu Gln Pro Asp Met Gln
545                 550                 555                 560
Pro Thr Glu Gln Glu Ser Val Ser Leu Trp Cys Thr Ala Asp Arg Ser
                565                 570                 575
Thr Phe Glu Asn Leu Thr Trp Tyr Lys Leu Gly Pro Gln Pro Leu Pro
            580                 585                 590
Ile His Val Gly Glu Leu Pro Thr Pro Val Cys Lys Asn Leu Asp Thr
        595                 600                 605
Leu Trp Lys Leu Asn Ala Thr Met Phe Ser Asn Ser Thr Asn Asp Ile
    610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Lys Arg His Cys Val Val
                645                 650                 655
Arg Gln Leu Thr Val Leu Glu Arg Val Ala Pro Thr Ile Thr Gly Asn
            660                 665                 670
Leu Glu Asn Gln Thr Thr Ser Ile Gly Glu Ser Ile Glu Val Ser Cys
        675                 680                 685
Thr Ala Ser Gly Asn Pro Pro Pro Gln Ile Met Trp Phe Lys Asp Asn
    690                 695                 700
Glu Thr Leu Val Glu Asp Ser Gly Ile Val Leu Lys Asp Gly Asn Arg
705                 710                 715                 720
Asn Leu Thr Ile Arg Arg Val Arg Lys Glu Asp Glu Gly Leu Tyr Thr
                725                 730                 735
Cys Gln Ala Cys Ser Val Leu Gly Cys Ala Lys Val Glu Ala Phe Phe
            740                 745                 750
Ile Ile Glu Gly Ala Gln Glu Lys Thr Asn Leu Glu
        755                 760

<210> SEQ ID NO 7
<211> LENGTH: 13
<212> TYPE: PRT
<213> ORGANISM: Artificial Sequence
<220> FEATURE:
<223> OTHER INFORMATION: Synthetic linker

<400> SEQUENCE: 7
```

```
Glu Phe Gly Ala Gly Leu Val Leu Gly Gly Gln Phe Met
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Synthetic linker

<400> SEQUENCE: 8

Gly Gly Gly Gly Ser Gly Gly Gly Ser Gly Gly Gly Gly Ser
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic linker

<400> SEQUENCE: 9

Gly Gly Ser Gly Gly Ser Gly Gly Gly Ser Gly Gly Gly Gly Ser
1               5                   10                      15

<210> SEQ ID NO 10
<211> LENGTH: 5777
<212> TYPE: DNA
<213> ORGANISM: Homo sapiens
<220> FEATURE:
<221> NAME/KEY: misc_feature
<223> OTHER INFORMATION: VEGFR-1
<220> FEATURE:
<221> NAME/KEY: CDS
<222> LOCATION: (250)..(4266)

<400> SEQUENCE: 10
```

| | |
|---|---|
| gcggacactc ctctcggctc tccccggca gcggcggcgg ctcggagcgg gctccggggc | 60 |
| tcgggtgcag cggccagcgg gcctggcggc gaggattacc cggggaagtg gttgtctcct | 120 |
| ggctggagcc gcgagacggg cgctcagggc gcggggccgg cggcggcgaa cgagaggacg | 180 |
| gactctggcg gccgggtcgt tggccggggg agcgcgggca ccgggcgagc aggccgcgtc | 240 |

```
gcgctcacc atg gtc agc tac tgg gac acc ggg gtc ctg ctg tgc gcg ctg      291
          Met Val Ser Tyr Trp Asp Thr Gly Val Leu Leu Cys Ala Leu
            1               5                   10 ctc agc tgt ctg ctt ctc aca gga tct agt tca ggt tca aaa tta aaa       339
Leu Ser Cys Leu Leu Leu Thr Gly Ser Ser Ser Gly Ser Lys Leu Lys
 15                  20                  25                  30 gat cct gaa ctg agt tta aaa ggc acc cag cac atc atg caa gca ggc       387
Asp Pro Glu Leu Ser Leu Lys Gly Thr Gln His Ile Met Gln Ala Gly
                 35                  40                  45 cag aca ctg cat ctc caa tgc agg ggg gaa gca gcc cat aaa tgg tct       435
Gln Thr Leu His Leu Gln Cys Arg Gly Glu Ala Ala His Lys Trp Ser
         50                  55                  60 ttg cct gaa atg gtg agt aag gaa agc gaa agg ctg agc ata act aaa       483
Leu Pro Glu Met Val Ser Lys Glu Ser Glu Arg Leu Ser Ile Thr Lys
 65                  70                  75 tct gcc tgt gga aga aat ggc aaa caa ttc tgc agt act tta acc ttg       531
Ser Ala Cys Gly Arg Asn Gly Lys Gln Phe Cys Ser Thr Leu Thr Leu
             80                  85                  90 aac aca gct caa gca aac cac act ggc ttc tac agc tgc aaa tat cta       579
Asn Thr Ala Gln Ala Asn His Thr Gly Phe Tyr Ser Cys Lys Tyr Leu
 95                 100                 105                 110
```

```
gct gta cct act tca aag aag aag gaa aca gaa tct gca atc tat ata        627
Ala Val Pro Thr Ser Lys Lys Lys Glu Thr Glu Ser Ala Ile Tyr Ile
            115             120                 125 ttt att agt gat aca ggt aga cct ttc gta gag atg tac agt gaa atc        675
Phe Ile Ser Asp Thr Gly Arg Pro Phe Val Glu Met Tyr Ser Glu Ile
            130             135                 140 ccc gaa att ata cac atg act gaa gga agg gag ctc gtc att ccc tgc        723
Pro Glu Ile Ile His Met Thr Glu Gly Arg Glu Leu Val Ile Pro Cys
            145             150                 155 cgg gtt acg tca cct aac atc act gtt act tta aaa aag ttt cca ctt        771
Arg Val Thr Ser Pro Asn Ile Thr Val Thr Leu Lys Lys Phe Pro Leu
            160             165                 170 gac act ttg atc cct gat gga aaa cgc ata atc tgg gac agt aga aag        819
Asp Thr Leu Ile Pro Asp Gly Lys Arg Ile Ile Trp Asp Ser Arg Lys
175             180             185                 190 ggc ttc atc ata tca aat gca acg tac aaa gaa ata ggg ctt ctg acc        867
Gly Phe Ile Ile Ser Asn Ala Thr Tyr Lys Glu Ile Gly Leu Leu Thr
                195             200                 205 tgt gaa gca aca gtc aat ggg cat ttg tat aag aca aac tat ctc aca        915
Cys Glu Ala Thr Val Asn Gly His Leu Tyr Lys Thr Asn Tyr Leu Thr
            210             215                 220 cat cga caa acc aat aca atc ata gat gtc caa ata agc aca cca cgc        963
His Arg Gln Thr Asn Thr Ile Ile Asp Val Gln Ile Ser Thr Pro Arg
            225             230                 235 cca gtc aaa tta ctt aga ggc cat act ctt gtc ctc aat tgt act gct       1011
Pro Val Lys Leu Leu Arg Gly His Thr Leu Val Leu Asn Cys Thr Ala
240             245                 250 acc act ccc ttg aac acg aga gtt caa atg acc tgg agt tac cct gat       1059
Thr Thr Pro Leu Asn Thr Arg Val Gln Met Thr Trp Ser Tyr Pro Asp
255             260             265                 270 gaa aaa aat aag aga gct tcc gta agg cga cga att gac caa agc aat       1107
Glu Lys Asn Lys Arg Ala Ser Val Arg Arg Ile Asp Gln Ser Asn
                275             280                 285 tcc cat gcc aac ata ttc tac agt gtt ctt act att gac aaa atg cag       1155
Ser His Ala Asn Ile Phe Tyr Ser Val Leu Thr Ile Asp Lys Met Gln
            290             295                 300 aac aaa gac aaa gga ctt tat act tgt cgt gta agg agt gga cca tca       1203
Asn Lys Asp Lys Gly Leu Tyr Thr Cys Arg Val Arg Ser Gly Pro Ser
            305             310                 315 ttc aaa tct gtt aac acc tca gtg cat ata tat gat aaa gca ttc atc       1251
Phe Lys Ser Val Asn Thr Ser Val His Ile Tyr Asp Lys Ala Phe Ile
320             325                 330 act gtg aaa cat cga aaa cag cag gtg ctt gaa acc gta gct ggc aag       1299
Thr Val Lys His Arg Lys Gln Gln Val Leu Glu Thr Val Ala Gly Lys
335             340             345                 350 cgg tct tac cgg ctc tct atg aaa gtg aag gca ttt ccc tcg ccg gaa       1347
Arg Ser Tyr Arg Leu Ser Met Lys Val Lys Ala Phe Pro Ser Pro Glu
            355             360                 365 gtt gta tgg tta aaa gat ggg tta cct gcg act gag aaa tct gct cgc       1395
Val Val Trp Leu Lys Asp Gly Leu Pro Ala Thr Glu Lys Ser Ala Arg
            370             375                 380 tat ttg act cgt ggc tac tcg tta att atc aag gac gta act gaa gag       1443
Tyr Leu Thr Arg Gly Tyr Ser Leu Ile Ile Lys Asp Val Thr Glu Glu
            385             390                 395 gat gca ggg aat tat aca atc ttg ctg agc ata aaa cag tca aat gtg       1491
Asp Ala Gly Asn Tyr Thr Ile Leu Leu Ser Ile Lys Gln Ser Asn Val
            400             405                 410 ttt aaa aac ctc act gcc act cta att gtc aat gtg aaa ccc cag att       1539
Phe Lys Asn Leu Thr Ala Thr Leu Ile Val Asn Val Lys Pro Gln Ile
415             420                 425                 430
```

```
tac gaa aag gcc gtg tca tcg ttt cca gac ccg gct ctc tac cca ctg      1587
Tyr Glu Lys Ala Val Ser Ser Phe Pro Asp Pro Ala Leu Tyr Pro Leu
            435                 440                 445 ggc agc aga caa atc ctg act tgt acc gca tat ggt atc cct caa cct      1635
Gly Ser Arg Gln Ile Leu Thr Cys Thr Ala Tyr Gly Ile Pro Gln Pro
        450                 455                 460 aca atc aag tgg ttc tgg cac ccc tgt aac cat aat cat tcc gaa gca      1683
Thr Ile Lys Trp Phe Trp His Pro Cys Asn His Asn His Ser Glu Ala
    465                 470                 475 agg tgt gac ttt tgt tcc aat aat gaa gag tcc ttt atc ctg gat gct      1731
Arg Cys Asp Phe Cys Ser Asn Asn Glu Glu Ser Phe Ile Leu Asp Ala
480                 485                 490 gac agc aac atg gga aac aga att gag agc atc act cag cgc atg gca      1779
Asp Ser Asn Met Gly Asn Arg Ile Glu Ser Ile Thr Gln Arg Met Ala
495                 500                 505                 510 ata ata gaa gga aag aat aag atg gct agc acc ttg gtt gtg gct gac      1827
Ile Ile Glu Gly Lys Asn Lys Met Ala Ser Thr Leu Val Val Ala Asp
                515                 520                 525 tct aga att tct gga atc tac att tgc ata gct tcc aat aaa gtt ggg      1875
Ser Arg Ile Ser Gly Ile Tyr Ile Cys Ile Ala Ser Asn Lys Val Gly
            530                 535                 540 act gtg gga aga aac ata agc ttt tat atc aca gat gtg cca aat ggg      1923
Thr Val Gly Arg Asn Ile Ser Phe Tyr Ile Thr Asp Val Pro Asn Gly
        545                 550                 555 ttt cat gtt aac ttg gaa aaa atg ccg acg gaa gga gag gac ctg aaa      1971
Phe His Val Asn Leu Glu Lys Met Pro Thr Glu Gly Glu Asp Leu Lys
    560                 565                 570 ctg tct tgc aca gtt aac aag ttc tta tac aga gac gtt act tgg att      2019
Leu Ser Cys Thr Val Asn Lys Phe Leu Tyr Arg Asp Val Thr Trp Ile
575                 580                 585                 590 tta ctg cgg aca gtt aat aac aga aca atg cac tac agt att agc aag      2067
Leu Leu Arg Thr Val Asn Asn Arg Thr Met His Tyr Ser Ile Ser Lys
                595                 600                 605 caa aaa atg gcc atc act aag gag cac tcc atc act ctt aat ctt acc      2115
Gln Lys Met Ala Ile Thr Lys Glu His Ser Ile Thr Leu Asn Leu Thr
            610                 615                 620 atc atg aat gtt tcc ctg caa gat tca ggc acc tat gcc tgc aga gcc      2163
Ile Met Asn Val Ser Leu Gln Asp Ser Gly Thr Tyr Ala Cys Arg Ala
        625                 630                 635 agg aat gta tac aca ggg gaa gaa atc ctc cag aag aaa gaa att aca      2211
Arg Asn Val Tyr Thr Gly Glu Glu Ile Leu Gln Lys Lys Glu Ile Thr
    640                 645                 650 atc aga gat cag gaa gca cca tac ctc ctg cga aac ctc agt gat cac      2259
Ile Arg Asp Gln Glu Ala Pro Tyr Leu Leu Arg Asn Leu Ser Asp His
655                 660                 665                 670 aca gtg gcc atc agc agt tcc acc act tta gac tgt cat gct aat ggt      2307
Thr Val Ala Ile Ser Ser Ser Thr Thr Leu Asp Cys His Ala Asn Gly
                675                 680                 685 gtc ccc gag cct cag atc act tgg ttt aaa aac aac cac aaa ata caa      2355
Val Pro Glu Pro Gln Ile Thr Trp Phe Lys Asn Asn His Lys Ile Gln
            690                 695                 700 caa gag cct gga att att tta gga cca gga agc agc acg ctg ttt att      2403
Gln Glu Pro Gly Ile Ile Leu Gly Pro Gly Ser Ser Thr Leu Phe Ile
        705                 710                 715 gaa aga gtc aca gaa gag gat gaa ggt gtc tat cac tgc aaa gcc acc      2451
Glu Arg Val Thr Glu Glu Asp Glu Gly Val Tyr His Cys Lys Ala Thr
    720                 725                 730 aac cag aag ggc tct gtg gaa agt tca gca tac ctc act gtt caa gga      2499
Asn Gln Lys Gly Ser Val Glu Ser Ser Ala Tyr Leu Thr Val Gln Gly
```

```
              735                  740                  745                  750
acc tcg gac aag tct aat ctg gag ctg atc act cta aca tgc acc tgt           2547
Thr Ser Asp Lys Ser Asn Leu Glu Leu Ile Thr Leu Thr Cys Thr Cys
                    755                  760                  765 gtg gct gcg act ctc ttc tgg ctc cta tta acc ctc ctt atc cga aaa           2595
Val Ala Ala Thr Leu Phe Trp Leu Leu Leu Thr Leu Leu Ile Arg Lys
                770                  775                  780 atg aaa agg tct tct tct gaa ata aag act gac tac cta tca att ata           2643
Met Lys Arg Ser Ser Ser Glu Ile Lys Thr Asp Tyr Leu Ser Ile Ile
                785                  790                  795 atg gac cca gat gaa gtt cct ttg gat gag cag tgt gag cgg ctc cct           2691
Met Asp Pro Asp Glu Val Pro Leu Asp Glu Gln Cys Glu Arg Leu Pro
            800                  805                  810 tat gat gcc agc aag tgg gag ttt gcc cgg gag aga ctt aaa ctg ggc           2739
Tyr Asp Ala Ser Lys Trp Glu Phe Ala Arg Glu Arg Leu Lys Leu Gly
815                  820                  825                  830 aaa tca ctt gga aga ggg gct ttt gga aaa gtg gtt caa gca tca gca           2787
Lys Ser Leu Gly Arg Gly Ala Phe Gly Lys Val Val Gln Ala Ser Ala
                    835                  840                  845 ttt ggc att aag aaa tca cct acg tgc cgg act gtg gct gtg aaa atg           2835
Phe Gly Ile Lys Lys Ser Pro Thr Cys Arg Thr Val Ala Val Lys Met
                850                  855                  860 ctg aaa gag ggg gcc acg gcc agc gag tac aaa gct ctg atg act gag           2883
Leu Lys Glu Gly Ala Thr Ala Ser Glu Tyr Lys Ala Leu Met Thr Glu
            865                  870                  875 cta aaa atc ttg acc cac att ggc cac cat ctg aac gtg gtt aac ctg           2931
Leu Lys Ile Leu Thr His Ile Gly His His Leu Asn Val Val Asn Leu
        880                  885                  890 ctg gga gcc tgc acc aag caa gga ggg cct ctg atg gtg att gtt gaa           2979
Leu Gly Ala Cys Thr Lys Gln Gly Gly Pro Leu Met Val Ile Val Glu
895                  900                  905                  910 tac tgc aaa tat gga aat ctc tcc aac tac ctc aag agc aaa cgt gac           3027
Tyr Cys Lys Tyr Gly Asn Leu Ser Asn Tyr Leu Lys Ser Lys Arg Asp
                    915                  920                  925 tta ttt ttt ctc aac aag gat gca gca cta cac atg gag cct aag aaa           3075
Leu Phe Phe Leu Asn Lys Asp Ala Ala Leu His Met Glu Pro Lys Lys
                930                  935                  940 gaa aaa atg gag cca ggc ctg gaa caa ggc aag aaa cca aga cta gat           3123
Glu Lys Met Glu Pro Gly Leu Glu Gln Gly Lys Lys Pro Arg Leu Asp
            945                  950                  955 agc gtc acc agc agc gaa agc ttt gcg agc tcc ggc ttt cag gaa gat           3171
Ser Val Thr Ser Ser Glu Ser Phe Ala Ser Ser Gly Phe Gln Glu Asp
        960                  965                  970 aaa agt ctg agt gat gtt gag gaa gag gag gat tct gac ggt ttc tac           3219
Lys Ser Leu Ser Asp Val Glu Glu Glu Glu Asp Ser Asp Gly Phe Tyr
975                  980                  985                  990 aag gag ccc atc act atg gaa gat ctg att tct tac agt ttt caa gtg           3267
Lys Glu Pro Ile Thr Met Glu Asp Leu Ile Ser Tyr Ser Phe Gln Val
                    995                  1000                 1005 gcc aga ggc atg gag ttc ctg tct tcc aga aag tgc att cat cgg              3312
Ala Arg Gly Met Glu Phe Leu Ser Ser Arg Lys Cys Ile His Arg
                1010                 1015                 1020 gac ctg gca gcg aga aac att ctt tta tct gag aac aac gtg gtg              3357
Asp Leu Ala Ala Arg Asn Ile Leu Leu Ser Glu Asn Asn Val Val
                1025                 1030                 1035 aag att tgt gat ttt ggc ctt gcc cgg gat att tat aag aac ccc              3402
Lys Ile Cys Asp Phe Gly Leu Ala Arg Asp Ile Tyr Lys Asn Pro
                1040                 1045                 1050 gat tat gtg aga aaa gga gat act cga ctt cct ctg aaa tgg atg              3447
```

```
                                                      -continued

Asp Tyr Val Arg Lys Gly Asp Thr Arg Leu Pro Leu Lys Trp Met
        1055            1060            1065 gct ccc gaa tct atc ttt gac aaa atc tac agc acc aag agc gac    3492
Ala Pro Glu Ser Ile Phe Asp Lys Ile Tyr Ser Thr Lys Ser Asp
        1070            1075            1080 gtg tgg tct tac gga gta ttg ctg tgg gaa atc ttc tcc tta ggt    3537
Val Trp Ser Tyr Gly Val Leu Leu Trp Glu Ile Phe Ser Leu Gly
        1085            1090            1095 ggg tct cca tac cca gga gta caa atg gat gag gac ttt tgc agt    3582
Gly Ser Pro Tyr Pro Gly Val Gln Met Asp Glu Asp Phe Cys Ser
        1100            1105            1110 cgc ctg agg gaa ggc atg agg atg aga gct cct gag tac tct act    3627
Arg Leu Arg Glu Gly Met Arg Met Arg Ala Pro Glu Tyr Ser Thr
        1115            1120            1125 cct gaa atc tat cag atc atg ctg gac tgc tgg cac aga gac cca    3672
Pro Glu Ile Tyr Gln Ile Met Leu Asp Cys Trp His Arg Asp Pro
        1130            1135            1140 aaa gaa agg cca aga ttt gca gaa ctt gtg gaa aaa cta ggt gat    3717
Lys Glu Arg Pro Arg Phe Ala Glu Leu Val Glu Lys Leu Gly Asp
        1145            1150            1155 ttg ctt caa gca aat gta caa cag gat ggt aaa gac tac atc cca    3762
Leu Leu Gln Ala Asn Val Gln Gln Asp Gly Lys Asp Tyr Ile Pro
        1160            1165            1170 atc aat gcc ata ctg aca gga aat agt ggg ttt aca tac tca act    3807
Ile Asn Ala Ile Leu Thr Gly Asn Ser Gly Phe Thr Tyr Ser Thr
        1175            1180            1185 cct gcc ttc tct gag gac ttc ttc aag gaa agt att tca gct ccg    3852
Pro Ala Phe Ser Glu Asp Phe Phe Lys Glu Ser Ile Ser Ala Pro
        1190            1195            1200 aag ttt aat tca gga agc tct gat gat gtc aga tat gta aat gct    3897
Lys Phe Asn Ser Gly Ser Ser Asp Asp Val Arg Tyr Val Asn Ala
        1205            1210            1215 ttc aag ttc atg agc ctg gaa aga atc aaa acc ttt gaa gaa ctt    3942
Phe Lys Phe Met Ser Leu Glu Arg Ile Lys Thr Phe Glu Glu Leu
        1220            1225            1230 tta ccg aat gcc acc tcc atg ttt gat gac tac cag ggc gac agc    3987
Leu Pro Asn Ala Thr Ser Met Phe Asp Asp Tyr Gln Gly Asp Ser
        1235            1240            1245 agc act ctg ttg gcc tct ccc atg ctg aag cgc ttc acc tgg act    4032
Ser Thr Leu Leu Ala Ser Pro Met Leu Lys Arg Phe Thr Trp Thr
        1250            1255            1260 gac agc aaa ccc aag gcc tcg ctc aag att gac ttg aga gta acc    4077
Asp Ser Lys Pro Lys Ala Ser Leu Lys Ile Asp Leu Arg Val Thr
        1265            1270            1275 agt aaa agt aag gag tcg ggg ctg tct gat gtc agc agg ccc agt    4122
Ser Lys Ser Lys Glu Ser Gly Leu Ser Asp Val Ser Arg Pro Ser
        1280            1285            1290 ttc tgc cat tcc agc tgt ggg cac gtc agc gaa ggc aag cgc agg    4167
Phe Cys His Ser Ser Cys Gly His Val Ser Glu Gly Lys Arg Arg
        1295            1300            1305 ttc acc tac gac cac gct gag ctg gaa agg aaa atc gcg tgc tgc    4212
Phe Thr Tyr Asp His Ala Glu Leu Glu Arg Lys Ile Ala Cys Cys
        1310            1315            1320 tcc ccg ccc cca gac tac aac tcg gtg gtc ctg tac tcc acc cca    4257
Ser Pro Pro Pro Asp Tyr Asn Ser Val Val Leu Tyr Ser Thr Pro
        1325            1330            1335 ccc atc tag agtttgacac gaagccttat ttctagaagc acatgtgtat         4306
Pro Ile ttataccccc aggaaactag cttttgccag tattatgcat ataagttt acacctttat  4366
```

-continued

```
ctttccatgg gagccagctg cttttttgtga tttttttaat agtgcttttt tttttttgact    4426
aacaagaatg taactccaga tagagaaata gtgacaagtg aagaacacta ctgctaaatc    4486
ctcatgttac tcagtgttag agaaatcctt cctaaaccca atgactccc tgctccaacc    4546
cccgccacct cagggcacgc aggaccagtt tgattgagga gctgcactga tcacccaatg    4606
catcacgtac cccactgggc cagccctgca gcccaaaacc cagggcaaca agcccgttag    4666
ccccagggga tcactggctg gcctgagcaa catctcggga gtcctctagc aggcctaaga    4726
catgtgagga ggaaaaggaa aaaagcaaa aagcaaggga gaaagagaaa accgggagaa    4786
ggcatgagaa agaatttgag acgcaccatg tgggcacgga ggggacggg gctcagcaat    4846
gccatttcag tggcttccca gctctgaccc ttctacattt gagggcccag ccaggagcag    4906
atggacagcg atgaggggac attttctgga ttctgggagg caagaaaagg acaaatatct    4966
tttttggaac taaagcaaat tttagacctt tacctatgga agtggttcta tgtccattct    5026
cattcgtggc atgttttgat ttgtagcact gagggtggca ctcaactctg agcccatact    5086
tttggctcct ctagtaagat gcactgaaaa cttagccaga gttaggttgt ctccaggcca    5146
tgatggcctt acactgaaaa tgtcacattc tattttgggt attaatatat agtccagaca    5206
cttaactcaa tttcttggta ttattctgtt ttgcacagtt agttgtgaaa gaaagctgag    5266
aagaatgaaa atgcagtcct gaggagagtt ttctccatat caaaacgagg gctgatggag    5326
gaaaaaggtc aataaggtca agggaagacc ccgtctctat accaaccaaa ccaattcacc    5386
aacacagttg ggacccaaaa cacaggaagt cagtcacgtt cctttttcat ttaatgggga    5446
ttccactatc tcacactaat ctgaaaggat gtggaagagc attagctggc gcatattaag    5506
cactttaagc tccttgagta aaaggtggt atgtaattta tgcaaggtat ttctccagtt    5566
gggactcagg atattagtta atgagccatc actagaagaa aagcccattt tcaactgctt    5626
tgaaacttgc ctggggtctg agcatgatgg gaatagggag acagggtagg aaagggcgcc    5686
tactcttcag ggtctaaaga tcaagtgggc cttggatcgc taagctggct ctgtttgatg    5746
ctatttatgc aagttagggt ctatgtattt a                                      5777
```

<210> SEQ ID NO 11
<211> LENGTH: 1338
<212> TYPE: PRT
<213> ORGANISM: Homo sapiens

<400> SEQUENCE: 11

```
Met Val Ser Tyr Trp Asp Thr Gly Val Leu Leu Cys Ala Leu Leu Ser
1               5                   10                  15

Cys Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
```

-continued

```
            115                 120                 125
Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                    165                 170                 175

Leu Ile Pro Asp Gly Lys Arg Ile Ile Trp Asp Ser Arg Lys Gly Phe
                180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
        210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                    245                 250                 255

Pro Leu Asn Thr Arg Val Gln Met Thr Trp Ser Tyr Pro Asp Glu Lys
                260                 265                 270

Asn Lys Arg Ala Ser Val Arg Arg Ile Asp Gln Ser Asn Ser His
            275                 280                 285

Ala Asn Ile Phe Tyr Ser Val Leu Thr Ile Asp Lys Met Gln Asn Lys
        290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                    325                 330                 335

Lys His Arg Lys Gln Gln Val Leu Glu Thr Val Ala Gly Lys Arg Ser
                340                 345                 350

Tyr Arg Leu Ser Met Lys Val Lys Ala Phe Pro Ser Pro Glu Val Val
            355                 360                 365

Trp Leu Lys Asp Gly Leu Pro Ala Thr Glu Lys Ser Ala Arg Tyr Leu
        370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                    405                 410                 415

Asn Leu Thr Ala Thr Leu Ile Val Asn Val Lys Pro Gln Ile Tyr Glu
                420                 425                 430

Lys Ala Val Ser Ser Phe Pro Asp Pro Ala Leu Tyr Pro Leu Gly Ser
            435                 440                 445

Arg Gln Ile Leu Thr Cys Thr Ala Tyr Gly Ile Pro Gln Pro Thr Ile
        450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                    485                 490                 495

Asn Met Gly Asn Arg Ile Glu Ser Ile Thr Gln Arg Met Ala Ile Ile
                500                 505                 510

Glu Gly Lys Asn Lys Met Ala Ser Thr Leu Val Val Ala Asp Ser Arg
            515                 520                 525

Ile Ser Gly Ile Tyr Ile Cys Ile Ala Ser Asn Lys Val Gly Thr Val
        530                 535                 540
```

-continued

```
Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
    690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
        755                 760                 765

Ala Thr Leu Phe Trp Leu Leu Leu Thr Leu Leu Ile Arg Lys Met Lys
    770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
        835                 840                 845

Ile Lys Lys Ser Pro Thr Cys Arg Thr Val Ala Val Lys Met Leu Lys
    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
        915                 920                 925

Phe Leu Asn Lys Asp Ala Ala Leu His Met Glu Pro Lys Lys Glu Lys
    930                 935                 940

Met Glu Pro Gly Leu Glu Gln Gly Lys Lys Pro Arg Leu Asp Ser Val
945                 950                 955                 960
```

-continued

Thr Ser Ser Glu Ser Phe Ala Ser Ser Gly Phe Gln Glu Asp Lys Ser
                965                 970                 975

Leu Ser Asp Val Glu Glu Glu Asp Ser Asp Gly Phe Tyr Lys Glu
            980                 985                 990

Pro Ile Thr Met Glu Asp Leu Ile Ser Tyr Ser Phe Gln Val Ala Arg
            995                 1000                1005

Gly Met Glu Phe Leu Ser Ser Arg Lys Cys Ile His Arg Asp Leu
    1010                1015                1020

Ala Ala Arg Asn Ile Leu Leu Ser Glu Asn Asn Val Val Lys Ile
    1025                1030                1035

Cys Asp Phe Gly Leu Ala Arg Asp Ile Tyr Lys Asn Pro Asp Tyr
    1040                1045                1050

Val Arg Lys Gly Asp Thr Arg Leu Pro Leu Lys Trp Met Ala Pro
    1055                1060                1065

Glu Ser Ile Phe Asp Lys Ile Tyr Ser Thr Lys Ser Asp Val Trp
    1070                1075                1080

Ser Tyr Gly Val Leu Leu Trp Glu Ile Phe Ser Leu Gly Gly Ser
    1085                1090                1095

Pro Tyr Pro Gly Val Gln Met Asp Glu Asp Phe Cys Ser Arg Leu
    1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

Arg Pro Arg Phe Ala Glu Leu Val Glu Lys Leu Gly Asp Leu Leu
    1145                1150                1155

Gln Ala Asn Val Gln Gln Asp Gly Lys Asp Tyr Ile Pro Ile Asn
    1160                1165                1170

Ala Ile Leu Thr Gly Asn Ser Gly Phe Thr Tyr Ser Thr Pro Ala
    1175                1180                1185

Phe Ser Glu Asp Phe Phe Lys Glu Ser Ile Ser Ala Pro Lys Phe
    1190                1195                1200

Asn Ser Gly Ser Ser Asp Asp Val Arg Tyr Val Asn Ala Phe Lys
    1205                1210                1215

Phe Met Ser Leu Glu Arg Ile Lys Thr Phe Glu Glu Leu Leu Pro
    1220                1225                1230

Asn Ala Thr Ser Met Phe Asp Asp Tyr Gln Gly Asp Ser Ser Thr
    1235                1240                1245

Leu Leu Ala Ser Pro Met Leu Lys Arg Phe Thr Trp Thr Asp Ser
    1250                1255                1260

Lys Pro Lys Ala Ser Leu Lys Ile Asp Leu Arg Val Thr Ser Lys
    1265                1270                1275

Ser Lys Glu Ser Gly Leu Ser Asp Val Ser Arg Pro Ser Phe Cys
    1280                1285                1290

His Ser Ser Cys Gly His Val Ser Glu Gly Lys Arg Arg Phe Thr
    1295                1300                1305

Tyr Asp His Ala Glu Leu Glu Arg Lys Ile Ala Cys Cys Ser Pro
    1310                1315                1320

Pro Pro Asp Tyr Asn Ser Val Val Leu Tyr Ser Thr Pro Pro Ile
    1325                1330                1335

<210> SEQ ID NO 12
<211> LENGTH: 37
<212> TYPE: DNA

```
<213> ORGANISM: Artificial Sequence
<220> FEATURE:
<223> OTHER INFORMATION: Synthetic primer

<400> SEQUENCE: 12 gaccccccg accttgcaga tcacggagga gtcacac                               37

<210> SEQ ID NO 13
<211> LENGTH: 37
<212> TYPE: DNA
<213> ORGANISM: Artificial Sequence
<220> FEATURE:
<223> OTHER INFORMATION: Synthetic primer

<400> SEQUENCE: 13
gtgtgactcc tccgtgatct gcaaggtcgg gggggtc                              37

<210> SEQ ID NO 14
<211> LENGTH: 39
<212> TYPE: DNA
<213> ORGANISM: Artificial Sequence
<220> FEATURE:
<223> OTHER INFORMATION: Synthetic primer

<400> SEQUENCE: 14
ctgcacgagg tacatgccca ggacacaggc agctacgtc                            39

<210> SEQ ID NO 15
<211> LENGTH: 39
<212> TYPE: DNA
<213> ORGANISM: Artificial Sequence
<220> FEATURE:
<223> OTHER INFORMATION: Synthetic primer

<400> SEQUENCE: 15
gacgtagctg cctgtgtcct gggcatgtac ctcgtgcag                            39

<210> SEQ ID NO 16
<211> LENGTH: 35
<212> TYPE: DNA
<213> ORGANISM: Artificial Sequence
<220> FEATURE:
<223> OTHER INFORMATION: Synthetic primer

<400> SEQUENCE: 16
gtccatcccc ggcctccaag tcacgctgcg ctcgc                                35

<210> SEQ ID NO 17
<211> LENGTH: 35
<212> TYPE: DNA
<213> ORGANISM: Artificial Sequence
<220> FEATURE:
<223> OTHER INFORMATION: Synthetic primer

<400> SEQUENCE: 17
gcgagcgcag cgtgacttgg aggccgggga tggac                                35

<210> SEQ ID NO 18
<211> LENGTH: 37
<212> TYPE: DNA
<213> ORGANISM: Artificial Sequence
<220> FEATURE:
<223> OTHER INFORMATION: Synthetic primer

<400> SEQUENCE: 18
gggagaagct ggtcctccag tgcaccgtgt gggctga                              37
```

<210> SEQ ID NO 19
<211> LENGTH: 37
<212> TYPE: DNA
<213> ORGANISM: Artificial Sequence
<220> FEATURE:
<223> OTHER INFORMATION: Synthetic primer

<400> SEQUENCE: 19
tcagcccaca cggtgcactg gaggaccagc ttctccc            37

<210> SEQ ID NO 20
<211> LENGTH: 38
<212> TYPE: DNA
<213> ORGANISM: Artificial Sequence
<220> FEATURE:
<223> OTHER INFORMATION: Synthetic primer

<400> SEQUENCE: 20
agcatcctga ccatccacca ggtcagccag cacgacct           38

<210> SEQ ID NO 21
<211> LENGTH: 38
<212> TYPE: DNA
<213> ORGANISM: Artificial Sequence
<220> FEATURE:
<223> OTHER INFORMATION: Synthetic primer

<400> SEQUENCE: 21
aggtcgtgct ggctgacctg gtggatggtc aggatgct           38